(12) United States Patent
Chang et al.

(10) Patent No.: US 10,300,104 B2
(45) Date of Patent: *May 28, 2019

(54) MULTI-ARM LINKER FOR TREATING REJECTION REACTION IN TRANSPLANTATION

(71) Applicant: Immunwork Inc., Taipei (TW)

(72) Inventors: Tse-Wen Chang, Taipei (TW); Hsing-Mao Chu, Taipei (TW); Chun-Yu Lin, Taipei (TW); Wei-Ting Tian, Taipei (TW)

(73) Assignee: IMMUNWORK INC., Taipei (TW)

( * ) Notice: Subject to any disclaimer, the term of this patent is extended or adjusted under 35 U.S.C. 154(b) by 145 days.

This patent is subject to a terminal disclaimer.

(21) Appl. No.: 15/253,904

(22) Filed: Sep. 1, 2016

(65) Prior Publication Data

US 2017/0056520 A1  Mar. 2, 2017

Related U.S. Application Data

(60) Provisional application No. 62/308,349, filed on Mar. 15, 2016, provisional application No. 62/213,012, filed on Sep. 1, 2015.

(51) Int. Cl.

| | |
|---|---|
| *A61K 47/68* | (2017.01) |
| *A61K 47/64* | (2017.01) |
| *A61K 47/65* | (2017.01) |
| *A61K 39/44* | (2006.01) |
| *A61K 38/05* | (2006.01) |
| *C07K 16/28* | (2006.01) |
| *A61K 31/137* | (2006.01) |
| *A61K 31/436* | (2006.01) |
| *A61K 31/4545* | (2006.01) |
| *C07K 16/36* | (2006.01) |
| *C07K 7/08* | (2006.01) |
| *C12N 9/72* | (2006.01) |
| *C07K 14/705* | (2006.01) |

(52) U.S. Cl.
CPC ............ *A61K 38/05* (2013.01); *A61K 31/137* (2013.01); *A61K 31/436* (2013.01); *A61K 31/4545* (2013.01); *A61K 39/44* (2013.01); *A61K 47/64* (2017.08); *A61K 47/65* (2017.08); *A61K 47/68* (2017.08); *A61K 47/6811* (2017.08); *A61K 47/6843* (2017.08); *A61K 47/6849* (2017.08); *C07K 7/08* (2013.01); *C07K 16/2866* (2013.01); *C07K 16/36* (2013.01); *C12N 9/6459* (2013.01); *C12Y 304/21068* (2013.01); *C07K 14/70521* (2013.01); *C07K 14/70532* (2013.01); *C07K 2317/20* (2013.01); *C07K 2317/622* (2013.01); *C07K 2319/00* (2013.01); *C07K 2319/035* (2013.01); *C07K 2319/30* (2013.01)

(58) Field of Classification Search
CPC ................ A61K 38/05; A61K 47/6843; A61K 47/6811; A61K 47/65; A61K 47/68; A61K 47/64; A61K 47/6849; A61K 31/137; A61K 31/436; A61K 39/44; C07K 7/08; C07K 16/2833; C07K 16/2896; C07K 14/70539; C07K 2317/20; C07K 2317/622; C07K 2319/00; C07K 2319/30

See application file for complete search history.

(56) References Cited

U.S. PATENT DOCUMENTS

| | | | |
|---|---|---|---|
| 9,907,858 B2 * | 3/2018 | Chang | ................ A61K 47/6801 |
| 9,975,951 B2 * | 5/2018 | Chang | .................. C07K 16/283 |
| 2012/0201746 A1* | 8/2012 | Liu | ........................ C07K 16/00 |
| | | | 424/1.11 |

OTHER PUBLICATIONS

Yu et al., Investigative Ophthalmology & Visual Science 49(2): 522-527, Feb. 2008.*
Jubala et al., Vet Pathol 42: 468-476, 2005.*
Burgess, et al., Journal of Cell Biology, vol. 111, pp. 2129-2138, 1990.*

* cited by examiner

*Primary Examiner* — Phuong Huynh

(57) ABSTRACT

The present disclosure provides various molecular constructs having a targeting element and an effector element. Methods for treating various diseases using such molecular constructs are also disclosed.

13 Claims, 30 Drawing Sheets

Specification includes a Sequence Listing.

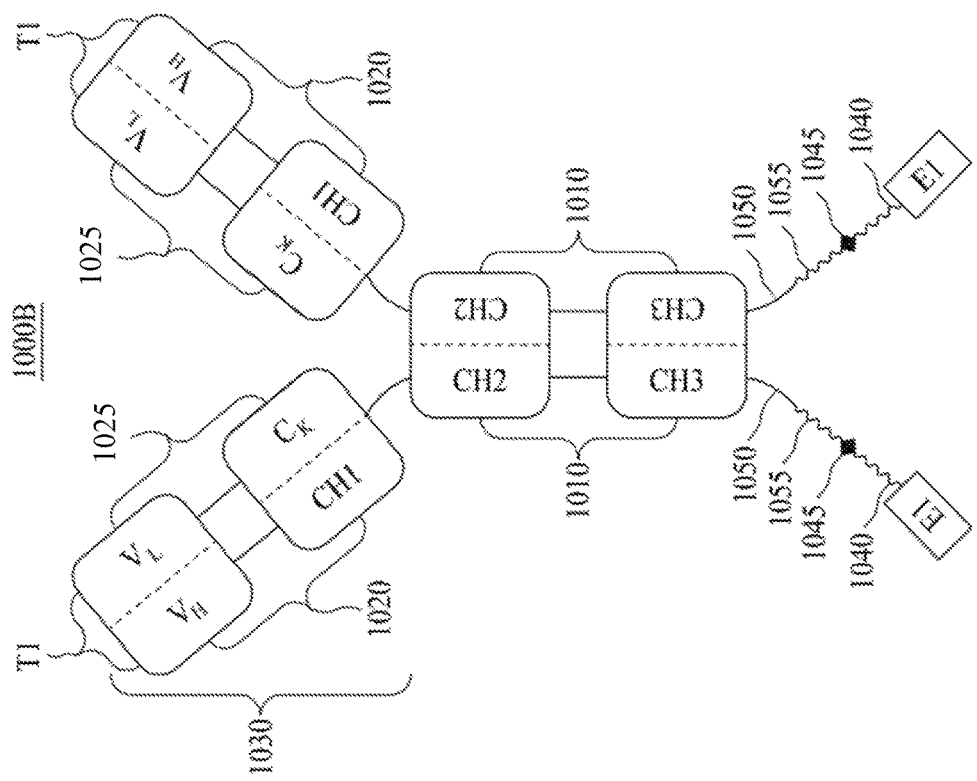
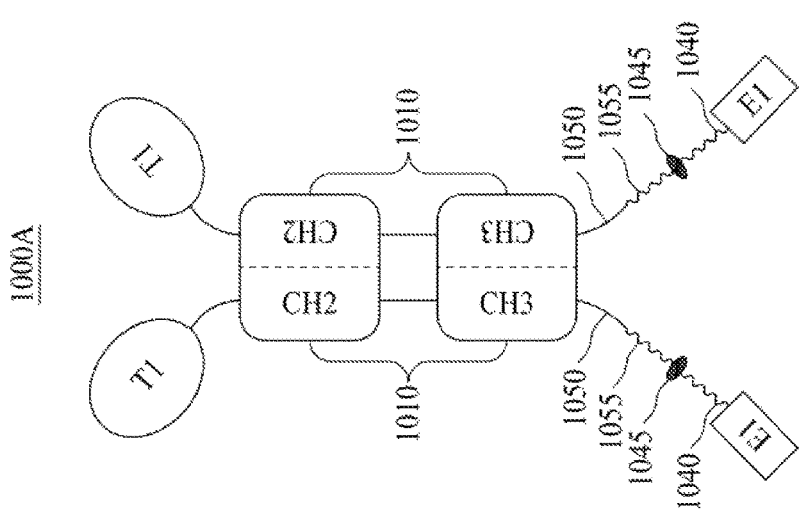
FIG. 5B
FIG. 5A

SEQUENCE LISTING

```
<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: synthesized

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: synthesized
```

```
<400> SEQUENCE: 2

Gly Ser Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: synthesized

<400> SEQUENCE: 3

Gly Gly Ser Gly
1

<210> SEQ ID NO 4
<211> LENGTH: 5
<212> TYPE: PRT
<213> ORGANISM: Artificial Sequence
<220> FEATURE:
<223> OTHER INFORMATION: synthesized

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthesized

<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: synthesized

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: synthesized

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: synthesized
```

```
<400> SEQUENCE: 8

Gly Gly Ser Gly Gly Ser Gly
1               5

<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

Ser Gly Ser Gly Gly Ser Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: synthesized

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: synthesized

<400> SEQUENCE: 11

Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: synthesized

<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: synthesized

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: synthesized
```

```
<400> SEQUENCE: 14

Gly Gly Gly Gly Ser Gly Gly Ser Gly Gly Gly Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: synthesized

<400> SEQUENCE: 15

Gly Gly Gly Ser Gly Ser Gly Ser Gly Ser Gly Gly Gly Ser
1               5                   10

<210> SEQ ID NO 16
<211> LENGTH: 15
<212> TYPE: PRT
<213> ORGANISM: Artificial Sequence
<220> FEATURE:
<223> OTHER INFORMATION: synthesized

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 18

Cys Gly Gly Ser Gly Gly Ser Gly Gly Ser Lys Gly Ser Gly Ser Lys
1               5                   10                  15

Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized
```

<400> SEQUENCE: 19

Cys Gly Ser Lys Gly Ser Lys Gly Ser Lys Gly Ser Lys
1               5                   10                  15

Gly Ser Lys Gly Ser Lys Gly Ser Lys Gly Ser Lys
            20                  25                  30

<210> SEQ ID NO 20
<211> LENGTH: 16
<212> TYPE: PRT
<213> ORGANISM: Artificial Sequence
<220> FEATURE:
<221> NAME/KEY: MISC_FEATURE
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 20

Xaa Gly Gly Ser Gly Gly Ser Gly Gly Ser Lys Gly Ser Gly Ser Lys
1               5                   10                  15

<210> SEQ ID NO 21
<211> LENGTH: 19
<212> TYPE: PRT
<213> ORGANISM: Artificial Sequence
<220> FEATURE:
<221> NAME/KEY: MISC_FEATURE
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 21

Xaa Gly Gly Ser Gly Gly Ser Gly Gly Ser Lys Gly Ser Gly Ser Lys
1               5                   10                  15

Gly Ser Lys

<210> SEQ ID NO 22
<211> LENGTH: 19
<212> TYPE: PRT
<213> ORGANISM: Artificial Sequence
<220> FEATURE:
<221> NAME/KEY: MISC_FEATURE
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 22

Xaa Gly Gly Ser Gly Gly Ser Gly Gly Ser Lys Gly Ser Gly Ser Lys
1               5                   10                  15

Gly Ser Lys

```
<210> SEQ ID NO 23
<211> LENGTH: 21
<212> TYPE: PRT
<213> ORGANISM: Artificial Sequence
<220> FEATURE:
<221> NAME/KEY: MISC_FEATURE
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized

<400> SEQUENCE: 23

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 24
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized
<220> FEATURE:
<221> NAME/KEY: MISC_FEATURE
<222> LOCATION: 2
<223> OTHER INFORMATION: Xaa is PEGylated amino acid
<220> FEATURE:
<221> NAME/KEY: MISC_FEATURE
<222> LOCATION: 4
<223> OTHER INFORMATION: Xaa is PEGylated amino acid
<220> FEATURE:
<221> NAME/KEY: MISC_FEATURE
<222> LOCATION: 6
<223> OTHER INFORMATION: Xaa is PEGylated amino acid

<400> SEQUENCE: 24

Cys Xaa Lys Xaa Lys Xaa Lys
1               5

<210> SEQ ID NO 25
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: synthesized
<220> FEATURE:
<221> NAME/KEY: MISC_FEATURE
<222> LOCATION: 2
<223> OTHER INFORMATION: Xaa is PEGylated amino acid
<220> FEATURE:
<221> NAME/KEY: MISC_FEATURE
<222> LOCATION: 4
<223> OTHER INFORMATION: Xaa is PEGylated amino acid
<220> FEATURE:
<221> NAME/KEY: MISC_FEATURE
<222> LOCATION: 6
<223> OTHER INFORMATION: Xaa is PEGylated amino acid
<220> FEATURE:
<221> NAME/KEY: MISC_FEATURE
<222> LOCATION: 8
<223> OTHER INFORMATION: Xaa is PEGylated amino acid
```

-continued

```
<220> FEATURE:
<221> NAME/KEY: MISC_FEATURE
<222> LOCATION: 10
<223> OTHER INFORMATION: Xaa is PEGylated amino acid

<400> SEQUENCE: 25

Cys Xaa Lys Xaa Lys Xaa Lys Xaa Lys Xaa Lys
1               5                   10

<210> SEQ ID NO 26
<211> LENGTH: 16
<212> TYPE: PRT
<213> ORGANISM: Artificial Sequence
<220> FEATURE:
<223> OTHER INFORMATION: synthesized

<400> SEQUENCE: 26

Cys Gly Ser Lys Gly Ser Lys Gly Ser Lys Gly Ser Lys Gly Ser Lys
1               5                   10                  15

<210> SEQ ID NO 27
<211> LENGTH: 501
<212> TYPE: PRT
<213> ORGANISM: Artificial Sequence
<220> FEATURE:
<223> OTHER INFORMATION: HLA-A1-IgG1.Fc

<400> SEQUENCE: 27

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Lys Met Glu Pro Arg
        35                  40                  45

Ala Pro Trp Ile Glu Gln Glu Gly Pro Glu Tyr Trp Asp Gln Glu Thr
    50                  55                  60

Arg Asn Met Lys Ala His Ser Gln Thr Asp Arg Ala Asn Leu Gly Thr
65                  70                  75                  80

Leu Arg Gly Tyr Tyr Asn Gln Ser Glu Asp Gly Ser His Thr Ile Gln
                85                  90                  95

Ile Met Tyr Gly Cys Asp Val Gly Pro Asp Gly Arg Phe Leu Arg Gly
            100                 105                 110

Tyr Arg Gln Asp Ala Tyr Asp Gly Lys Asp Tyr Ile Ala Leu Asn Glu
        115                 120                 125

Asp Leu Arg Ser Trp Thr Ala Ala Asp Met Ala Ala Gln Ile Thr Lys
    130                 135                 140

Arg Lys Trp Glu Ala Val His Ala Ala Glu Gln Arg Arg Val Tyr Leu
145                 150                 155                 160

Glu Gly Arg Cys Val Asp Gly Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240
```

-continued

```
Phe Gln Lys Trp Ala Ala Val Val Pro Ser Gly Glu Glu Gln Arg
                245                 250                 255

Tyr Thr Cys His Val Gln His Glu Gly Leu Pro Lys Pro Leu Thr Leu
            260                 265                 270

Arg Trp Gly Gly Gly Ala Ser Cys Pro Pro Cys Pro Ala Pro Glu Leu
        275                 280                 285

Leu Gly Gly Pro Ser Val Phe Leu Phe Pro Pro Lys Pro Lys Asp Thr
    290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Asp Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Arg Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
    450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500
```

<210> SEQ ID NO 28
<211> LENGTH: 501
<212> TYPE: PRT
<213> ORGANISM: Artificial Sequence
<220> FEATURE:
<223> OTHER INFORMATION: HLA-A2-IgG1.Fc

<400> SEQUENCE: 28

```
Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95
```

```
Arg Met Tyr Gly Cys Asp Val Gly Ser Asp Trp Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Asp Met Ala Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Gly Gly Ala Ser Cys Pro Pro Cys Pro Ala Pro Glu Leu Leu
        275                 280                 285

Leu Gly Gly Pro Ser Val Phe Leu Phe Pro Pro Lys Pro Lys Asp Thr
290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Asp Tyr Lys Cys Lys Val Ser Asn Lys Ala Leu Pro Ala
370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Asp Glu Leu Thr Arg Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Pro Gly Lys
            500
```

```
<210> SEQ ID NO 29
<211> LENGTH: 390
<212> TYPE: PRT
<213> ORGANISM: Artificial Sequence
<220> FEATURE:
<223> OTHER INFORMATION: PD-1-IgG1.Fc

<400> SEQUENCE: 29

Ala Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Glu Asn Leu Tyr Phe Gln Ser Ala Ser Gly
145                 150                 155                 160

Gly Ser Gly Gly Gly Gly Ser Gly Gly Gly Gly Ser Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Arg Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365
```

Ser Val Met His Glu Ala Leu His Asn His Tyr Thr Gln Lys Ser Leu
    370                 375                 380

Ser Leu Ser Pro Gly Lys
385                 390

<210> SEQ ID NO 30
<211> LENGTH: 135
<212> TYPE: PRT
<213> ORGANISM: Artificial Sequence
<220> FEATURE:
<223> OTHER INFORMATION: CTLA-4-Linker-Cys

<400> SEQUENCE: 30

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gly Gly Gly Gly
        115                 120                 125

Ser Gly Gly Gly Gly Ser Cys
    130                 135

<210> SEQ ID NO 31
<211> LENGTH: 231
<212> TYPE: PRT
<213> ORGANISM: Artificial Sequence
<220> FEATURE:
<223> OTHER INFORMATION: PDL1-Linker-Cys

<400> SEQUENCE: 31

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

```
Ala Glu Val Ile Trp Thr Ser Ser Asp His Gln Val Leu Ser Gly Lys
145                 150                 155                 160

Thr Thr Thr Thr Asn Ser Lys Arg Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Gly Gly Gly
    210                 215                 220

Ser Gly Gly Gly Gly Ser Cys
225                 230
```

<210> SEQ ID NO 32
<211> LENGTH: 258
<212> TYPE: PRT
<213> ORGANISM: Artificial Sequence
<220> FEATURE:
<223> OTHER INFORMATION: anti-HLA-A1 4-35-7 scFv

<400> SEQUENCE: 32

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Asp Tyr Ser Val
            85                  90                  95

Thr Phe Gly Ala Gly Thr Lys Val Glu Ile Lys Arg Gly Gly Gly Gly
        100                 105                 110

Ser Gly Gly Gly Gly Ser Gly Gly Gly Ser Glu Val Gln Leu Leu
        115                 120                 125

Glu Ser Gly Gly Gly Leu Val Gln Pro Gly Gly Ser Gln Arg Leu Ser
130                 135                 140

Cys Val Ala Ser Gly Val Pro Phe Ser Asn Tyr Ala Met Asn Trp Val
145                 150                 155                 160

Arg Gln Ala Pro Gly Lys Gly Leu Glu Trp Val Ser Ser Ile Ser Gly
                165                 170                 175

Gly Gly Asp Arg Thr Phe Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Gly Ala Gly Asp Thr Ala Val Tyr Tyr Cys Ala Lys Thr Tyr Tyr
    210                 215                 220

Asp Phe Trp Ser Gly Tyr Ser Arg His Leu Asn Ser Trp Gly Gln Gly
225                 230                 235                 240

Ser Leu Val Thr Val Ser Ser Gly Gly Gly Ser Gly Gly Gly Gly
                245                 250                 255

Ser Cys
```

```
<210> SEQ ID NO 33
<211> LENGTH: 249
<212> TYPE: PRT
<213> ORGANISM: Artificial Sequence
<220> FEATURE:
<223> OTHER INFORMATION: anti-CD25 scFv, Dacilizumab scFv

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Ser Gly Thr Lys Val Glu Val Lys Arg Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Val Ser Cys
    130                 135                 140

Lys Ala Ser Gly Tyr Thr Phe Thr Ser Tyr Arg Met His Trp Val Arg
145                 150                 155                 160

Gln Ala Pro Gly Gln Gly Leu Glu Trp Ile Gly Tyr Ile Asn Pro Ser
                165                 170                 175

Thr Gly Tyr Thr Glu Tyr Asn Gln Lys Phe Lys Asp Lys Ala Thr Ile
            180                 185                 190

Thr Ala Asp Glu Ser Thr Asn Thr Ala Tyr Met Glu Leu Ser Ser Leu
        195                 200                 205

Arg Ser Glu Asp Thr Ala Val Tyr Tyr Cys Ala Arg Gly Gly Gly Val
    210                 215                 220

Phe Asp Tyr Trp Gly Gln Gly Thr Thr Leu Thr Val Ser Ser Gly Gly
225                 230                 235                 240

Gly Gly Ser Gly Gly Gly Gly Ser Cys
                245

<210> SEQ ID NO 34
<211> LENGTH: 243
<212> TYPE: PRT
<213> ORGANISM: Artificial Sequence
<220> FEATURE:
<223> OTHER INFORMATION: phage-displayed scFv specific for HLA-A2, 3E10

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Phe Phe Phe
            20                  25                  30

Val Ala Trp Tyr Gln Gln Lys Pro Gly Lys Ala Pro Lys Leu Leu Ile
        35                  40                  45

Tyr Gly Pro Pro Gly Leu Tyr Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Phe Ser Phe Pro Ile
                 85                  90                  95

Thr Phe Gly Gln Gly Thr Lys Val Glu Ile Lys Arg Gly Gly Gly Gly
            100                 105                 110

Ser Ile Glu Gly Arg Ser Gly Gly Gly Ser Glu Val Gln Leu Val
            115                 120                 125

Glu Ser Gly Gly Gly Leu Val Gln Pro Gly Gly Ser Leu Arg Leu Ser
    130                 135                 140

Cys Ala Ala Ser Gly Phe Thr Ile Ser Asn Gly Gly Ile His Trp Val
145                 150                 155                 160

Arg Gln Ala Pro Gly Lys Gly Leu Glu Trp Val Ala Ser Ile Trp Pro
                165                 170                 175

Ser Gly Gly Tyr Thr Ser Tyr Ala Asp Ser Val Lys Gly Arg Phe Thr
            180                 185                 190

Ile Ser Ala Asp Thr Ser Lys Asn Thr Ala Tyr Leu Gln Met Asn Ser
        195                 200                 205

Leu Arg Ala Glu Asp Thr Ala Val Tyr Tyr Cys Ala Arg Phe Gly Val
    210                 215                 220

Asn Tyr His Gly Ile Met Asp Tyr Trp Gly Gln Gly Thr Leu Val Thr
225                 230                 235                 240

Val Ser Ser

<210> SEQ ID NO 35
<211> LENGTH: 614
<212> TYPE: PRT
<213> ORGANISM: Artificial Sequence
<220> FEATURE:
<223> OTHER INFORMATION: CTLA-4-IgG1.Fc-(anti-HLA scFv)

<400> SEQUENCE: 35

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175
```

```
Ser His Glu Asp Pro Glu Val Lys Phe Asn Trp Tyr Val Asp Gly Val
            180                 185                 190
Glu Val His Asn Ala Lys Thr Lys Pro Arg Glu Gln Tyr Asn Ser
        195                 200                 205
Thr Tyr Arg Val Val Ser Val Leu Thr Val Leu His Gln Asp Trp Leu
    210                 215                 220
Asn Gly Lys Glu Tyr Lys Cys Lys Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Tyr Thr Leu Pro Pro Ser Arg Asp Glu Leu Thr Lys Asn Gln
            260                 265                 270
Val Ser Leu Thr Cys Leu Val Lys Gly Phe Tyr Pro Ser Asp Ile Ala
        275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Tyr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys Gly Gly Gly Gly Ser Gly Gly Gly Gly Ser Asp
        355                 360                 365
Ile Gln Met Thr Gln Ser Pro Ser Thr Leu Ser Ala Ser Val Gly Asp
    370                 375                 380
Arg Val Thr Ile Thr Cys Arg Ala Ser Gln Ser Ile Ser Asn Trp Leu
385                 390                 395                 400
Ala Trp Tyr Gln Gln Lys Pro Gly Lys Ala Pro Asn Leu Leu Ile Tyr
                405                 410                 415
Lys Ala Ser Ser Leu Glu Ser Gly Val Pro Ser Arg Phe Ser Gly Ser
            420                 425                 430
Gly Ser Gly Thr Glu Phe Thr Leu Thr Ile Ser Ser Leu Gln Pro Asp
        435                 440                 445
Asp Phe Ala Thr Tyr Tyr Cys Gln Gln Tyr His Asp Tyr Ser Val Thr
    450                 455                 460
Phe Gly Ala Gly Thr Lys Val Glu Ile Lys Arg Gly Gly Gly Gly Ser
465                 470                 475                 480
Gly Gly Gly Gly Ser Gly Gly Gly Ser Glu Val Gln Leu Leu Glu
                485                 490                 495
Ser Gly Gly Gly Leu Val Gln Pro Gly Ser Gln Arg Leu Ser Cys
            500                 505                 510
Val Ala Ser Gly Val Pro Phe Ser Asn Tyr Ala Met Asn Trp Val Arg
        515                 520                 525
Gln Ala Pro Gly Lys Gly Leu Glu Trp Val Ser Ser Ile Ser Gly Gly
    530                 535                 540
Gly Asp Arg Thr Phe Tyr Ala Asp Ser Val Lys Gly Arg Phe Thr Ile
545                 550                 555                 560
Ser Arg Asp Asn Ser Lys Asn Thr Leu Tyr Leu Gln Met Asn Ser Leu
                565                 570                 575
Gly Ala Gly Asp Thr Ala Val Tyr Tyr Cys Ala Lys Thr Tyr Tyr Asp
            580                 585                 590
```

Phe Trp Ser Gly Tyr Ser Arg His Leu Asn Ser Trp Gln Gly Ser
        595                 600                 605

Leu Val Thr Val Ser Ser
    610

<210> SEQ ID NO 36
<211> LENGTH: 711
<212> TYPE: PRT
<213> ORGANISM: Artificial Sequence
<220> FEATURE:
<223> OTHER INFORMATION: PDL1-IgG4.Fc-(anti-HLA scFv)

<400> SEQUENCE: 36

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Ala Ser Gly Gly
    210                 215                 220

Ser Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

```
Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys Gly Gly Gly Gly Ser Gly Gly Gly Gly Ser Gly Gly Gly Gly Ser
            450                 455                 460

Asp Ile Gln Met Thr Gln Ser Pro Ser Thr Leu Ser Ala Ser Val Gly
465                 470                 475                 480

Asp Arg Val Thr Ile Thr Cys Arg Ala Ser Gln Ser Ile Ser Asn Trp
                485                 490                 495

Leu Ala Trp Tyr Gln Gln Lys Pro Gly Lys Ala Pro Asn Leu Leu Ile
            500                 505                 510

Tyr Lys Ala Ser Ser Leu Glu Ser Gly Val Pro Ser Arg Phe Ser Gly
            515                 520                 525

Ser Gly Ser Gly Thr Glu Phe Thr Leu Thr Ile Ser Ser Leu Gln Pro
530                 535                 540

Asp Asp Phe Ala Thr Tyr Tyr Cys Gln Gln Tyr His Asp Tyr Ser Val
545                 550                 555                 560

Thr Phe Gly Ala Gly Thr Lys Val Glu Ile Lys Arg Gly Gly Gly Gly
                565                 570                 575

Ser Gly Gly Gly Gly Ser Gly Gly Gly Gly Ser Glu Val Gln Leu Leu
            580                 585                 590

Glu Ser Gly Gly Gly Leu Val Gln Pro Gly Gly Ser Gln Arg Leu Ser
            595                 600                 605

Cys Val Ala Ser Gly Val Pro Phe Ser Asn Tyr Ala Met Asn Trp Val
610                 615                 620

Arg Gln Ala Pro Gly Lys Gly Leu Glu Trp Val Ser Ser Ile Ser Gly
625                 630                 635                 640

Gly Gly Asp Arg Thr Phe Tyr Ala Asp Ser Val Lys Gly Arg Phe Thr
                645                 650                 655

Ile Ser Arg Asp Asn Ser Lys Asn Thr Leu Tyr Leu Gln Met Asn Ser
            660                 665                 670

Leu Gly Ala Gly Asp Thr Ala Val Tyr Tyr Cys Ala Lys Thr Tyr Tyr
            675                 680                 685

Asp Phe Trp Ser Gly Tyr Ser Arg His Leu Asn Ser Trp Gly Gln Gly
690                 695                 700

Ser Leu Val Thr Val Ser Ser
705                 710
```

<210> SEQ ID NO 37
<211> LENGTH: 729
<212> TYPE: PRT
<213> ORGANISM: Artificial Sequence
<220> FEATURE:
<223> OTHER INFORMATION: (anti-CD25 scFv)-IgG4.Fc-(anti-HLA scFv)

-continued

```
<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ile Ser Tyr Met
            20                  25                  30

His Trp Tyr Gln Gln Lys Pro Gly Lys Ala Pro Lys Leu Leu Ile Tyr
            35                  40                  45

Thr Thr Ser Asn Leu Ala Ser Gly Val Pro Ala Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Ser Gly Thr Lys Val Glu Val Lys Arg Gly Gly Gly Gly Ser
            100                 105                 110

Gly Gly Gly Gly Ser Gly Gly Gly Ser Gln Val Gln Leu Val Gln
        115                 120                 125

Ser Gly Ala Glu Val Lys Lys Pro Gly Ser Ser Val Lys Val Ser Cys
    130                 135                 140

Lys Ala Ser Gly Tyr Thr Phe Thr Ser Tyr Arg Met His Trp Val Arg
145                 150                 155                 160

Gln Ala Pro Gly Gln Gly Leu Glu Trp Ile Gly Tyr Ile Asn Pro Ser
                165                 170                 175

Thr Gly Tyr Thr Glu Tyr Asn Gln Lys Phe Lys Asp Lys Ala Thr Ile
            180                 185                 190

Thr Ala Asp Glu Ser Thr Asn Thr Ala Tyr Met Glu Leu Ser Ser Leu
        195                 200                 205

Arg Ser Glu Asp Thr Ala Val Tyr Tyr Cys Ala Arg Gly Gly Gly Val
    210                 215                 220

Phe Asp Tyr Trp Gly Gln Gly Thr Thr Leu Thr Val Ser Ser Ala Ser
225                 230                 235                 240

Gly Gly Ser Pro Pro Cys Pro Ser Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

-continued

```
Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys Gly Gly Gly Gly Ser Gly Gly Gly Ser Gly Gly Gly
465                 470                 475                 480

Gly Ser Asp Ile Gln Met Thr Gln Ser Pro Ser Thr Leu Ser Ala Ser
                485                 490                 495

Val Gly Asp Arg Val Thr Ile Thr Cys Arg Ala Ser Gln Ser Ile Ser
            500                 505                 510

Asn Trp Leu Ala Trp Tyr Gln Gln Lys Pro Gly Lys Ala Pro Asn Leu
        515                 520                 525

Leu Ile Tyr Lys Ala Ser Ser Leu Glu Ser Gly Val Pro Ser Arg Phe
530                 535                 540

Ser Gly Ser Gly Ser Gly Thr Glu Phe Thr Leu Thr Ile Ser Ser Leu
545                 550                 555                 560

Gln Pro Asp Asp Phe Ala Thr Tyr Tyr Cys Gln Gln Tyr His Asp Tyr
            565                 570                 575

Ser Val Thr Phe Gly Ala Gly Thr Lys Val Glu Ile Lys Arg Gly Gly
            580                 585                 590

Gly Gly Ser Gly Gly Gly Gly Ser Gly Gly Gly Gly Ser Glu Val Gln
        595                 600                 605

Leu Leu Glu Ser Gly Gly Gly Leu Val Gln Pro Gly Gly Ser Gln Arg
610                 615                 620

Leu Ser Cys Val Ala Ser Gly Val Pro Phe Ser Asn Tyr Ala Met Asn
625                 630                 635                 640

Trp Val Arg Gln Ala Pro Gly Lys Gly Leu Glu Trp Val Ser Ser Ile
            645                 650                 655

Ser Gly Gly Gly Asp Arg Thr Phe Tyr Ala Asp Ser Val Lys Gly Arg
            660                 665                 670

Phe Thr Ile Ser Arg Asp Asn Ser Lys Asn Thr Leu Tyr Leu Gln Met
        675                 680                 685

Asn Ser Leu Gly Ala Gly Asp Thr Ala Val Tyr Tyr Cys Ala Lys Thr
    690                 695                 700

Tyr Tyr Asp Phe Trp Ser Gly Tyr Ser Arg His Leu Asn Ser Trp Gly
705                 710                 715                 720

Gln Gly Ser Leu Val Thr Val Ser Ser
                725
```

MULTI-ARM LINKER FOR TREATING REJECTION REACTION IN TRANSPLANTATION

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

<I> Peptide Core-Based Multi-Arm Linkers for Treating Rejection Reaction in Transplantation and Uses Thereof In the first aspect, the present disclosure is directed to a linker unit for treating transplantation rejection in a subject. In particular, the linker unit has at least two different functional elements linked thereto. For example, the linker unit may have linked thereto two different effector elements, one targeting element and one effector element, or one effector element and a polyethylene glycol (PEG) chain for prolonging the circulation time of the linker unit. The present linker unit is designed to have at least two different functional groups such that the functional elements can be linked thereto by reacting with the respective functional groups. Accordingly, the present linker unit can serve as a platform for preparing a molecular construct with two or more functional elements. As could be appreciated, methods for treating a transplant patient using such linker unit also fall within the aspect of the present disclosure According to various embodiments of the present disclosure, the linker unit comprises a center core, a plurality of linking arms, a plurality of first elements, and optionally, a coupling arm and a second element.

According to various embodiments of the present disclosure, the center core is a peptide core having a pre-defined number of amine (—NH$_2$) groups, before being linked with the linking arms. For example, the peptide core may have two or more lysine (K) resides having an amine (—NH$_2$) group at the side chain.

In certain embodiments, the peptide core comprises 2 to 15 K resides and one or more filler sequences, in which each K residue and a next K residue are separated by one of the filler sequences. Each of the filler sequences comprises glycine (G) and serine (S) residues. Optionally, the filler sequence consists of 2 to 20 amino acid residues. In various embodiments, the filler sequence may have the sequence of GS, GGS, GSG, or SEQ ID NOs: 1-16. In certain embodiments of the present disclosure, at least one of the filler sequences in one peptide core differs from the remaining filler sequences of the same peptide core. According to some embodiments of the present disclosure, the peptide core comprises 2 to 15 units of the sequence of $G_{1-5}SK$; preferably, the peptide core comprises the sequence of $(GSK)_{2-15}$.

According to some other embodiments, the peptide core comprises the sequence of $(X_{aa}-K)_{2-15}$, in which $X_{aa}$ is a PEGylated amino acid having 2 to 12 repeats of ethylene glycol (EG) unit.

Each of the linking arms is linked to the amine groups of the center core via forming an amide linkage between the amine group and the linking arm. As could be appreciated, in the case of a peptide core, the linking arm is linked to the center core by reacting with the amine group at the side chain of the K residue. Further, the linking arm linked to the center core has a maleimide, an N-hydroxysuccinimidyl (NHS) group, an azide group, an alkyne group, a tetrazine group, a cyclooctene group, or a cyclooctyne group at its free-terminus.

On the other hand, for the peptide core, the amino acid residue at the N- or C-terminus of the center core has an azide group or an alkyne group; alternatively or additionally, the amino acid residue at the N- or C-terminus of the center core is a cysteine (C) residue.

According to certain embodiments of the present disclosure, when the center core is a a peptide core having a terminal amino acid residue of Cysteine, the present linker unit comprises said coupling arm. For peptide cores with terminal the terminal amino acid residue of Cysteine, one end of the coupling arm is linked to the Cysteine residue by reacting with the thiol group thereof.

Regarding amino acid residues having the azide group, non-limiting examples of said amino acid residues include L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. As to the amino acid residues having the alkyne group, illustrative examples thereof include L-homopropargylglycine (L-HPG), D-homopropargylglycine (D-HPG), and beta-homopropargylglycine (β-HPG).

When the amino acid residues at the N- or C-terminus of the center core is the cysteine residue, the cyclooctene group at the free terminus of the coupling arm may be, a trans-cyclooctene (TCO) group, while the cyclooctyne group at the free terminus of the coupling arm may be a dibenzocyclooctyne (DBCO), difluorinated cyclooctyne (DIFO), bicyclononyne (BCN), or dibenzocyclooctyne (DICO) group. Alternatively, the tetrazine group at the free terminus of the coupling arm includes, but is not limited to, 1,2,3,4-tetrazine, 1,2,3,5-tetrazine, and 1,2,4,5-tetrazine, and derivatives thereof, such as, 6-methyl tetrazine.

In some embodiments, the linking arm is a PEG chain, preferably having 2 to 20 repeats of EG units. In other embodiments, the coupling linking arm is a PEG chain, preferably having 2 to 12 repeats of EG units.

According to various optional embodiments of the present disclosure, the first element is an effector element suitable for eliciting an intended effect (e.g., a therapeutic effect) in a subject. Alternatively, the first element may be a targeting element for directing the linker unit to the site of interest. In preferred embodiments, when the first element is the effector element, the second element is the targeting element, and vice versa.

Specifically, the targeting element according to various embodiments of the present disclosure is an antibody fragment specific for a human leukocyte antigen (HLA) allotype present only on cells of the donor transplant and not on cells of the recipient, such as the HLA-A, HLA-B, and HLA-C allotype. Also, the effector element is an immunosuppressant, an immune checkpoint protein, or an antibody fragment specific for CD25. Illustrative examples of immunosuppressant are inhibitors of mammalian target of rapamycin (mTOR), e.g. sirolimus and everolimus. Another set of immunosuppressants are inhibitors of calcineurin, e.g. tacrolimus. Fingolimod and derivatives thereof (e.g., fingolimod phosphate) are also examples of suitable immunosuppressants Immune checkpoint proteins are those involve in immune checkpoint, such as the extracellular domain of cytotoxic T lymphocyte associated protein 4 (CTLA-4, also known as CD151) and the extracellular domain of programmed death-ligand 1 (PD-L1, also known as CD274).

In some embodiments, each of the first elements is linked to one of the linking arms via forming an amide bound between the linking arm and the first element. In other embodiments, each of the first elements is linked to one of the linking arms via thiol-maleimide reaction, copper catalyzed azide-alkyne cycloaddition (CuAAC) reaction, strained-promoted azide-alkyne click chemistry (SPAAC) reaction, or inverse electron demand Diels-Alder (iEDDA) reaction occurred between the linking arm and the first element.

According to some embodiments of the present disclosure, when the plurality of first elements are respectively linked to the plurality of linking arms via CuAAC or SPAAC reaction, then the amino acid residue at the N- or C-terminus of the center core is a cysteine residue, and the free terminus of the coupling arm is the tetrazine or the cyclooctene group. According to other embodiments of the present disclosure, when the plurality of first elements are respectively linked to the plurality of linking arms via iEDDA reaction, then the amino acid residue at the N- or C-terminus of the center core has the azide or the alkyne group, or the amino acid residue at the N- or C-terminus of the center core is a cysteine residue, and the free terminus of the coupling arm is the azide, the alkyne, or the cyclooctyne group.

In some embodiments, the second element has an azide or alkyne group, so that it is linked to the center core or the coupling arm by coupling with the corresponding alkyne or azide group of the center core or the coupling arm via CuAAC reaction. Alternatively, in other embodiments, the second element having an azide or cyclooctyne group is linked to the center core or the coupling arm by coupling with the corresponding cyclooctyne or azide group of the center core or the coupling arm via SPAAC reaction. Still alternatively, in certain embodiments, the second element having a tetrazine or cyclooctyne group is linked to the center core or the coupling arm by coupling with the corresponding cyclooctene or tetrazine group of the center core or the coupling arm via iEDDA reaction.

In certain embodiments, the linker unit further comprises an optional third element that is different from the first and second elements. In the case where the second element is directly linked to the center core, the other terminus (i.e., the free terminus that is not linked with the second element) of the center core is optionally a cysteine residue, which can be used to introduce an optional third element. Specifically, the thiol group of the cysteine residue is reacted with a maleimide group of a PEG chain; and the thus-linked PEG chain is designated as the coupling arm, which has a tetrazine group or a cyclooctene group at its free terminus. Accordingly, the third element is then linked to the coupling arm via iEDDA reaction. Preferably, the third element is an element for improving the pharmacokinetic property of the linker unit. One example of the element for improving the pharmacokinetic property is a long PEG chain having a molecular weight of about 20,000 to 50,000 Daltons.

The linker unit according to this aspect of the present disclosure may find its utility in clinical medicine for the treatment of transplantation rejection. Accordingly, the present disclosure is also directed to a method for suppressing or inhibiting transplantation rejection in a subject receiving a donor transplant (e.g., organ, tissue or cells), or for use in the manufacture of a medicament for such uses. According to various embodiments of the present disclosure, the method for treating the transplantation rejection in a particular subject includes the step of administering to the subject in need thereof a therapeutically effective amount of the linker unit according to the above-mentioned aspect and embodiments of the present disclosure. As could be appreciated, said linker unit may be administered in a pharmaceutical formulation, which comprises a pharmaceutically-acceptable excipient suitable for the intended or desired administration route, in addition to the present linker unit.

<II> Fc-based Molecular Construct for Treating Rejection Reaction in Transplantation and Uses Thereof In this aspect, the present disclosure is directed to a fragment crystallizable (Fc)-based molecular construct that has at least one targeting element and at least one effector element linked, directly or indirectly, to a CH2-CH3 domain of an immunoglobulin. Targeting and effector elements of the present Fc-based molecular constructs are specifically selected such that these Fc-based molecular constructs are suitable for use in suppressing or inhibiting the transplantation rejection in a subject (or recipient) receiving an organ, tissue or cell transplantation, or for use in the manufacture of a medicament for such uses. As could be appreciated, methods for treating transplantation rejection using such Fc-based molecular constructs also fall within the aspect of the present disclosure.

According to certain embodiments of the present disclosure, the Fc-based molecular construct comprises a pair of CH2-CH3 segments of an IgG.Fc, a pair of effector elements, and a pair of targeting elements.

According to various embodiments of the present disclosure, the pair of targeting elements is an antibody fragment specific for a human leukocyte antigen (HLA) allotype present only on cells of the donor transplant and not on cells of the recipient, such as the HLA-A, HLA-B, and HLA-C allotype present only on cells of the donor transplant. Also, the pair of elements is an immune checkpoint protein, an antibody fragment specific for CD25, or a drug bundle comprising an immunosuppressant. Immune checkpoint proteins are those involve in immune checkpoint, such as the extracellular domain of cytotoxic T lymphocyte associated protein 4 (CTLA-4, also known as CD151) and the extracellular domain of programmed death-ligand 1 (PD-L1, also known as CD274). Illustrative examples of immunosuppressant are inhibitors of mammalian target of rapamycin (mTOR), e.g. sirolimus and everolimus. Another set of immunosuppressants are inhibitors of calcineurin, e.g. tacrolimus. Fingolimod and derivatives thereof (e.g., fingolimod phosphate) are also examples of suitable immunosuppressants In the case where the effector element is the immune checkpoint protein, then the pair of effector elements is linked to the N-termini of the pair of CH2-CH3 segments, and the pair of targeting elements is linked to the C-termini of the pair of CH2-CH3 segments, or vice versa. Alternatively, when the effector element is the drug bundle, then the pair of effector elements is linked to the C-termini of the pair of CH2-CH3 segments, and the pair of targeting elements is linked to the N-termini of the pair of CH2-CH3 segments. Still alternatively, when the effector elements are the antibody fragments, then the effector elements is respectively linked to the N-termini of the pair of CH2-CH3 segments, and the targeting elements is respectively linked to the C-termini of the pair of CH2-CH3 segments, and vice versa.

According to certain embodiments, when the pair of effector elements and the pair of targeting elements are both in the form of single-chain variable fragments (scFvs), then the pair of targeting elements is linked to the N-termini of the pair of effector elements in a tandem or diabody configuration, thereby forming a pair of bispecific scFvs that are linked to the N-termini of the pair of CH2-CH3 segments.

In some examples, the pair of the targeting elements takes a Fab configuration (i.e., consisting of the $V_H$-CH1 domain and the $V_L$-$C_K$ domain); this Fab fragment is linked to the N-termini of the first and second heavy chains, so that the Fc-based molecular construct adopts an IgG configuration. In these cases, the pair of effector elements is linked to the C-termini of the pair of CH2-CH3 segments.

According to some other embodiments of the present disclosure, when the pair of effector elements is in the form of an antigen-binding fragment (Fab), and the pair of targeting elements is in the form of scFvs, and vice versa; then the Fab and scFvs are respectively linked to the N-termini and C-termini of the CH2-CH3 segments, so that the molecular construct adopts an extended IgG configuration.

In certain embodiments, the pair of CH2-CH3 segments is derived from human IgG heavy chain γ4 or human IgG heavy chain γ1.

According to some optional embodiments, the effector elements are drug bundles based on linker units. Such drug bundles are advantageous at least in that they can be manufactured separately before being conjugated to the antibody molecules, thus avoiding subjecting drug molecules under harsh chemical conditions for the direct conjugation with the antibody molecules. According to various embodiments of the present disclosure, the drug bundle comprises a plurality of immunosuppressant molecules. As an example, rather than a limitation, these Fc-based molecular constructs are useful in the treatment of transplantation rejection.

According to certain embodiments, the present Fc-based molecular construct further comprises a peptide extension and a coupling arm. Specifically, the peptide extension has the sequence of $(G_{2-4}S)_{2-8}C$ and is linked to the C-terminus of one of the pair of CH2-CH3 segments. In such cases, the coupling arm is linked to the C-terminus of the peptide extension via thiol-maleimide reaction occurred therebetween. Also, before being conjugated with the drug bundle, the free terminus of the coupling arm (that is, the terminus that is not linked to the cysteine residue) is modified with an alkyne, azide, strained alkyne, or tetrazine group, so that the drug bundle is linked thereto via inverse electron demand Diels-Alder (iEDDA) reaction or the strain-promoted azide-alkyne click chemistry (SPAAC) reaction or Copper(I)-catalyzed alkyne-azide cycloaddition (CuAAC) reaction occurred therebetween.

According to some optional embodiments, the drug bundle is a linker unit-based molecular construct according to the first aspect and embodiments of the present disclosure.

Briefly, the center core may be a polypeptide comprising a plurality of lysine (K) residues, according to various embodiments of the present disclosure. Each of the linking arms has one terminus that is linked to the center core by reacting with the amine groups at the side chain of the K residues of the polypeptide core. The linking arm also carries a maleimide group at the free terminus thereof, wherein each of the molecules (e.g., immunosuppressant molecules) is linked to the center core through the linking arm by reacting with the maleimide group.

In the case where the center core is the polypeptide core, then the amino acid residue at the N- or C-terminus of the center core is a cysteine residue or has an azide group or an alkyne group.

For polypeptide cores with a terminal amino acid residue having the azide group or the alkyne group, the drug bundle may be linked to the peptide extension via the CuAAC reaction occurred between said terminal residue and the C-terminus of the peptide extension.

Methods for suppressing or inhibiting transplantation rejection in a subject in need thereof comprise the step of administering to the subject an effective amount of the molecular construct of this aspect.

BRIEF DESCRIPTION OF THE DRAWINGS

The present description will be better understood from the following detailed description read in light of the accompanying drawings briefly discussed below.

FIGS. 5A and 5B are schematic diagrams illustrating Fc-based molecular constructs according to various embodiments of the present disclosure.

Figure 1A:
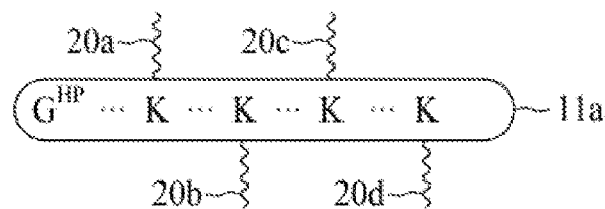
FIG. 1A to FIG. 1K are schematic diagrams illustrating linker units according to certain embodiments of the present disclosure.

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-COOH$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral, and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

Throughout the present disclosure, the term "transplantation rejection" refers to the acute or chronic rejection of cells, tissue or solid organ allografts or xenografts of, among the others, pancreatic islets, stem cells, bone marrow, skin, muscle, corneal tissue, neuronal tissue, heart, lung, combined heart-lung, kidney, liver, bowel, pancreas, trachea or esophagus, or graft-versus-host diseases.

As used herein, the term "donor transplant" refers to a population of cells, or a tissue or an organ that is to be moved from one body to another or from a donor site to another location on the subject's own body, for the purpose of replacing the recipient's damaged or absent tissue or organ.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Certain antibody drugs, which target infectious microorganisms or their toxic products, can be improved, if they are empowered with the ability to recruit immunocytes, which phagocytose and clear the antibody-bound particles. Following are primary examples of diseases, in which drugs can be improved if they can be preferentially distributed to the disease sites or cells or if they can recruit phagocytic immunocytes.

Examples of transplantation-related diseases/conditions include, but are not limited to, organ transplant rejection (including, chronic, acute, subacute, and hyperacute rejection) and graft-versus-host disease (GvHD).

Transplantation is the act of transferring cells, tissues, or organs from one body to another or from a donor site to another location of the person's own body. The malfunction of an organ system can be corrected with transplantation of an organ from a donor. However, the donor transplants (such as the transplanted organ, tissue or cells), especially in allografts or xenografts, are recognized as foreign agents by the recipient's immune system, thereby causing the rejection of transplanted organs, tissues or cells.

Although there are many antigens involved in the rejection of genetically disparate tissues, those responsible for the most vigorous allograft rejection reactions are the major histocompatibility complex (MHC). In humans, the MHC is called the human leukocyte antigen (HLA) system and is located on the short arm of chromosome 6, near the complement genes. The most studied HLA genes are the nine classical MHC genes: HLA-A, HLA-B, HLA-C, HLA-DPA1, HLA-DPB1, HLA-DQA1, HLA-DQB1, HLA-DRA, and HLA-DRB1. In humans, the MHC gene cluster is divided into three regions: classes I, II, and III. The A, B and C genes belong to MHC class I, whereas the six D genes belong to class II.

The MHC expression is codominant, meaning that both set of inherited alleles are expressed equally on the cell surface. Furthermore, the set of MHC alleles are inherited as haplotypes; hence, a heterozygous individual will have two MHC haplotypes, one from the paternal chromosome and the other from maternal chromosome. Each person carries two alleles of each of the three class-I genes, (HLA-A, HLA-B and HLA-C), and hence can express six different types of MHC-I. In the class-II locus, each person inherits a pair of HLA-DP genes (DPA1 and DPB1), a couple of genes HLA-DQ (DQA1 and DQB1), one gene HLA-DRα (DRA1), and one or more genes HLA-DRβ (DRB1 and DRB3, -4 or -5); accordingly, one heterozygous individual can inherit six or eight functioning class-II alleles, three or more from each parent. The MHC genes are highly polymorphic; many different alleles exist in the different individuals inside a population.

Both MHC class I and MHC class II proteins play a role in transplant rejection. MHC class I are expressed on all nucleated cells; and these class I molecules are responsible for presenting antigenic peptides from within the cell (e.g., self-antigens, antigens from the intracellular viruses, and tumor-associated antigens) to T cells having CD8 receptors, such as alloreactive killer T cells (also known as cytotoxic T lymphocytes (CTLs). Once the T cell receptors (TCRs) of CTLs recognize the transplanted tissue's MHC class I molecules, the CTLs trigger the target cell's programmed cell death by apoptosis. On the other hand, MHC class II normally occurs only on the professional antigen-presenting cells (APCs), such as dendritic cells, activated macrophages, and B cells. The MHC class II present extracellular antigens to CD4 T cells. When memory helper T cells' CD4 receptors bind to the MHC class II molecules expressed on the surfaces of the target cells of the graft tissue, the memory helper T cells' TCRs recognize their target antigen, and subsequently produces clones that, as effector cells, secrete immune signaling molecules (cytokines) in approximately the cytokine balance that had prevailed at the memory helper T cell's priming to memorize the antigen. As the priming event in this instance occurred amid inflammation, the immune memory is pro-inflammatory.

Graft-versus-host disease is a medical complication following the receipt of donor tissue from a genetically different person. GvHD is commonly associated with stem cell or bone marrow transplant but the term also applies to other forms of tissue graft. Immune cells (white blood cells) in the donated tissue (the graft) recognize the recipient (the host) as "foreign;" and then the transplanted immune cells attack the host's body cells.

The T-E molecular design of this invention can be applied for preparing molecular constructs for preventing the rejection of the donor transplant(s).

In the present molecular constructs, the targeting elements are scFv of antibodies specific for an HLA A, B, or C allotype expressed by cells of the donor transplant and not by cells of the patient receiving the transplant. Since there are six genes in the haplotypes of HLA A, B, and C, it is not difficult to find one gene with different allotypes between the donor and the recipient. Many antibodies against HLA allotypes are already available. For example, antibodies specific for HLA A2 and B27 are well known. An antibody specific for Cw1 antigen (corresponding allele: C*01:02) was made. Some antibodies bind to determinants shared by several allotypes, for example, one antibody binds to A11 and A24 and another one to A11, A25, A26, and A66. A panel of antibodies binding to various HLA allotypes may be established by isolating HLA A, B, and C allotype-specific B cells from the peripheral blood of patients receiving transplants and cloning the VH and VL sequences of those B cells by RT-PCR. Similar procedures have been established in preparing antigen-specific human monoclonal antibodies for various viral antigens. A molecular construct with an scFv specific for an HLA allotype can then be chosen for a patient who has received a transplant with a particular haplotype.

The effector elements can be chosen from (1) the ectodomain or extracellular domain of immune checkpoint proteins, such as CTLA-4 and PD-L1, which can inhibit ongoing immune activation, (2) scFv of antibodies specific for CD25, which is expressed by activated T cells, or (3) small molecular immunosuppressive drugs, sirolimus (rapamycin), everolimus, and tacrolimus (FK-506), which have been used broadly for the prevention of transplantation rejection. Sirolimus and everolimus, which inhibit mTOR (mammalian target of rapamycin), and tacrolimus, which inhibits calcineurin, are powerful inhibitors of T cell activity. Fingolimod and derivatives thereof (e.g., fingolimod phosphate) are also examples of suitable immunosuppressants. Anti-CD25, fingolimod, sirolimus, everolimus and tacrolimus, each have a range of its serious side effects due to their potent immunosuppressive effects. It is desirable to shuffle increased proportions of the drug to the transplant and decreased proportions in other parts of the body, especially the blood and lymphoid system.

Sirolimus (m.w. 914.172 daltons) and tacrolimus (m.w. 804.018 daltons) are suitable for the present application, because in most applications, sirolimus or everolimus is used at approximately 2-10 mg per day and tacrolimus is used at approximately 5-15 mg per day. The immunosuppressive drugs cyclosporine (m.w. 1,202.61 daltons) and mycophenolic acid (m.w. 320.34 daltons), which are also used for the prevention of rejection of transplants, are not suitable for use herein, because cyclosporin is used at approximately 150-1,000 mg per day, and mycophenolic acid is used at approximately 800-1,500 mg per day. For a molecular construct with two scFvs as targeting elements and ten sirolimus molecules as effector elements, the weight of the scFv (m.w. 25,000 daltons) is about 6 times of the weight of sirolimus. Thus, for administering 5 mg of sirolimus, it requires 30 mg of scFv, which is feasible. Because the administered sirolimus will be carried to the transplant, a less amount will be required than if the drug is administered without targeting to the transplant.

Since sirolimus, everolimus, and tacrolimus, act on intracellular targets of T cells, they are linked to the multi-arm linker-unit via a reversible bond, which is cleaved off the linker by hydrolysis or by cleavage by tissue proteases present in the targeted tissue. Since the molecular constructs of the present invention are administered intravenously, they can reach the target site in a fast kinetics and hydrolysis en route is not a major problem. Sirolimus, everolimus, and tacrolimus molecules have been synthesized de novo in organic chemistry laboratories. Various conjugating groups, such as sulfhydryl and amine groups can be incorporated to side chains that do not interfere the drug molecules to inhibit their targets. Furthermore, it is not a concern that the linkage to the linker-unit blocks the activity of fingolimod, sirolimus, everolimus and tacrolimus. The immunosuppressors regain activity after they are released. According to embodiments of the present disclosure, some T-E molecules in single linker-units or joint linkers configuration incorporate scFvs specific for an allogeneic HLA A, B, or C antigen (not present in the treated patient) as targeting elements and, sirolimus, everolimus, tacrolimus or scFv specific for CD25 as effector elements.

Fingolimod and fingolimod phosphate can provide as a good candidate for inhibiting the rejection reaction in transplantation. In clinical trials of fingolimod for kidney transplantation, it was not found to be better than other established, standard care. However, if increased concentration of fingolimod can be reached in the transplanted organ, effective immune suppression against host immune response may be achieved in the transplanted organ.

The strategies of targeting of immunosuppressive agents to the transplanted organs may be applied to the treatment of graft-versus-host diseases (GvHD). In patients who receive stem cells, bone marrow transplants, or even tissues or blood transfusions, the immune cells in the transplants recognize the host cells as foreign and mount immune response against the host cells, causing severe damages in the liver, the skin, the mucosa, the gastrointestinal tracts, and other organs and tissues of the recipient.

Immunosuppressive agents, such as sirolimus, everolimus, tacrolimus, fingolimod, or fingolimod phosphate, may be carried to the cells expressing an HLA allele expressed on the graft leukocytes. These targeted cells include T cells, which are mainly responsible for the cytolytic activities observed in GvHD. When the T cells from the graft are inhibited, the GvHD should improve.

Part I Multi-Arm Linkers for Treating Specific Diseases

In various embodiments, the present disclosure provides a multi-arm linker unit for treating transplantation rejection in a subject. According to various embodiments of the present disclosure, the linker unit comprises a center core, a plurality of linking arms, a plurality of first elements, and optionally, a coupling arm and a second element.

The center core can be a peptide core having a pre-defined number of amine (—NH$_2$) groups, before being linked with the linking arms. For example, the peptide core may have two or more lysine (K) resides having an amine (—NH$_2$) group at the side chain.

In the following sections, the structure of the peptide core suitable for use herein is disclosed, followed by a description regarding the functional elements suitable for use to construct the present multi-arm linker, and the uses of such multi-arm linker.

The first aspect of the present disclosure pertains to a linker unit that comprises, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimidyl (NHS) group at one terminus and a functional group (e.g., an NHS, a maleimide, an azide, an alkyne, a tetrazine, or a strained alkyne group) at the other terminus is linked to the K residue of the center core by forming an amide bond between the NHS group of the PEG chain and the amine group of the K residue. In the present disclosure, the PEG chain linked to the K residue is referred to as a linking arm, which has a functional group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be,

GS,

GGS,

GSG,

GGGS, (SEQ ID NO: 1)

GSGS, (SEQ ID NO: 2)

GGSG, (SEQ ID NO: 3)

GSGGS, (SEQ ID NO: 4)

SGGSG, (SEQ ID NO: 5)

GGGGS, (SEQ ID NO: 6)

GGSGGS, (SEQ ID NO: 7)

GGSGGSG, (SEQ ID NO: 8)

SGSGGSGS, (SEQ ID NO: 9)

GSGGSGSGS, (SEQ ID NO: 10)

SGGSGGSGSG, (SEQ ID NO: 11)

GGSGGSGGSGS, (SEQ ID NO: 12)

SGGSGGSGSGGS, (SEQ ID NO: 13)

GGGGSGGSGGGGS, (SEQ ID NO: 14)

GGGSGSGSGSGGGS, or (SEQ ID NO: 15)

SGSGGGGSGGSGSG. (SEQ ID NO: 16)

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

Basically, the filler sequences between lysine residues cover peptides with glycine and serine residues. However, they can alternatively be peptides composed of amino acids excluding one with amine group in its side chain. Those amino acids are predominantly, but not necessarily entirely hydrophilic amino acids. The amino acids are not necessarily naturally occurring amino acids.

According to certain preferred embodiments of the present disclosure, the center core comprises 2-15 units of the sequence of G$_{1-5}$SK. Alternatively, the polypeptide comprises the sequence of (GSK)$_2$-1$_5$; that is, the polypeptide comprises at least two consecutive units of the sequence of GSK. For example, the present center core may comprises the amino acid sequence of the following, Ac-CGGSGGSGGSKGSGSK, (SEQ ID NO: 17)

Ac-CGGSGGSGGSKGSGSKGSK, or (SEQ ID NO: 18)

Ac-CGSKGSKGSKGSKGSKGSKGSKGSKGSKGSK, (SEQ ID NO: 19)

in which Ac represents the acetyl group.

According to certain embodiments of the present disclosure, the center core is a polypeptide that comprises the sequence of $(X_{aa}\text{-K})_n$, in which $X_{aa}$ is a PEGylated amino acid having 2 to 12 repeats of ethylene glycol (EG) unit, and n is an integral from 2 to 15.

As would be appreciated, the lysine residue of the present center core may be substituted with an amino acid, which side chain contains an amine group. For example, an α-amino acid with $(CH_2\text{-})nNH_2$ side chain, where n=1-3 or 5; an α-amino acid with $(CH(OH)\text{-})nCH_2\text{—}NH_2$ side chain, where n=1-5; an α-amino acid with $(CH_2\text{—}CH(OH)\text{-})nCH_2\text{—}NH_2$ side chain, where n=1-3; an α-amino acid with $(CH_2\text{—}CH_2\text{—}O\text{-})nCH_2\text{—}NH_2$ side chain, where n=1-2. These amino acids are not necessarily naturally occurring amino acids.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine. For example, the present center core may have the sequence of, Ac-(GSK)$_{2-7}$-(G$_{2-4}$S)$_{1-8}$-A$^{AH}$,
Ac-A$^{AH}$-(SG$_{2-4}$)$_{1-8}$-(GSK)$_{2-7}$,
Ac-A$^{AH}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-A$^{AH}$
Ac-K-(Xaa$_{2-12}$-K)$_{2-4}$-Xaa$_{2-12}$-A$^{AH}$
Ac-A$^{AH}$-Xaa$_{2-12}$-K-(Xaa$_{2-12}$-K)$_{2-4}$,
Ac-A$^{AH}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-A$^{AH}$ in which Xaa is a PEGylated amino acid having specified repeats of EG unit, Ac represents the acetyl group, and A$^{AH}$ represents the AHA residue.

Exemplary amino acid having an alkyne group includes, but is not limited to, L-homopropargylglycine (L-HPG), D-homopropargylglycine (D-HPG), or beta-homopropargylglycine (β-HPG). In this case, the present center core may have the sequence of, Ac-(GSK)$_{2-7}$-(G$_{2-4}$S)$_{1-8}$-G$^{HP}$,
Ac-G$^{HP}$-(SG$_{2-4}$)$_{1-8}$-(GSK)$_{2-7}$,
Ac-G$^{HP}$-(SG$_{2-4}$)$_{0-7}$-(GSK)$_{2-6}$-(G$_{2-4}$S)$_{1-8}$-C,
Ac-C-(SG$_{2-4}$)$_{0-7}$-(GSK)$_{2-6}$-(G$_{2-4}$S)$_{1-8}$-G$^{HP}$,
Ac-K-(Xaa$_{2-12}$-K)$_{2-4}$-Xaa$_{2-12}$-G$^{HP}$
Ac-G$^{HP}$-Xaa$_{2-12}$-K-(Xaa$_{2-12}$-K)$_{2-4}$,
Ac-G$^{HP}$-Xaa$_{2-12}$-K-(Xaa$_{2-12}$-K)$_{1-3}$-Xaa$_{2-12}$-C, or
Ac-C-Xaa$_{2-12}$-K-(Xaa$_{2-12}$-K)$_{1-3}$-Xaa$_{2-12}$-G$^{HP}$ in which Xaa is a PEGylated amino acid having specified repeats of EG unit, Ac represents the acetyl group, and G$^{HP}$ represents the HPG residue.

It is noted that many of the amino acids containing an azide or alkyne group in their side chains and PEGylated amino acids are available commercially in t-boc (tert-butyloxycarbonyl)- or Fmoc (9-fluorenylmethyloxycarbonyl)-protected forms, which are readily applicable in solid-phase peptide synthesis.

According to some working examples of the present disclosure, the center core may comprise the sequence of, Ac-G$^{HP}$GGSGGSGGSKGSGSK, (SEQ ID NO: 20)

Ac-G$^{HP}$GGSGGSGGSKGSGSKGSK, (SEQ ID NO: 21)

Ac-A$^{AH}$GGSGGSGGSKGSGSKGSK, (SEQ ID NO: 22)

Ac-G$^{HP}$GGSGGSGGSKGSGSKGSGSC, (SEQ ID NO: 23)

Ac-C-Xaa$_2$-K-Xaa$_2$-K-Xaa$_2$-K, (SEQ ID NO: 24)
or

Ac-C-Xaa$_6$-K-Xaa$_6$-K-Xaa$_6$-K-Xaa$_6$-K-Xaa$_6$-K, (SEQ ID NO: 25)

in which Xaa is a PEGylated amino acid having specified repeats of EG unit, Ac represents the acetyl group, A$^{AH}$ represents the AHA residue, and G$^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

As would be appreciated, the cysteine residue of the present center core may be substituted with an amino acid, which side chain contains a sulfhydryl group. For example, an α-amino acid with $(CH(OH)\text{-})nCH_2\text{—}SH$ side chain, where n=1-5; an α-amino acid with $(CH_2\text{—}CH(OH)\text{-})nCH_2\text{—}SH$ side chain, where n=1-3; an α-amino acid with $(CH_2\text{—}CH_2\text{—}O\text{-})nCH_2\text{—}SH$ side chain, where n=1-2. The amino acid is not necessarily naturally occurring amino acids. The cysteine residue need not be placed at the N- or C-terminal of the peptide core. For example, the cysteine residue can be placed in the middle of the peptide, so that the lysine residues are distributed on two sides of the cysteine residue.

Preferably, the coupling arm has a tetrazine group or a strained alkyne group (e.g., a cyclooctene or cyclooctyne group) at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. The strained alkyne group may be a cyclooctene or a cyclooctyne group. According to the working examples of the present disclosure, the cyclooctene group is a trans-cyclooctene (TCO) group; example of cyclooctyne group includes, but is not limited to, dibenzocyclooctyne (DBCO), difluorinated cyclooctyne (DIFO), bicyclononyne (BCN), and dibenzocyclooctyne (DICO). According to some embodiments of the present disclosure, the tetrazine group is 6-methyl-tetrazine.

Example of the present center core configured to be linked with the coupling arm includes, but is not limited to, Ac-(GSK)$_{2-7}$-(G$_{2-4}$S)$_{1-8}$-C-Xaa$_{2-12}$-tetrazine,
Ac-(GSK)$_{2-7}$-(G$_{2-4}$S)$_{1-8}$-C-Xaa$_{2-12}$-strained alkyne,
Ac-K-(Xaa$_{2-12}$-K)$_{2-4}$-Xaa$_{2-12}$-C-Xaa$_{2-12}$-tetrazine,
Ac-K-(Xaa$_{2-12}$-K)$_{2-4}$-Xaa$_{2-12}$-C-Xaa$_{2-12}$-strained alkyne,
Tetrazine-Xaa$_{2-12}$-C(Ac)-(SG$_{2-4}$)$_{1-8}$-(GSK)$_{2-7}$,
Strained alkyne-Xaa$_{2-12}$-C(Ac)-(SG$_{2-4}$)$_{1-8}$-(GSK)$_{2-7}$,
Tetrazine-Xaa$_{2-12}$-C(Ac)-Xaa$_{2-12}$-K-(Xaa$_{2-12}$-K)$_{2-4}$, and
Strained alkyne-Xaa$_{2-12}$-C(Ac)-Xaa$_{2-12}$-K-(Xaa$_{2-12}$-K)$_{2-4}$.

Alternatively, the center core has an azide or alkyne group at one terminus and a coupling arm with tetrazine or strained alkyne group at the other terminus. Examples are the following:

Ac-A$^{AH}$-(SG$_{2-4}$)$_{0-7}$-(GSK)$_{2-6}$-(G$_{2-4}$S)$_{1-8}$-C-Xaa$_{2-12}$-tetrazine,
Ac-A$^{AH}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-A$^{AH}$
Strained alkyne-Xaa$_{2-12}$-C(Ac)-(SG$_{2-4}$)$_{0-7}$-(GSK)$_{2-6}$-(G$_{2-4}$S)$_{1-8}$-A$^{AH}$
Ac-A$^{AH}$-Xaa$_{2-12}$-K-(Xaa$_{2-12}$-K)$_{1-3}$-Xaa$_{2-12}$-C-Xaa$_{2-12}$-tetrazine,
Ac-A$^{AH}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-A$^A$H,
Strained alkyne-Xaa$_{2-12}$-C(Ac)-Xaa$_{2-12}$-K-(Xaa$_{2-12}$-K)$_{1-3}$-Xaa$_{2-12}$-A$^A$H
Ac-G$^{HP}$-(SG$_{2-4}$)$_{0-7}$-(GSK)$_{2-6}$-(G$_{2-4}$S)$_{1-8}$-C-Xaa$_{2-12}$-tetrazine,
Ac-G$^{HP}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-G$^{HP}$
Strained alkyne-Xaa$_{2-12}$-C(AC)-(SG$_{2-4}$)$_{0-7}$-(GSK)$_{2-6}$-(G$_{2-4}$S)$_{1-8}$-G$^{HP}$
Ac-G$^{HP}$-Xaa$_{2-12}$-K-(Xaa$_{2-12}$-K)$_{1-3}$-Xaa$_{2-12}$-C-Xaa$_{2-12}$-tetrazine,
Ac-G$^{HP}$-Xaa$_{2-12}$-K-(Xaa$_{2-12}$-K)$_{1-3}$-Xaa$_{2-12}$-C-Xaa$_{2-12}$-trained alkyne,
Tetrazine-Xaa$_{2-12}$-C(Ac)-Xaa$_{2-12}$-K-(Xaa$_{2-12}$-K)$_{1-3}$-Xaa$_{2-12}$-G$^{HP}$, and
Strained alkyne-Xaa$_{2-12}$-C(Ac)-Xaa$_{2-12}$-K-(Xaa$_{2-12}$-K)$_{1-3}$-Xaa$_{2-12}$-G$^{HP}$ The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. Other than PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center core has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Reference is now made to FIG. 1A. As illustrated, the linker unit 10A comprises a center core 11a comprising one HPG (G$^{HP}$) residue and four lysine (K) residues respectively separated by filler sequences (denoted by the dots throughout the drawings).

The filler sequences between the HPG residue and K residue or between any two K residues may comprise the same or different amino acid sequences. In this example, four linking arms 20a-20d are linked to the lysine residues by forming an amide linkage between the NHS group and the amine group of the lysine residue, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

Figure 1B:
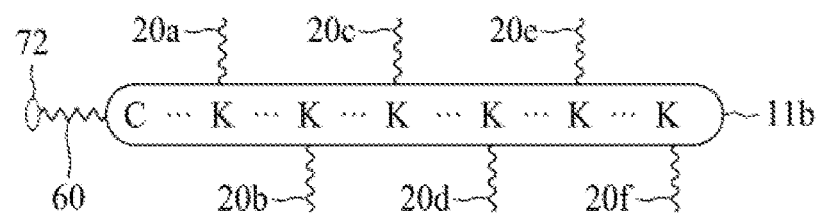

FIG. 1B provides a linker unit 10B according to another embodiment of the present disclosure. The center core 11b comprises one cysteine (C) residue and six lysine (K) residues respectively separated by the filler sequences. In this example, the linker unit 10B comprises six linking arms 20a-20f that are respectively linked to the lysine residues. According to the embodiments of the present disclosure, the linking arm is a PEG chain having 2-20 repeats of EG units.

Unlike the linker unit 10A of FIG. 1A, the linker unit 1B further comprises a coupling arm 60. As discussed above, a PEG chain having a maleimide group at one end and a functional group at the other end is used to form the coupling arm 60. In this way, the coupling arm 60 is linked to the cysteine residue of the center core 11b via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-PEG$_{2-20}$-S—S-maleimide, where S—S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group.

According to the embodiments of the present disclosure, the linking arm linked to the K residue of the center core has a functional group (i.e., a maleimide, an NHS, an azide, an alkyne, a tetrazine, or a strained alkyne group) at its free terminus. Preferably, when the free terminus of the linking arm is an azide, alkyne, or cyclooctyne group, then the amino acid residue at the N- or C-terminus of the center core is a cysteine residue, and the free terminus of the coupling arm is a tetrazine or cyclooctene group. Alternatively, when the free terminus of the linking arm is a tetrazine group or cyclooctene group, then the amino acid residue at the N- or C-terminus of the center core has an azide or alkyne group, or the amino acid residue at the N- or C-terminus of the center core is a cysteine residue, and the free terminus of the coupling arm is an azide, the alkyne, or the cyclooctyne group.

As could be appreciated, the preferred linking arms for this invention are PEG; however, applicable linking arms and coupling arms are not limited to PEG chains. Peptides comprising glycine, serine and other amino acid hydrophilic residues, and polysaccharides, and other biocompatible linear polymers, which are modified to contain NHS and maleimide groups, can be used.

The length of the linking arms is important for several considerations. It should be long enough to allow flexibility of the linked scFv or other types of functional elements to reach targeted antigenic sites on targeted cell surface without steric constraints; yet not long enough to cause intra-molecular and inter-molecular tangling of the linking arms and their linked scFv fragments or functional elements, or to unnecessarily increase the size of the whole molecular construct for hindering tissue penetration. Linking arms that are too long may also fail to pull antigen molecules to form compacted clusters, if such clusters are required to initiate signal-transducing process for apoptosis or other cellular effects. The optimal length of linking arms for different types of combinations of targeted antigens and their binding agents may be determined by any skilled artisan in the related field without undue experimentation. A linking arm of NHS-(PEG)$_{12}$-Maleimide (approximately 500 Daltons) is preferred in a number of molecular construct of this invention. A fully stretched (PEG)$_{12}$ has a length of 40-50 Å.

Depending on the functional group (i.e., a maleimide, an NHS, an azide, an alkyne, a tetrazine, or a strained alkyne group) present at the free terminus of the linking arm, it is feasible to design a functional element (such as, a targeting element, an effector element, or an element for improving the pharmacokinetic property) with a corresponding functional group, so that the functional element may linked to the free terminus of the linking arm via any of the following chemical reactions, (1) forming an amide bond therebetween: in this case, the linking arm has an NHS group at the free terminus, and the functional element has an amine group;

(2) the thiol-maleimide reaction: in this case, the linking arm has a maleimide group at the free terminus, and the functional element has an thiol group;

(3) the Copper(I)-catalyzed alkyne-azide cycloaddition reaction (CuAAC reaction, or the "click" reaction for short): one of the free terminus of the linking arm and the functional element has an azide group, while the other has an alkyne group; the CuAAC reaction is exemplified in Scheme 1;

(4) the inverse electron demand Diels-Alder (iEDDA) reaction: one of the free terminus of the linking arm and the functional element has a tetrazine group, while the other has a cyclooctene group; the iEDDA reaction is exemplified in Scheme 2; or (5) the strained-promoted azide-alkyne click chemistry (SPAAC) reaction: one of the free terminus of the linking arm and the functional element has an azide group, while the other has an cyclooctyne group; the SPAAC reaction is exemplified in Scheme 3.

The CuAAC reaction yields 1,5 di-substituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

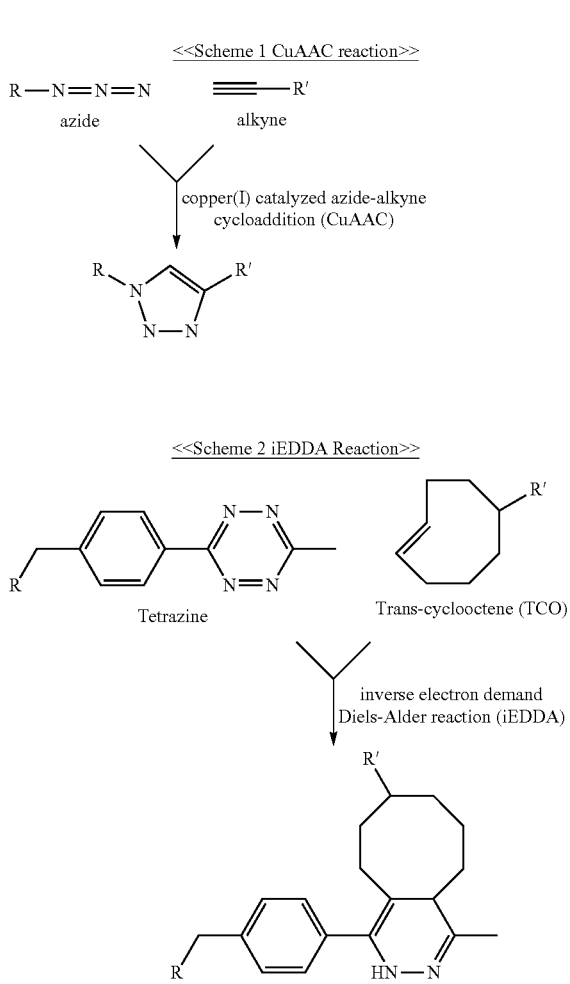

<<Scheme 3 SPAAC reaction>>

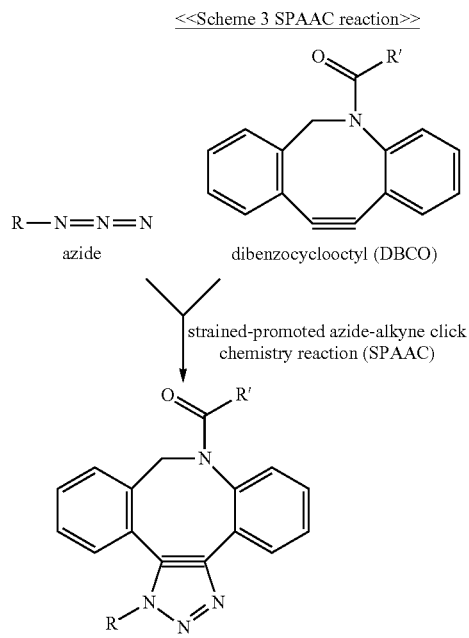

For the sake of illustration, the functional elements linked to the linking arms are referred to as the first elements. As could be appreciated, the number of the first elements carried by the present linker unit depends on the number of K residues of the center core (and thus, the number of the linking arms). Accordingly, one of ordinary skill in the art may adjust the number of the first elements of the linker unit as necessary, for example, to achieve the desired targeting or therapeutic effect.

Figure 1C:
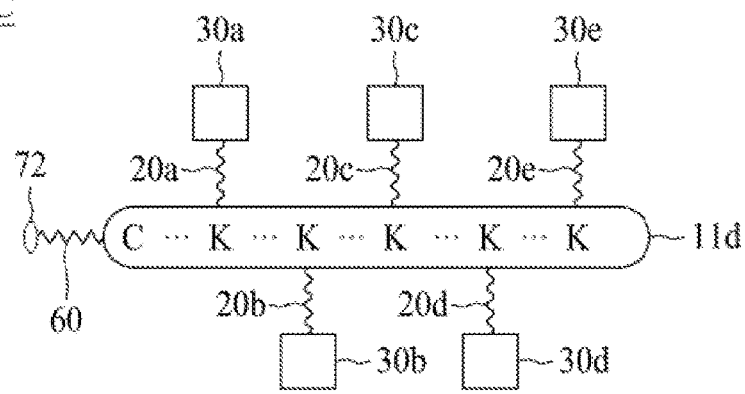

An example of a linker unit 10C having the first elements is illustrated FIG. 1C. Other than the features discussed hereafter, FIG. 1C is quite similar to FIG. 1B. First, there are five K residues in the center core 11d, and accordingly, five linking arms 20a-20e are linked thereto, respectively. Second, the linker unit 10C has five first elements 30a-30e linked to each of the linking arms 20a-20e. As discussed below, the optional tetrazine group 72 allows for the conjugation with an additional functional element, another molecular construct (see, Part II or Part III below).

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability. The choice of a particular first element and/or second element depends on the intended application in which the present linker unit (or multi-arm linker) is to be used. Examples of these functional elements are discussed below in Part I-(iii) of this specification.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the CuAAC reaction.

Figure 1D:
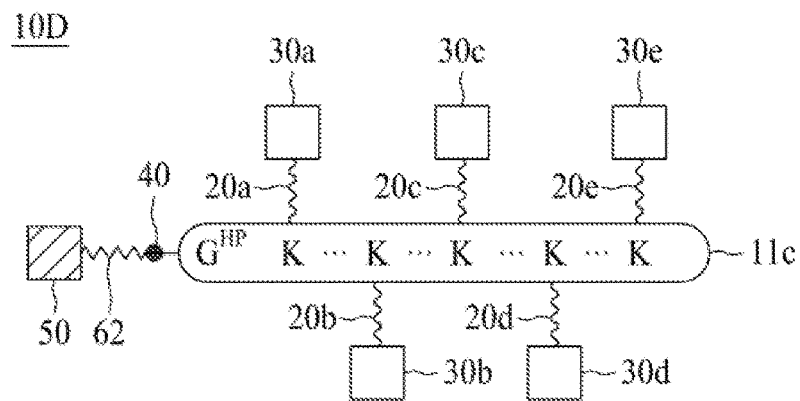

FIG. 1D provides an example of the present linker unit 10D carrying a plurality of first elements and one second element. In this example, the center core 11c comprises one HPG ($G^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10D further comprises one second element 50 that is linked to one end of a short PEG chain 62. Before being conjugated with the center core 11c, the other end of the short PEG chain 62 has an azide group. In this way, the azide group may react with the HPG residue that having an alkyne group via CuAAC reaction, so that the second element 50 is linked to the center core 11c. The solid dot 40 depicted in FIG. 1D represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the iEDDA reaction. According to other embodiments of the present disclosure, the coupling arm has a TCO group, which is capable of being linked to a second element having a tetrazine group via the iEDDA reaction. In the iEDDA reaction, the strained cyclooctene that possess remarkably decreased activation energy in contrast to terminal alkynes is employed, and thus eliminates the need of an exogenous catalyst.

Figure 1E:
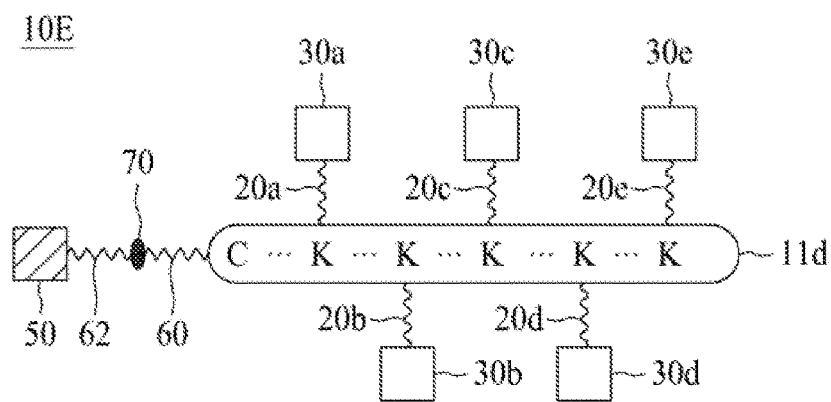

Reference is now made to FIG. 1E, in which the center core 11d of the linker unit 10E comprises a terminal cysteine (C) residue and five lysine (K) residues. As depicted in FIG. 1E, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a second element 50 linked with a short PEG chain 62 having a corresponding TCO or tetrazine group can be linked to the coupling arm 60 via the iEDDA reaction. The ellipse 70 as depicted in FIG. 1E represents the chemical bond resulted from the iEDDA reaction occurred between the coupling arm 60 and the short PEG chain 62.

According to other embodiments of the present disclosure, before the conjugation with a second element, the coupling arm has an azide group. As such, the coupling arm can be linked to the second element having a strained alkyne group (e.g., the DBCO, DIFO, BCN, or DICO group) at the free-terminus of a short PEG chain via SPAAC reaction (see, scheme 3), and vice versa.

Figure 1F:
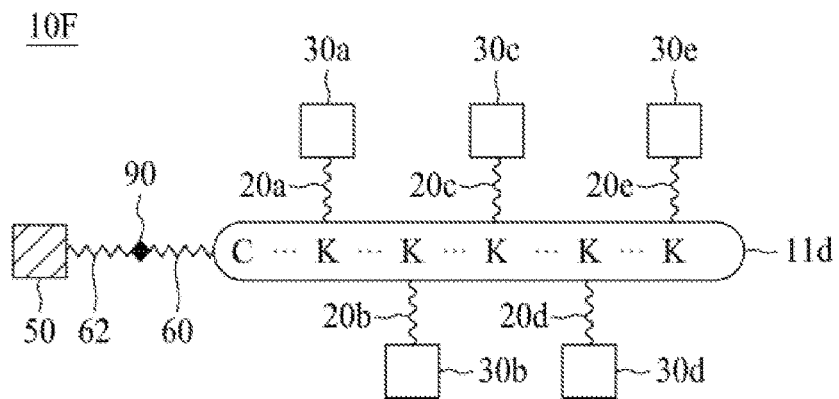

Reference is now made to FIG. 1F, in which the linker unit 10F has a structure similar to the linker unit 10E of FIG. 1E, except that the coupling arm 60 comprises an azide or a strained alkyne group (e.g., the DBCO, DIFO, BCN, or DICO group), instead of the tetrazine or TCO group. Accordingly, the second element 50 linked with a short PEG chain 62 may have a corresponding strained alkyne (e.g., DBCO, DIFO, BCN, or DICO) or azide group, so that it can be linked to the coupling arm 60 via the SPAAC reaction. The diamond 90 as depicted in FIG. 1F represents the chemical bond resulted from the SPAAC reaction occurred between the coupling arm 60 and the short PEG chain 62.

Scheme 4 is an exemplary illustration of the process of preparing the present linker unit. In step 1, the center core comprising the amino acid sequence of (GSK)$_3$ and a L-azidohomoalanine (AHA) residue at the C-terminus thereof is prepared. In step 2, three linking arms are respectively linked to the lysine (K) residues of the center core via forming an amide bond between the NHS group and the amine group; the linking arm linked to the center core has a maleimide (Mal) group at the free-terminus thereof. In step 3, three anti-A antigen scFvs (scFv α A) as the first element are respectively linked to the linking arms via the thiol-maleimide reaction. Meanwhile, in step 4, one anti-B antigen scFv (scFv α B) as the second element is linked with a short PEG chain that has 4 repeats of EG units and a DBCO group at the free terminus. Finally, in step 5, the second element is linked to the AHA residue of the center core via the SPAAC reaction.

<<Scheme 4 Preparation of linker unit linked with two different scFvs via linking arm and C-terminal amino acid residue>>

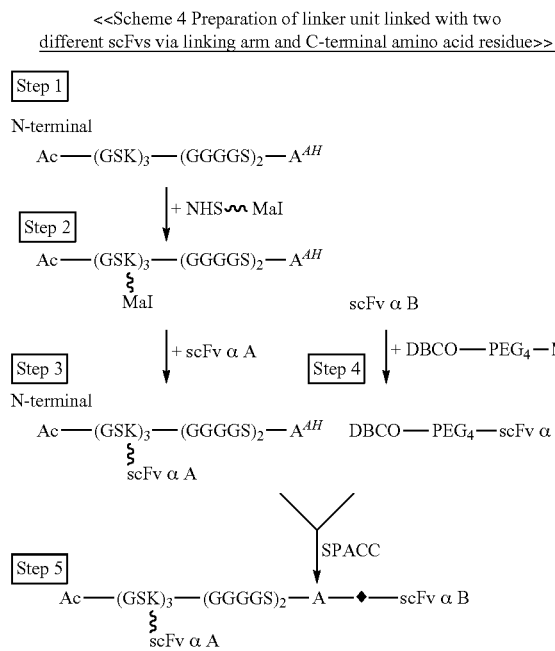

Scheme 5 illustrates another example of the process for preparing the present linker unit. In step 1, the center core comprising the amino acid sequence of (K-Xaa)$_3$ and a cysteine residue at the C-terminus thereof is prepared. In step 2, a PEG chain (as the coupling arm) that has the maleimide (Mal) group at one terminus and a tetrazine group at the other terminus is linked to the cysteine residue via the thiol-maleimide reaction. Then, in step 3, three linking arm are respectively linked to the lysine (K) residues of the center core. Next, three anti-A antigen scFvs (scFv α A) as the first elements are respectively linked to the linking arms via the thiol-maleimide reaction as described in step 4. Meanwhile, in step 5, one anti-B antigen scFv (scFv α B) as the second element is linked with a short PEG chain that has 3 repeats of EG units and a TCO group at the free terminus. Finally, in step 6, the second element is linked to the coupling arm via the iEDDA reaction.

<<Scheme 5 Preparation of linker unit linked with two different scFvs via linking arm and coupling arm>>

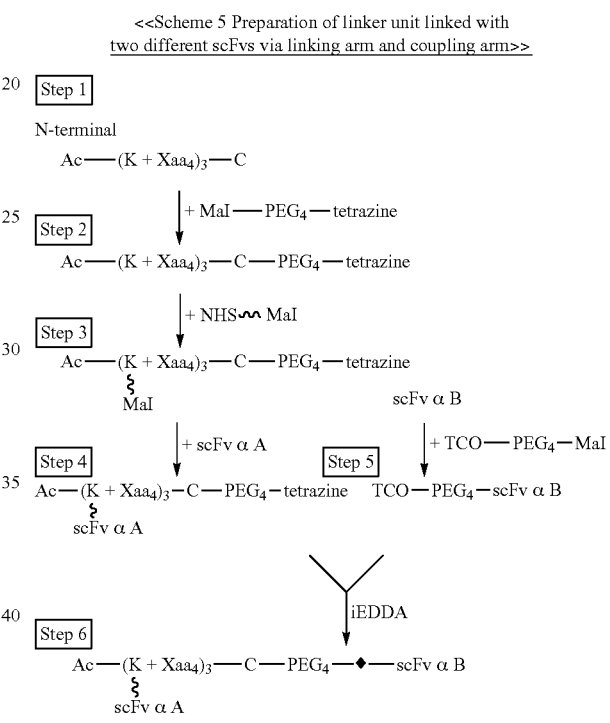

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 Daltons.

Figure 1G:
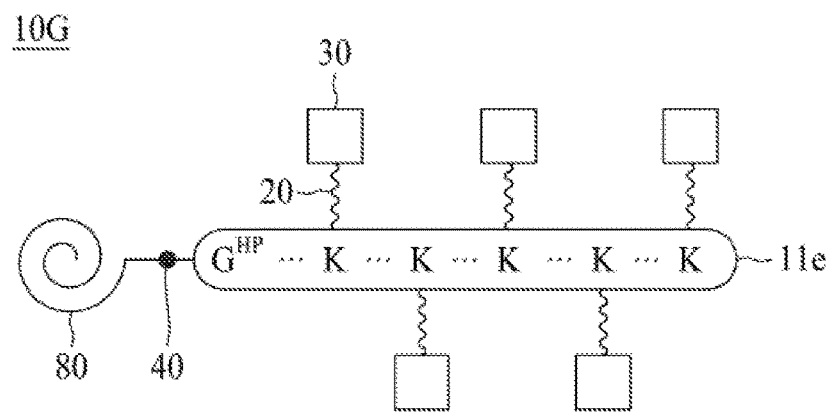

FIG. 1G provides an alternative example of the present linker unit (linker unit 10G), in which five first elements 30 are respectively linked to the lysine residues via the linking arms 20, and the HPG (G$^{HP}$) residue of the center core Ile is linked with a PEG chain 80 via the CuAAC reaction. The solid dot 40 depicted in FIG. 1G represents the chemical bond resulted from the CuAAC reaction occurred between the HPG residue and the PEG chain 80.

Figure 1H:
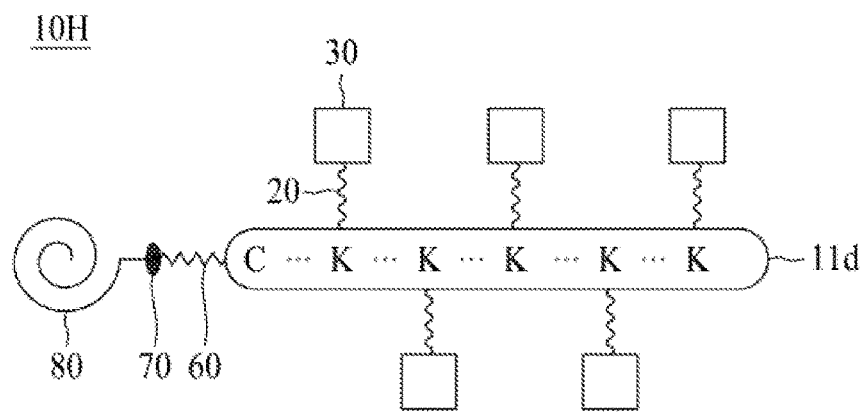

FIG. 1H provides another example of the present disclosure, in which the N-terminus of the center core 11d is a cysteine residue that is linked to a coupling arm 60. A PEG chain 80 can be efficiently linked to the coupling arm 60 via the iEDDA reaction. The ellipse 70 of the linker unit 10H represents the chemical bond resulted from the iEDDA reaction occurred between the coupling arm 60 and the PEG chain 80.

Figure 1I:
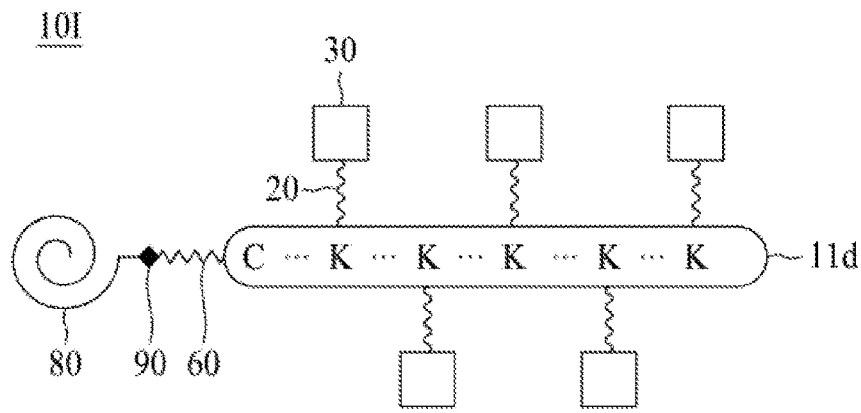

FIG. 1I provides an alternative example of the present linker unit, in which the linker unit 10I has a structure similar to the linker unit 10G of FIG. 1G, except that the PEG chain 80 is linked to the coupling arm 60 via the SPAAC reaction. The diamond 90 depicted in FIG. 1I represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Figure 1J:
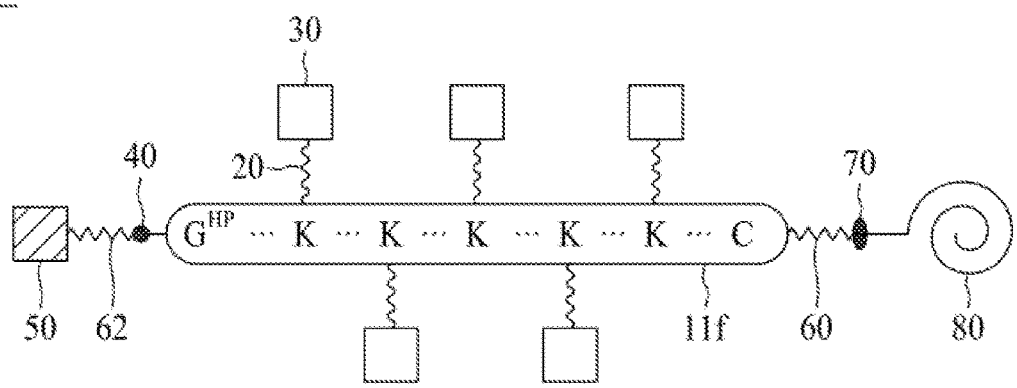

Reference is now made to the linker unit 10J of FIG. 1J, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60, and the third element 50 is linked to the HPG residue via the short PEG chain 62. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 1K:
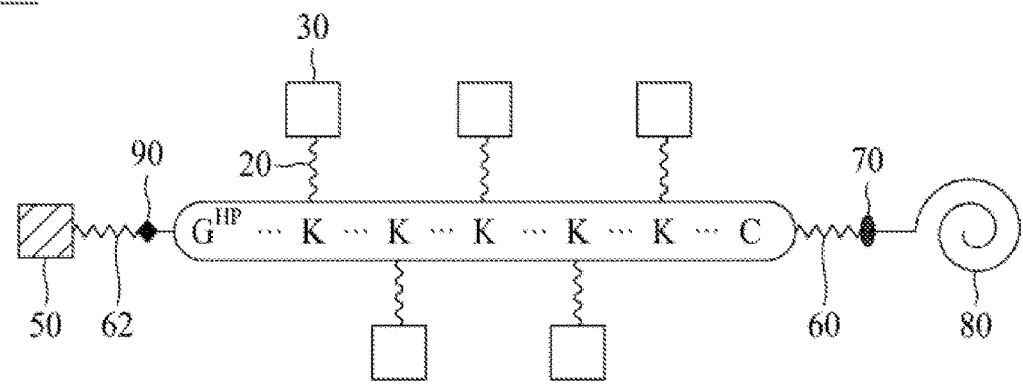

FIG. 1K provides another embodiment of the present disclosure, in which the linker unit 10K has the similar structure with the linker unit 10J of FIG. 1J, except that the short PEG chain 62 is linked with the HPG residue via the SPAAC reaction, instead of the iEDDA reaction. The diamond 90 in FIG. 1K represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a plural of second elements.

In the case where the linker unit (or multi-arm linker) comprises only the first element but not the second and/or third element(s), the first element is an effector element that may elicit a therapeutic effect in a subject. On the other hand, when the present linker unit comprises elements in addition to first element(s), then at least one of the elements is an effector element, while the other may be another effector element, a targeting element, or an element capable of enhancing one or more pharmacokinetic properties of the linker unit (e.g., solubility, clearance, half-life, and bioavailability). For example, the linker unit may have two different kinds of effector element, one effector element and one targeting element or one pharmacokinetic property-enhancing element, two different kinds of targeting elements and one kind of effector element, two different kinds of effector elements and one kind of targeting element, or one kind of targeting element, one kind of effector element and one element capable of improving the pharmacokinetic property of the linker unit.

According to some embodiments of the present disclosure, the targeting element is an antibody fragment specific for a human leukocyte antigen (HLA) allotype present only on cells of the donor transplant and not on cells of the recipient, such as the HLA-A, HLA-B, and HLA-C allotype.

Also, the effector element according to embodiments of the present disclosure is an immunosuppressant, an immune checkpoint protein, or an antibody fragment specific for CD25. Illustrative examples of immunosuppressant are inhibitors of mammalian target of rapamycin (mTOR), e.g. sirolimus and everolimus. Another set of immunosuppressants are inhibitors of calcineurin, e.g. tacrolimus. Immune checkpoint proteins are those involve in immune checkpoint, such as the extracellular domain of cytotoxic T lymphocyte associated protein 4 (CTLA-4, also known as CD151) and the extracellular domain of programmed death-ligand 1 (PD-L1, also known as CD274).

The present disclosure also pertains to method for treating transplantation rejection in a subject receiving a donor transplant or tissue, or cells using the suitable multi-arm linker. Generally, the method comprises the step of administering to a subject in need of such treatment an effective amount of the multi-arm linker according to embodiments of the present disclosure.

Compared with previously known therapeutic constructs, the present multi-arm linker (or linker unit) discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ, one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described above, the number of the first element may vary with the number of lysine residue comprised in the center core. If the number of lysine residue in the center core ranges from 2 to 15, then at least two first elements may be comprised in each linker unit. Thus, instead of providing one single molecule (e.g., immunosuppressant drug and antibody) as traditional therapeutic construct or method may render, the present linker unit is capable of providing more functional elements (either as targeting elements or as effector elements) at one time, thereby greatly improves the therapeutic effect.

In certain therapeutic applications, it is desirable to have a single copy of a targeting or effector element. For example, a single copy of a targeting element can be used to avoid unwanted effects due to overly tight binding. This consideration is relevant, when the scFv has a relatively high affinity for the targeted antigen and when the targeted antigen is a cell surface antigen on normal cells, which are not targeted diseased cells. In still another example, it is desirable to have only one copy of long-chain PEG for enhancing pharmacokinetic properties. Two or more long PEG chains may cause tangling and affect the binding properties of the targeting or effector elements.

PART II Fc-Based Molecular Constructs for Treating Transplantation Rejection and Uses Thereof In the broad sense of the Fc-based configuration, immunoglobulin antibody can serve as the base of a targeting or effector element, and its corresponding effector or targeting element can be incorporated at the C-terminal of its two heavy γ chains in the form of scFv domains. For a typical "Fc-based" configuration, two-chain IgG.Fc is used as the base of the molecular platform. Each of the polypeptide chain is fused with one or two targeting and one or two effector elements, for a total of two to three elements on each chain. The T-E molecule with an Fc-based configuration will have a total of four to six elements (e.g., scFv, proteins, or drug bundles). Optionally, the Fc portion of the molecular constructs also carries Fc-mediated effector functions, ADCC, and/or complement-mediated activation. While in certain other applications, such Fc-mediated effector functions are avoided.

By selecting the T-E elements of the present Fc-based molecular construct, the molecular construct can be used to prevent and/or treat conditions associated with transplantation rejection. The present disclosure is also advantageous in that, in some embodiments, it utilizes the linker unit proposed in the present disclosure, which provides a facile means for controlling the number of the targeting and effector elements of the present Fc-based molecular constructs. Depending on the targeting and/or effector elements selected, the present Fc-based molecular construct may take different configurations, which are discussed below, respectively.

In many molecular constructs of this invention, the preferred targeting or effector elements are Fab, Fv, single-chain Fv (scFv), single-domain antibody (sdAb), or other antigen-binding fragments of antibodies. For the scFv, a polypeptide linker with a sequence of $(GGGGS)_{2-5}$ is placed between $V_L$ and $V_H$, or between $V_H$ and $V_L$, according to certain preferred embodiments Other sequences of flexible nature and without a rigid secondary structure, such as the linking sequences between CH1 and CH2 domains and CH2 and CH3 domains of some human immunoglobulin isotypes, may also be used. In some optional embodiments, a polypeptide linker of $(GGGGS)_{1-3}$ and a terminal cysteine residue is configured at the C-terminal of the scFv or other antibody fragment or therapeutic peptide. The sulfhydryl group is for conjugating with a maleimide group at the end of the linking arms extending from a linker unit.

In a first series of Fc-based molecular constructs, the targeting element can be an antibody (or a fragment thereof) specific for an HLA allotype, and the elector element can be an antibody (or an antibody fragment) specific for CD25. Some illustrative structures of this Fc-based molecular construct are discussed below.

Figure 2B:
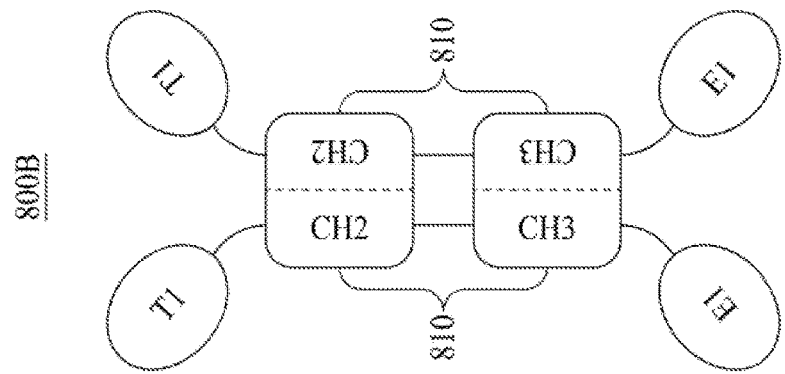
FIGS. 2A to 2C are schematic diagrams illustrating Fc-based molecular constructs according to various embodiments of the present disclosure.
Figure 2A:
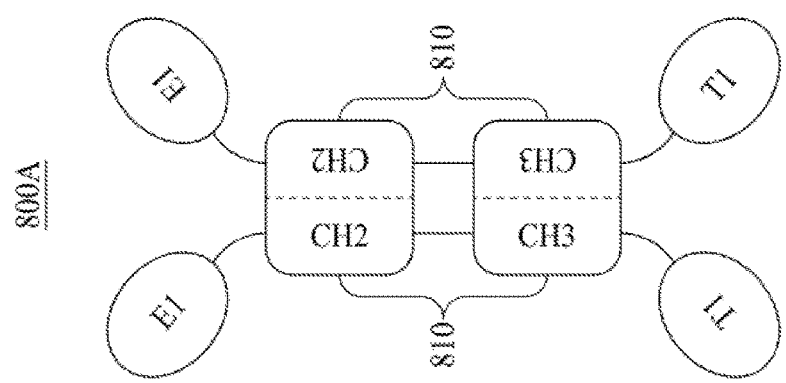

Referring to FIG. 2A, which is a schematic diagram illustrating an Fc-based molecular construct 800A according to certain embodiments of the present disclosure. As illustrated, the Fc-based molecular construct 800A comprises two identical CH2-CH3 chains 810, a first pair of effector elements E1 (e.g., scFvs specific for CD25) linked to the N-termini of the CH2-CH3 chains 810, and a first pair of targeting elements T1 (e.g., scFvs specific for an HLA allotype) linked to the C-termini of the CH2-CH3 chains 810.

The Fc-based molecular construct 800B illustrated in FIG. 2B is quite similar to the Fc-based molecular construct 800A of FIG. 2A in structure, except that the two effector elements E1 are respectively linked to the C-termini of the CH2-CH3 chains 810, while the two targeting elements T1 are respectively linked to the N-termini of the CH2-CH3 chains 810.

Figure 2C:
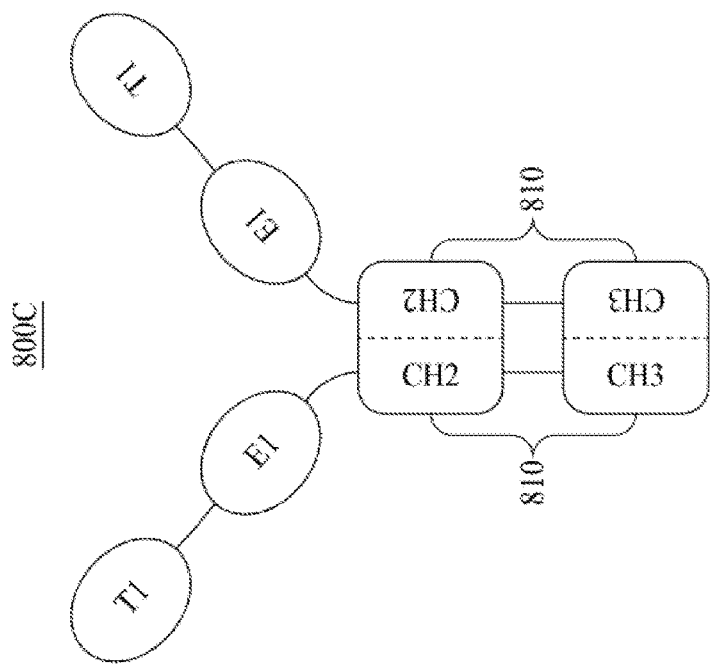

According to certain embodiments, both the effector elements and targeting elements are linked to the N-termini of the CH2-CH3 chains. For example, when both the effector element and the targeting element are in the form of single-chain variable fragments (scFvs), the effector element and the targeting element may be linked in a tandem or diabody configuration, thereby forming a bispecific scFv that is linked to the N-terminus of the CH2-CH3 chain. The Fc-based molecular construct 800C (FIG. 2C) comprises an Fc portion, and each CH2-CH3 chain 810 has a T1-E1 bispecific scFv linked to the N-terminus thereof.

Figure 3:
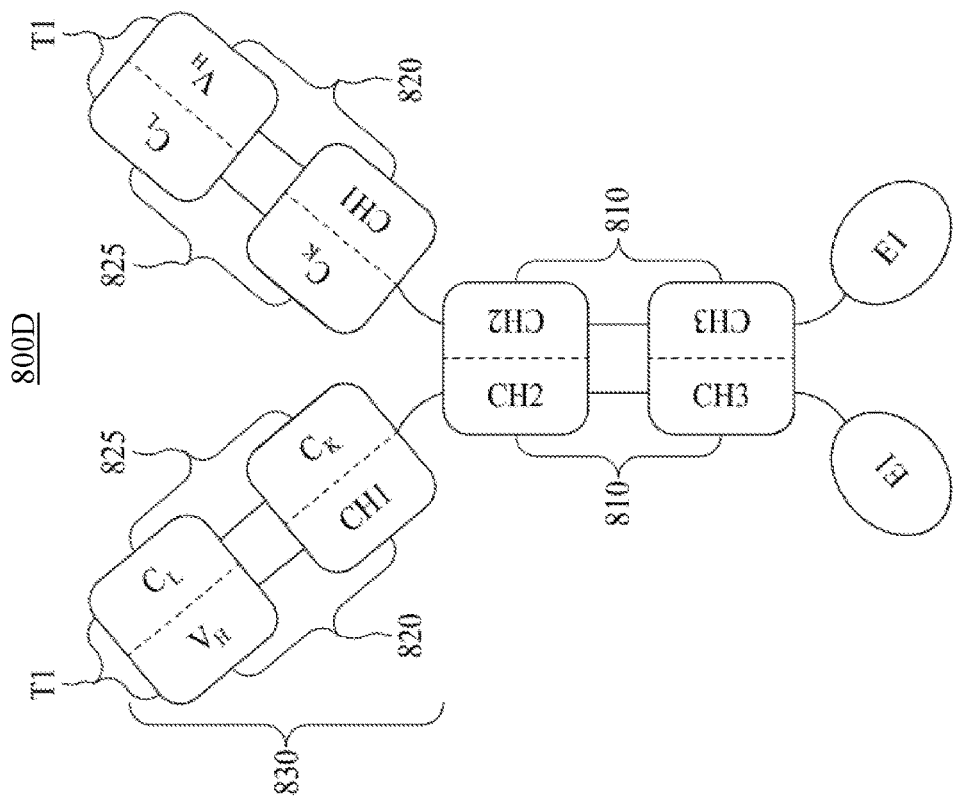
FIG. 3 is a schematic diagram illustrating a Fc-based molecular construct according to some embodiments of the present disclosure.

In some examples, the first pair of effector elements or the first pair of the targeting elements takes a Fab configuration (i.e., consisting of the $V_H$-CH1 domain and the $V_L$-$C_K$ domain); this Fab fragment is linked to the N-termini of the CH2-CH3 chains, so that the Fc-based molecular construct adopts an IgG configuration. In these cases, the pair of elements that is not in the Fab configuration may be linked to the C-termini of the pair of CH2-CH3 segments. For example, in the Fc-based molecular construct 800D of FIG. 3, each of the two targeting elements T1 comprises the $V_H$-CH1 domain 820 and the $V_L$-$C_K$ domain 825, thereby forming a Fab configuration 830 that is linked to the N-termini of the CH2-CH3 chains 810, so that the Fc-based molecular construct 800D adopts the IgG configuration. In this case, the pair of effector elements E1 is linked to the C-termini of the pair of CH2-CH3 chains 810.

As described above, the present Fc-based molecular construct may carry a total of six elements at most. The additional elements may be a second pair of effector elements or a second pair of targeting elements.

In a second series of Fc-based molecular constructs, the targeting element is an antibody or a fragment thereof (e.g., an scFv specific for an HLA allotype), whereas the effector element is a protein or peptide (e.g., an immune checkpoint protein or a fragment thereof).

Figure 4B:
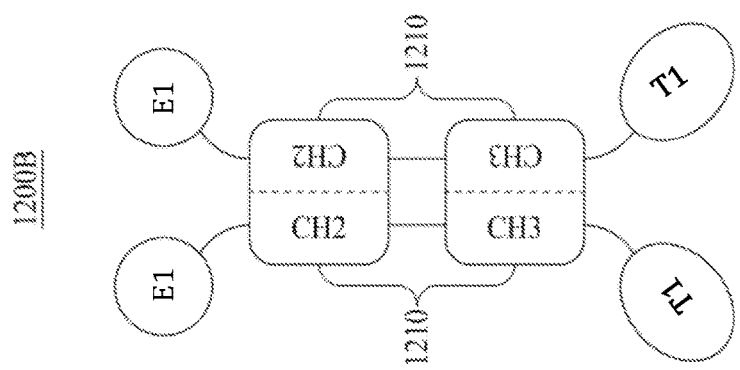
FIGS. 4A to 4C are schematic diagrams illustrating Fc-based molecular constructs according to various embodiments of the present disclosure.
Figure 4A:
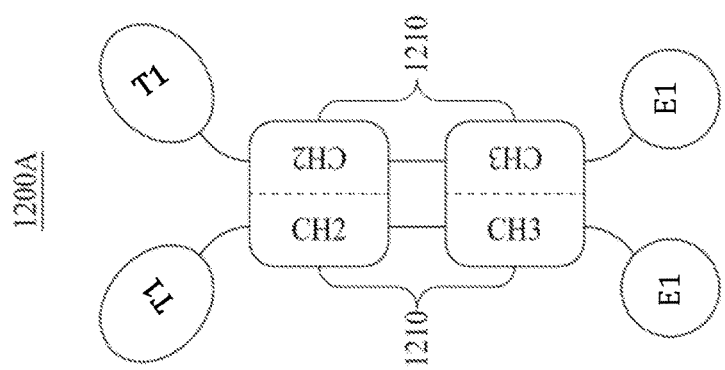

Referring to FIG. 4A, which is a schematic diagram illustrating an Fc-based molecular construct 1200A comprises a pair of targeting elements T1 (as scFvs) linked to the N-termini of the pair of CH2-CH3 segments 1210, and a pair of effector elements E1 (in the form of therapeutic peptides) linked to the C-termini of the pair of CH2-CH3 segments 1210. Alternatively, in the Fc-based molecular construct 1200B of FIG. 4B, the pair of targeting elements T1 (as scFvs) is linked to the C-termini of the pair of CH2-CH3 segments 1210, whereas the pair of effector elements E1 (in the form of therapeutic peptides) is linked to the N-termini of the pair of CH2-CH3 segments 1210.

In some embodiments, the pair of the targeting elements takes a Fab configuration (i.e., consisting of the $V_H$-CH1 domain and the $V_L$-$C_K$ domain); this Fab fragment is linked to the N-termini of the CH2-CH3 chains, so that the Fc-based molecular construct adopts an IgG configuration. In these cases, the pair of effector elements may be linked to the C-termini of the pair of CH2-CH3 segments.

Figure 4C:
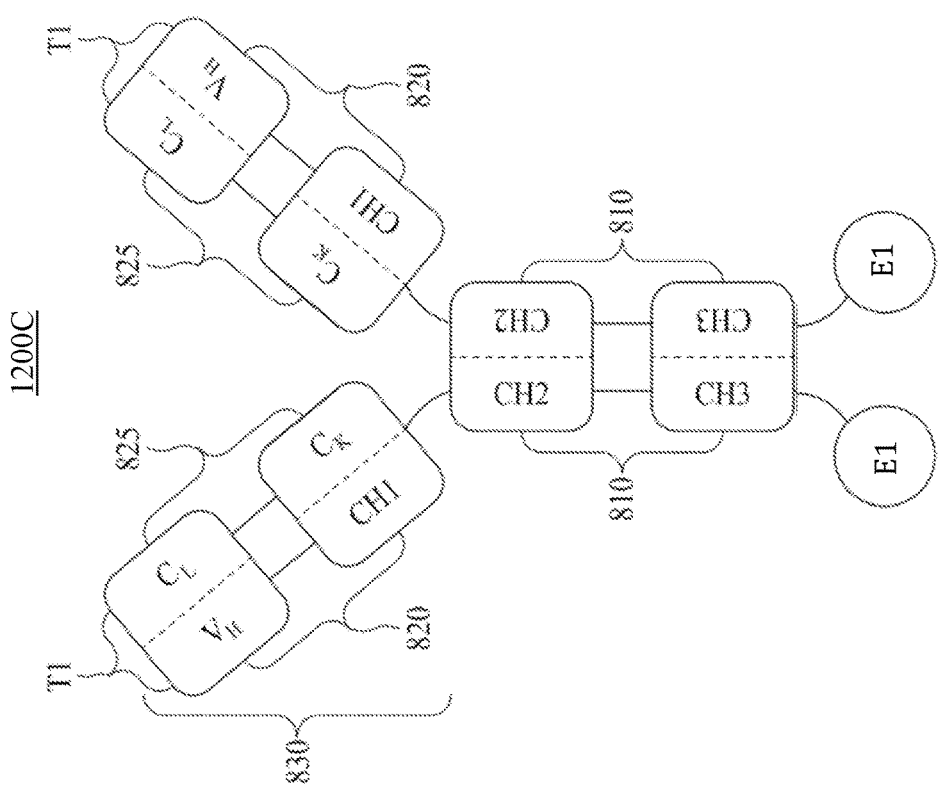

For example, in the Fc-based molecular construct 1200C of FIG. 4C, each of the two targeting elements T1 comprises the $V_H$-CH1 domain 820 and the $V_L$-$C_K$ domain 825, thereby forming a Fab configuration 830 that is linked to the N-termini of the CH2-CH3 chains 810, so that the Fc-based molecular construct 1200C adopts the IgG configuration. In this case, the pair of effector elements E1 (a therapeutic peptide) is linked to the C-termini of the pair of CH2-CH3 chains 810.

In a third series of Fc-based molecular constructs, the targeting element can be an antibody or a fragment thereof, and the elector element can be a drug bundle comprising a plurality of immunosuppressant molecules.

In these cases, the Fc-based molecular constructs for treating diseased cells may have the configuration of molecular construct 1000A of FIG. 5A or molecular construct 1000B of FIG. 5B. As illustrated in FIG. 5A, the effector elements E1 (for example, drug bundles) are linked to the C-termini of the pair of CH2-CH3 segments 1010, whereas the targeting elements T1 (in this case, an scFv) are linked to the N-termini of the pair of CH2-CH3 segments 1010. According to alternative embodiments, the molecular construct 1000B (see, FIG. 5B) has a pair of targeting elements T1 that takes the form of a Fab 1030. Specifically, the Fab 1030 configuration comprises the $V_H$-CH1 domain 1020 and the $V_L$-$C_K$ domain 1025, and is linked to the N-termini of the pair of CH2-CH3 segments 1010, so that the Fc-based molecular construct 1000A adopts the IgG configuration. In this case, the pair of effector elements E1 is linked to the C-termini of the pair of CH2-CH3 chains 1010.

As could be appreciated, the drug bundle (i.e., effector element E1) may be provided as the linker unit discussed in the present disclosure (see, for example FIG. 1A to FIG. 1C). According to the principles and spirits of the present disclosure, a targeting construct (comprising the pair of CH2-CH3 segments 1010 and the targeting elements T1) and the drug bundles (for use as effector elements E1) can be prepared separately and then conjugated with each other.

In either series according to embodiments of the present disclosure, the CH2-CH3 chains are adopted from human immunoglobulins γ1 or γ4. In general, γ1 is chosen, when Fc-mediated functions, such as antibody-dependent cellular cytotoxicity (ADCC) and complement-mediated activity (inflammatory activation or target cell lysis), are desired. In the case where Fc-mediated functions are avoided, γ4 is chosen for constructing the present Fc-based molecular constructs.

According to embodiments of the present disclosure, the drug bundle comprises a center core, a plurality of linking arms, and optionally, a coupling arm. The center core may be a polypeptide comprising a plurality of lysine (K) residues, according to various embodiments of the present disclosure. Each of the linking arms has one terminus that is linked to the center core by reacting with the amine side chain of the K residues of the polypeptide core. The linking arm also carries a maleimide group at the free terminus thereof, wherein each of the drug molecules is linked to the center core via connecting through the linking arm by reacting with the maleimide group. According to optional embodiments of the present disclosure, each of the effector elements E1 is a drug bundle with 3-5 immunosuppressant molecules.

In the case where the center core is the polypeptide core, then the amino acid residue at the N- or C-terminus of the center core is a cysteine residue or has an azide group or an alkyne group. According to certain embodiments, for polypeptide cores with a terminal amino acid residue having the azide group, the drug bundle is linked to the peptide extension via the SPAAC reaction or CuAAC reaction occurred between said terminal residue and the C-terminus of the peptide extension. Alternatively, when the polypeptide cores has a terminal amino acid residue with the alkyne group, the drug bundle is linked to the peptide extension via the CuAAC reaction occurred between said terminal residue and the C-terminus of the peptide extension. Still alternatively, for polypeptide cores with a terminal residue that is cysteine, the drug bundle further comprises said coupling arm. Specifically, the coupling arm has one terminus linked to the center core by reacting with the cysteine residue of the polypeptide core. The coupling arm also carries an alkyne group, azide group, tetrazine group, or strained alkyne group at the free terminus thereof, so that the drug bundle is linked to the C-terminus of the peptide extension via the iEDDA reaction (for coupling arms with the tetrazine or cyclooctene group), SPAAC (for coupling arms with the azide or cyclooctyne group) reaction or CuAAC reaction (for coupling arms with the alkyne or azide group) occurred therebetween.

According to certain embodiments, the present Fc-based molecular construct for treating diseased cells further comprises a pair of peptide extensions 1050 (see, FIGS. 10A and 10B) respectively having the sequence of $(G_{2-4}S)_{2-8}C$. As illustrated, the pair of peptide extensions 1050 is linked to the C-termini of the pair of CH2-CH3 segments 1010. The cysteine residue at the C-terminus of the peptide extension is linked with a coupling arm 1055 via thiol-maleimide reaction occurred therebetween. Also, before being conjugated with the effector element E1 (in this case, a drug bundle), the free terminus of the conjugating arm (that is, the terminus that is not linked to the cysteine residue) is modified with an alkyne, azide, strained alkyne, or tetrazine group, so that the drug bundle is linked thereto via iEDDA reaction (see, FIG. 5A), SPAAC (see, FIG. 5B), or CUAAC (not shown) reaction occurred therebetween.

For example, in FIG. 5A, the coupling arm 1040 of the effector element E1 (in this case, a drug bundle) is linked to the CH2-CH3 segment 1010 via iEDDA reaction. The ellipse 1045 as depicted in FIG. 5A represents the chemical bond resulted from the iEDDA reaction occurred between the peptide extension 1050 and the effector element E1. As could be appreciated, an iEDDA reaction is occurred between a tetrazine group and a cyclooctene group, such as a transcyclooctene (TCO) group.

Alternatively, in FIG. 5B, the effector element E1 is linked to the CH2-CH3 segment 1010 via SPAAC reaction. The diamond 1045 as depicted in FIG. 5B represents the chemical bond resulted from the SPAAC reaction occurred between the peptide extension 1050 and the effector element E1. Specifically, an SPAAC reaction is occurred between an azide group and a strained alkyne group (e.g., a cyclooctyne group, including, dibenzocyclooctyne (DBCO), difluorinated cyclooctyne (DIFO), bicyclononyne (BCN), and dibenzocyclooctyne (DICO) group).

In a third series of Fc-based molecular constructs, one of the targeting and effector elements can be a peptide.

As could be appreciated, the discussions above regarding the Fc region and drug bundle of the Fc-based molecular constructs are also applicable here, and hence, detailed description regarding the same is omitted herein for the sake of brevity.

According to the embodiments of the present disclosure, there is ample flexibility in the numbers of targeting elements and effector elements that can be installed, allowing higher targeting specificity and effector activity. The linker units for a targeting element and for an effector element can be prepared separately before joining. In preparing ADCs, the bundles of immunosuppressant can be prepared separately without exposing the antibodies to harsh chemical conditions. In using this approach, the drug to antibody ratios (DAR) can be better controlled than if the drugs are conjugated directly onto antibody molecules. The adoption of the Fc-based molecular construct and drug bindle can accommodate the preparation of various targeting/effector pharmaceutical molecules. Another advantage is that IgG.Fc is not contained in the molecular constructs and can minimize potential Fc-mediated effects, such as complement-mediated activation, when such effects are not desired.

Now that the basic structural arrangements of the Fc-based molecular constructs have been discussed above, certain combinations of particular effector element(s) and targeting element(s) are provided below for the illustration purpose.

In constructing Fc-based molecular constructs for preventing and/or treating diseases/conditions associated with transplantation rejection in a subject (recipient) receiving a donor transplant (e.g., an organ, a tissue, or cells), one may use an antibody (or a fragment thereof) specific for an HLA allotype that is present only on cells of the donor transplant and not on cells of the recipient as the targeting element.

Regarding the effector element for treating transplantation rejection, it can be an immune checkpoint protein, an antibody fragment specific for CD25, or a drug bundle comprising as plurality of immunosuppressant molecules. Immune checkpoint proteins are those involve in immune checkpoint, such as the extracellular domain of cytotoxic T lymphocyte associated protein 4 (CTLA-4, also known as CD151) and the extracellular domain of programmed death-ligand 1 (PD-L1, also known as CD274). Illustrative examples of immunosuppressant are inhibitors of mammalian target of rapamycin (mTOR), e.g. sirolimus and everolimus. Another set of immunosuppressants are inhibitors of calcineurin, e.g. tacrolimus. Fingolimod and derivatives thereof (e.g., fingolimod phosphate) are also examples of suitable immunosuppressants.

The essence of this invention is the rationalization and conception of the specific combination or pairing of the targeting and effector elements. The adoption of Fc-fusion configuration in the molecular constructs is a preferred embodiment. It is conceivable for those skilled in the arts to link the pairs of targeting and effector elements of this invention employing other molecular platforms, such as peptides, proteins (e.g., albumin), polysaccharides, polyethylene glycol, and other types of polymers, which serve as a structural base for attaching multiple molecular elements.

The present disclosure also pertains to method for preventing and/or treating diseases/conditions associated with transplantation rejection in a subject (recipient) receiving a donor transplant (e.g., an organ, a tissue, or cells). Generally, the method comprises the step of administering to a subject in need of such treatment an effective amount of the Fc-based molecular construct according to embodiments of the present disclosure.

EXPERIMENTAL EXAMPLES

Example 1: Synthesis of Peptide 1 (SEQ ID NO: 18), Peptide 2 (SEQ ID NO: 26), and Peptide 3 (SEQ ID NO: 19) as Peptide Cores, and Conjugation of SH Group of Cysteine Residue with Maleimide-PEG$_3$-Transcyclooctene (TCO) as a Coupling Arm Each of peptides 1 to 3 (Chinapeptide Inc., Shanghai, China) was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of cysteine residue with maleimide-PEG$_3$-TCO (Conju-probe Inc.) to create a functional linking group TCO, the peptide and maleimide-PEG$_3$-TCO were mixed at a 1/5 ratio and incubated at pH 7.0 and 4° C. for 18 hours. TCO-conjugated peptides were purified by reverse phase HPLC on a Supelco C18 column (250 mm×10 mm; 5 μm), using a mobile phase of acetonitrile and 0.1% trifluoroacetic acid, a linear gradient of 0% to 100% acetonitrile over 30 minutes, at a flow rate of 1.0 mL/min and a column temperature of 25° C.

The present TCO-peptide 1, as illustrated below, had a molecular weight of 2,078.9 Daltons.

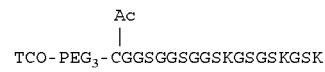

The present TCO-peptide 2, as illustrated below, had a molecular weight of 2,020.09 Daltons.

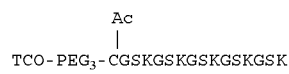

The present TCO-peptide 3, as illustrated below, had a molecular weight of 3,381.85 Daltons.

Example 2: Synthesis of Linker Unit by Conjugating NHS-PEG$_{12}$-Mal to NH$_2$ Groups of TCO-Peptides 1

Three linking arms of PEG$_{12}$-maleimide were attached to the peptide core TCO-peptide 1. The crosslinker, NHS-PEG$_{12}$-maleimide (succinimidyl-[(N-maleimido-propionamido)-dodecaethyleneglycol] ester, was purchased from Conju-probe Inc. The conjugation procedure was performed per the manufacturer's instruction; the peptide with lysine residues was dissolved in the conjugation buffer, phosphate buffered saline (PBS, pH 7.5) at 100 mM. NHS-PEG$_{12}$-maleimide crosslinker was added to the dissolved peptide at a final concentration of 1 mM (10-fold molar excess over 0.1 mM peptide solution). The reaction mixtures were incubated for 18 hours at room temperature. The maleimide-PEG$_{12}$-conjugated TCO-peptide 1 was purified by reverse phase HPLC on a Supelco C18 column (250 mm×4.6 mm; 5 μm), using a mobile phase of acetonitrile and 0.1% trifluoroacetic acid, a linear gradient of 0% to 100% acetonitrile over 30 minutes, at a flow rate of 1.0 ml/min and a column temperature of 25° C.

As illustrated below, the thus-synthesized maleimide-PEG$_{12}$-conjugated TCO-peptide 1 carried one coupling arm with a TCO group and three PEG linking arms with maleimide groups; it had a molecular weight of 4,332 Daltons.

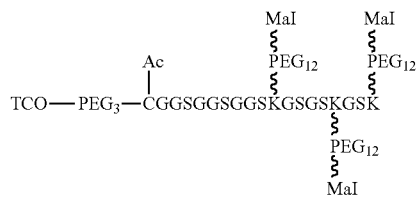

Example 3: Synthesis of Sirolimus-Gly and Sirolimus-diGly Molecule

Sirolimus monoglycine (sirolimus-Gly) and sirolimus diglycine (sirolimus-diGly) were designed and prepared under a contractual arrangement with Dr. Jiann-Jyh Huang's laboratory at the Department of Applied Chemistry, National Chiayi University, Chiayi, Taiwan.

For the synthesis of sirolimus-Gly (7a) and sirolimus-diGly (7b), sirolimus (1) served as the starting material and was reacted with trimethylsilyl chloride (TMSCl) using imidazole as the base to give 28,40-bis-O-TMS sirolimus (see the following Scheme 6). The trimethylsilyl group at the 40-O position of 28,40-bis-O-TMS sirolimus was selectively removed by imidazole and imidazole hydrochloride to give 28-O-TMS sirolimus (2) in 82% total yield. Esterification of the 40-OH by tritylglycine (3) and tritylglycylglycine (4) using DCC as the coupling agent and DMAP as the catalyst in CH$_2$Cl$_2$ gave 28-O-TMS sirolimus-GlyTrt (5a) and 28-O-TMS sirolimus-diGlyTrt (5b) in 75% and >99% yields, respectively. The trimethylsilyl group in 5a and 5b was removed under acidic conditions to afford sirolimus-GlyTrt (6a) in 99% yield and sirolimus-diGlyTrt (6b) in 85% yield. Deprotection of the trityl group in 6a and 6b by HOBt in trifluoroethanol gave the desired sirolimus-Gly (7a) and sirolimus-diGly (7b) in 61% and 27% yields, respectively.

Reagents and starting materials were used as purchased without further purification. Analytical thin-layer chromatography (TLC) was performed on precoated plates (silica gel 60 F-254), purchased from Merck Inc. Purification by column chromatography was conducted using Merck Reagents Silica Gel 60 (particle size of 0.063-0.200 mm, 70-230 mesh ASTM). Proton NMR spectra were recorded on an Agilent <<Scheme 6 Synthesis of sirolimus-Gly (7a) and sirolimus-diGly (7b)>>

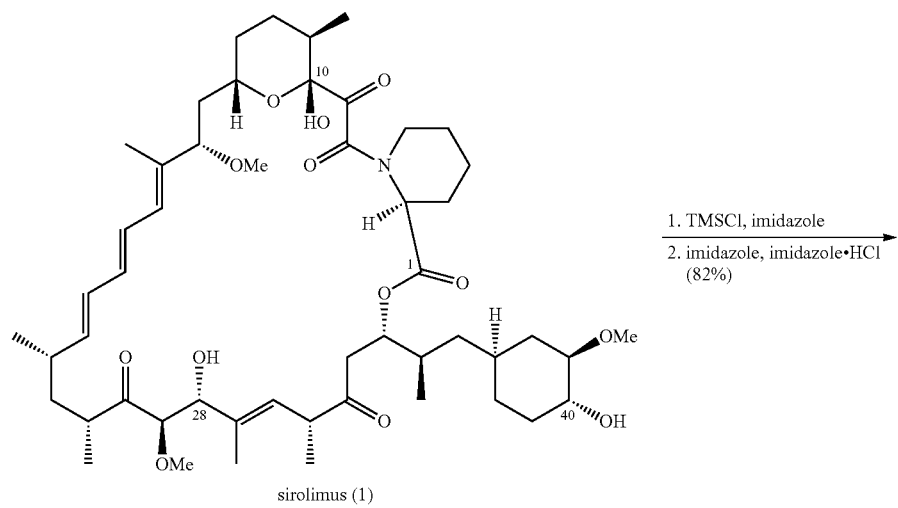

-continued
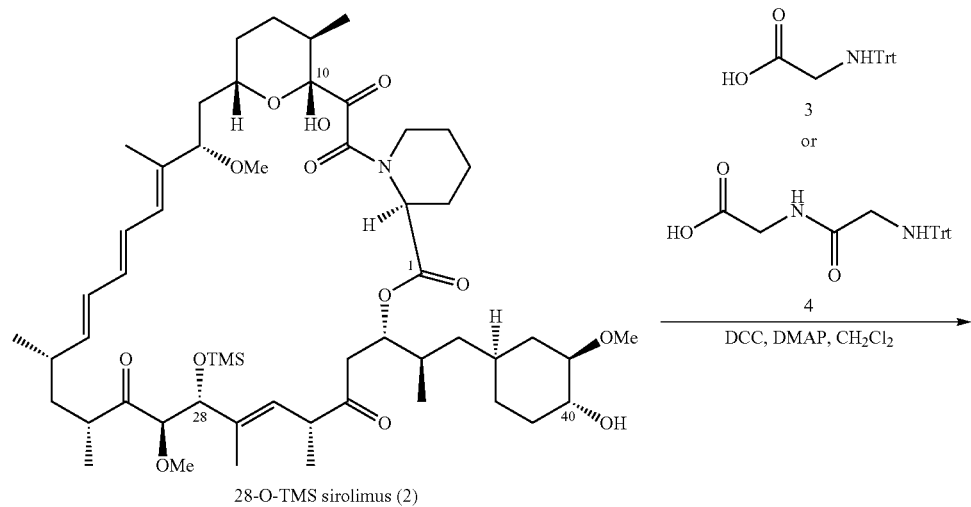
28-O-TMS sirolimus (2)
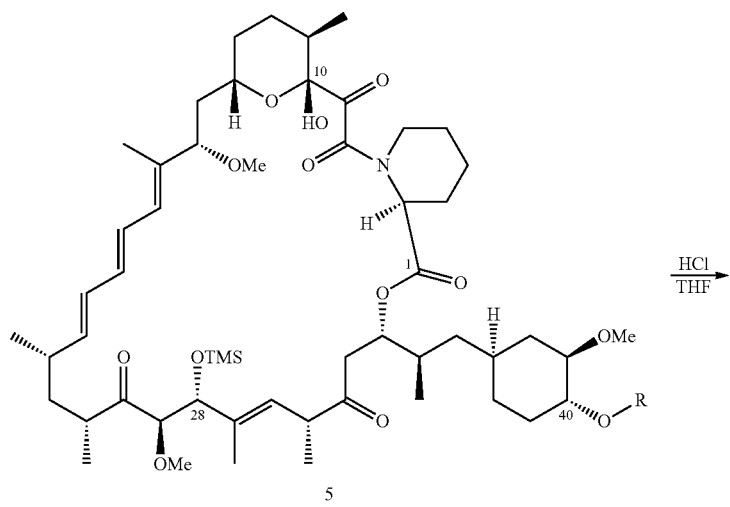
5
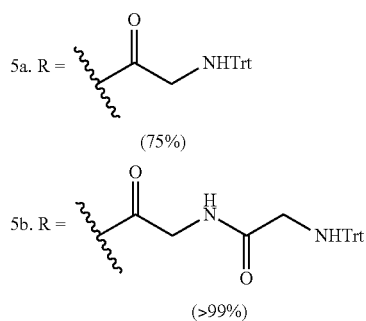
(75%)
(>99%)

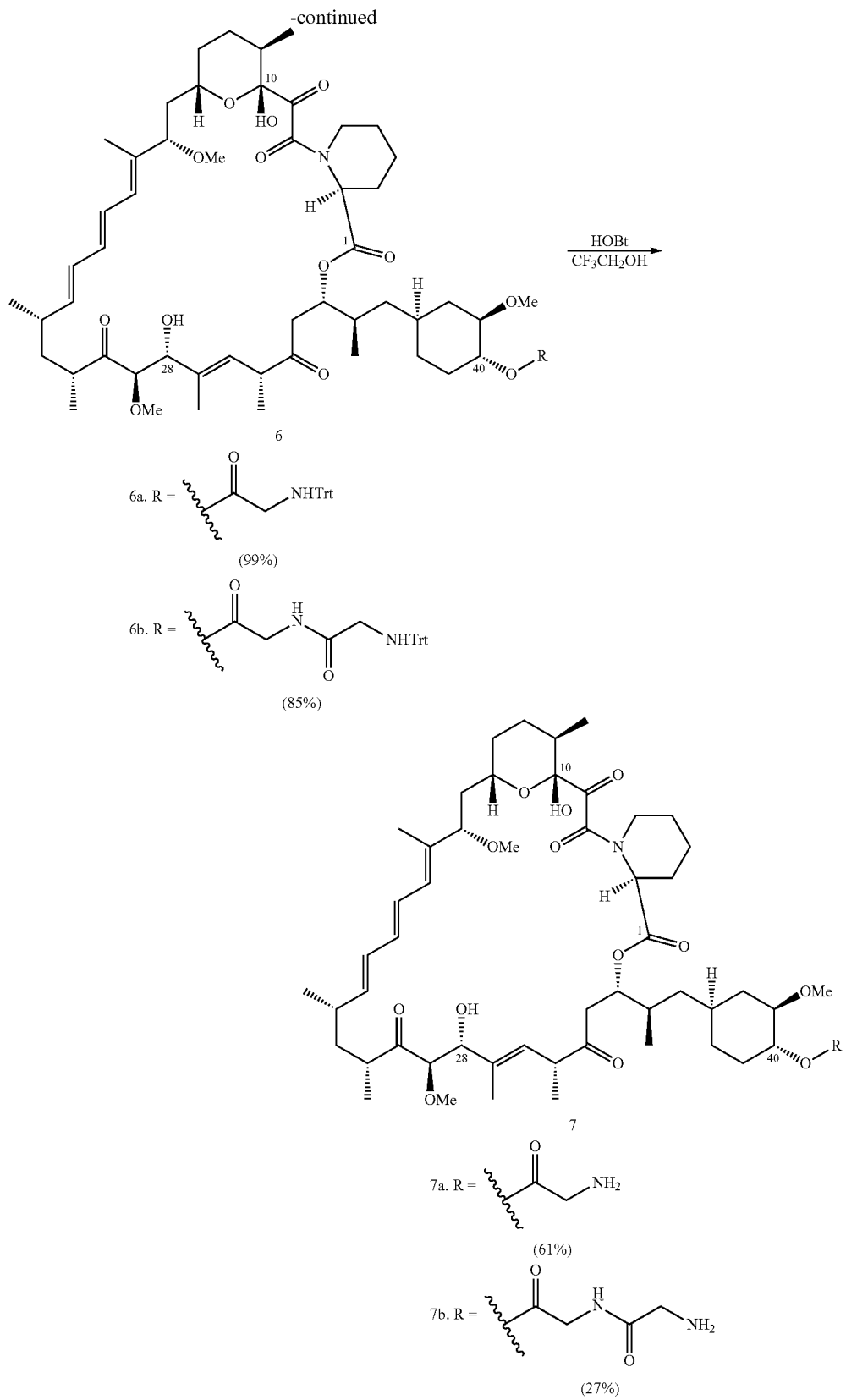
400-MR (400 MHz) spectrometer with CD$_3$OD or DMSO-d$_6$ as solvent. Multiplicities are abbreviated as follows: s, singlet; d, doublet; t, triplet; q, quartet; m, multiplet. ESI-MS mass spectra were obtained on a Finnigan LCQ mass spectrometer. High-resolution mass spectra were obtained by means of an LTQ Orbitrap XL mass spectrometer (Thermo Fisher Scientific). Tritylglycine (3) and tritylglycylglycine (4) were prepared according to reported procedures (Nogusa et al., 1995).

28-O-TMS Sirolimus (2).

Sirolimus (1, 1.992 g, 2.179 mmol, 1.0 equiv) and imidazole (0.1494 g, 2.194 mmol. 1.0 equiv) in $CH_2Cl_2$ (109 mL) were slowly added with trimethylsilyl chloride (TM-SCl, 1.0 M in $CH_2Cl_2$, 13.0 mL, 13.0 mmol, 6.0 equiv) in an ice bath. The reaction mixture was stirred at 0° C. and the reaction was monitored by TLC. After the reaction was complete (about 10 minutes), the solution was concentrated under reduced pressure. The residue was purified by flash column chromatography using 50% EtOAc in hexanes as the eluent to give 28,40-bis-O-TMS sirolimus (2.261 g, 2.136 mmol): ESI-MS: 1080.62 $(M+Na)^+$. The obtained 28,40-Bis-O-TMS sirolimus was mixed with imidazole (2.250 g, 33.05 mmol, 15 equiv) and imidazole hydrochloride (3.463 g, 33.13 mmol, 16 equiv) in $CH_2Cl_2$ (218 mL). The reaction mixture was stirred at room temperature and the reaction was monitored by TLC. After the reaction was complete (about 3 hours), the solution was concentrated under reduced and the residue was purified by flash column chromatography using 50% EtOAc in hexanes as the eluent to give 28-O-TMS sirolimus (2, 1.772 g, 1.796 mmol) in 82% total yield: ESI-MS: 1008.58 $(M+Na)^+$.

28-O-TMS Sirolimus-GlyTrt (5a).

A solution of 2 (0.305 g, 0.309 mmole, 1.0 equiv), tritylglycine (3, 0.592 g, 1.87 mmol, 6.1 equiv), and DMAP (0.065 g, 0.532 mmol, 1.7 equiv) in anhydrous $CH_2Cl_2$ (10 mL) was slowly added with DCC (0.386 g, 1.87 mmol, 6.1 equiv) in anhydrous $CH_2Cl_2$ (5.0 mL). The reaction mixture was stirred at room temperature and the reaction was monitored by TLC. After the reaction was complete (about 3 hours), the solution was added with $H_2O$ (1.0 mL) and the white DBU precipitate was filtered. The filtrate was diluted with EtOAc and washed with saturated $NaHCO_3$. The organic layer was dried over $MgSO_4$, filtered, and concentrated under reduced pressure. The residue was purified by column chromatography using 25% EtOAc in hexanes as the eluent to give 5a (300 mg, 0.233 mmol) in 75% yield.

28-O-TMS Sirolimus-diGlyTrt (5b).

Compound 5b was prepared as the same procedure to 5a using 2 (0.305 g, 0.309 mmol, 1.0 equiv), tritylglycylglycine (4, 0.347 g, 0.927 mmol, 3.0 equiv), DMAP (11 mg, 0.090 mmol, 0.30 equiv), and DCC (0.240 g, 1.16 mmol, 3.8 equiv). The reaction gave 5b (0.535 g, 0.398 mmol) in >99% yield: HRMS calcd for $C_{77}H_{107}N_3NaO_{15}Si$ $(M+H)^+$ 1364.7364, found 1364.7275.

Sirolimus-GlyTrt (6a).

Compound 5a (0.193 g, 0.150 mmol, 1.0 equiv) in THF (10 mL) was added with $H_2O$ (2.0 mL) and 0.10 N HCl (0.50 mL) in an ice bath. The reaction mixture was stirred at room temperature for 12 hours. The solution was added with $NaHCO_3$ (0.10 M, 1.0 mL) and diluted with EtOAc. The solution was washed with water, dried over $MgSO_4$, and concentrated under reduced pressure. The residue was purified by column chromatography using 50% EtOAc in hexanes as the eluent to give 6a (180 mg, 0.148 mmol) in 99% yield. HRMS calcd for $C_{72}H_{97}N_2O_{14}$ $(M+H)^+$ 1213.6934, found 1213.6887.

Sirolimus-diGlyTrt (6b).

Compound 6b was prepared as the same procedure to 6a using 5b (0.535 g, 0.398 mmol, 1.0 equiv). The reaction gave 6b (0.431 g, 0.339 mmol) in 85% yield: HRMS calcd for $C_{74}H_{100}N_3O_{15}$ $(M+H)^+$ 1270.7149, found 1270.7054.

Sirolimus-Gly (7a).

Compound 6a (0.168 g, 0.138 mmol, 1.0 equiv) was dissolved in 0.10 M HOBt solution in trifluorothanol (1.0 mL) and the reaction was monitored by TLC. After the reaction was complete (~12 h), the solution was added with $H_2O$ (0.10 mL) and diluted with EtOAc. The solution was washed with saturated $Na_2CO_3$, dried over $MgSO_4$, filtered, and concentrated under reduced pressure. The residue was purified by column chromatography to give 7a (82 mg, 0.084 mmol) in 61% yield: HRMS calcd for $C_{53}H_{83}N_2O_{14}$ $(M+H)^+$ 971.5839, found 971.5806; $^1H$ NMR $(CD_3OD)$ δ 6.48-6.36 (m, 2H), 6.30-6.03 (m, 3H), 5.47 (s, 1H), 5.42 (d, 1H), 5.21 (d, 1H), 5.06 (d, 1H), 4.68 (s, 1H), 4.15 (d, 1H), 4.08 (d, 1H), 3.98 (d, 1H), 3.66 (d, 1H), 3.56-3.50 (m, 1H), 3.41 (s, 2H), 3.36 (s, 3H), 3.26 (s, 3H), 3.12 (s, 3H), 2.84-2.80 (m, 1H), 2.79-2.76 (m, 1H), 2.48-2.40 (m, 2H), 2.35-0.90 (m, 52H).

Sirolimus-diGly (7b).

Compound 7b was prepared as the same procedure to 7a using 6b (0.431 g, 0.339 mmol, 1.0 equiv). The reaction gave 7b (96 mg, 0.093 mmol) in 27% yield: $^1H$ NMR $(DMSO-d_6)$ δ 6.70-6.53 (m, 1H), 6.48-6.22 (m, 2H), 6.23-6.00 (m, 3 H), 5.58-5.33 (m, 1H), 5.29-5.10 (m, 2H), 4.98-4.84 (m, 2H), 4.60-4.41 (m, 2H), 4.14-4.01 (m, 5H), 3.99-3.46 (m, 2H), 3.76-3.46 (m, 3H), 3.21 (s, 3H), 3.12 (s, 3H), 3.00 (s, 1H), 2.94 (s, 3H), 2.75-2.60 (m, 2H), 2.39-2.28 (m, 1H), 2.26-2.16 (m, 1H), 2.15-1.75 (m, 3H), 1.68-0.53 (m, 45H).

Figure 6A:
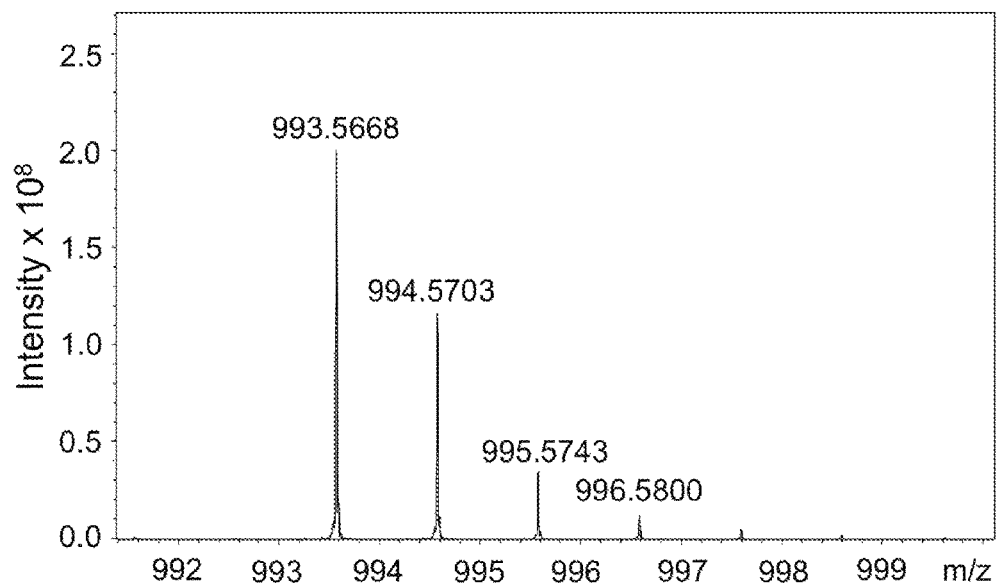
FIG. 6A and FIG. 6B respectively show the mass spectrometric analysis of the sirolimus-Gly and sirolimus-diGly, according to one working example of the present disclosure.

FIG. 6A shows mass spectrometric analysis of the thus-synthesized sirolimus-Gly (compound 7a of scheme 6); MS (ESI) calculated for $C_{53}H_{82}N_2O_{14}$ 971.22; found 993.5668, corresponding to [M+Na]+. The three isotopic peaks were also visible in the MS spectrum at 994.57, 995.574, and 996.58, corresponding to $[M+Na+1]^+$, $[M+Na+2]^+$, and $[M+Na+3]^+$.

Figure 6B:
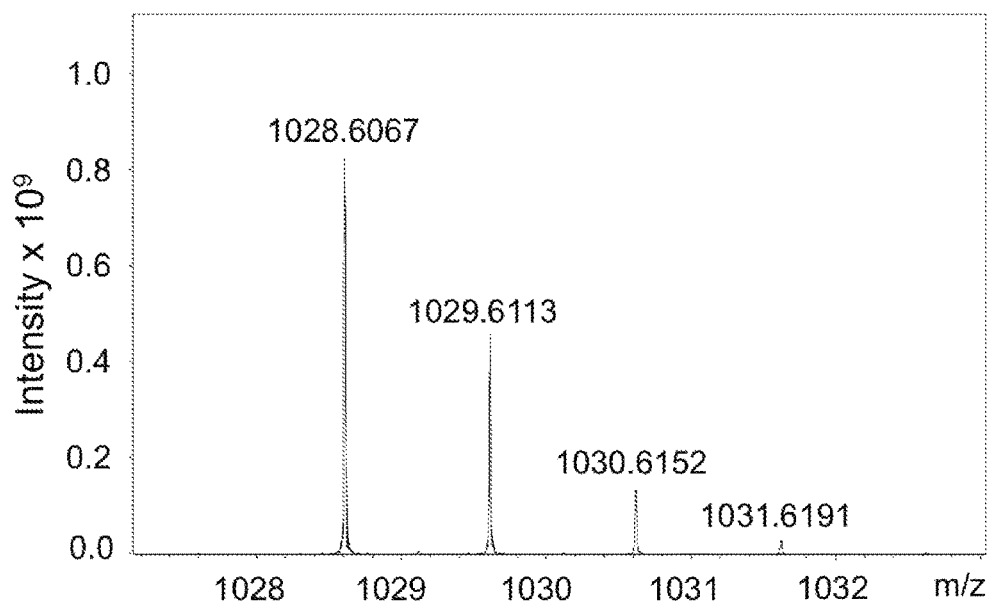

FIG. 6B shows mass spectrometric analysis of the thus-synthesized sirolimus-diGly (compound 7b of scheme 6); MS (ESI) calculated for $C_{55}H_{85}N_3O_{15}$ 1028.27; found 1028.6067, corresponding to $[M+H]^+$. The three isotopic peaks were also visible in the MS spectrum at 1029.6113, 1030.6152, and 1031.6191, corresponding to $[M+H+1]^+$, $[M+H+2]^+$, and $[M+H+3]^+$.

Example 4: Conjugation of Sirolimus-Gly and Sirolimus-diGly Molecules with NHS—S—S-PEG₃-Azido Linking Arm In this example, the $NH_2$ group of the sirolimus-Gly and sirolimus-diGly molecule was reacted with a hetero-bifunctional cleavable linker, NHS—S—S—PEG₃-azido (Conjuprobe Inc.).

Briefly, sirolimus-Gly was dissolved in 100% DMSO at a final concentration of 50 mM, while NHS—S—S-PEG$_3$-azido was dissolved in 100% DMSO at a final concentration of 250 mM. 59.76 µl of the NHS—S—S-PEG$_3$-azido linker solution was added to 149.4 µl of the dissolved sirolimus-Gly solution at a final concentration of 5 mM (2-fold molar excess over 2.5 mM sirolimus-Gly solution). Then, 298.8 µl of a buffer solution containing 100 mM sodium phosphate buffer at pH 7.5 and 2,480 µl of 100% DMSO were added to the reaction mixture to reach a total volume of 2,988 µl. The reaction mixture was incubated for 3 hours at room temperature, and then the solvent was evaporated under vacuum.

The product, Azido-PEG$_3$-S—S-conjugated sirolimus-Gly, was dissolved in 65% acetonitrile; then purified by reverse phase HPLC on a Supelco C18 column (250 mm×10.0 mm; 5 µm), using a mobile phase of acetonitrile and 0.1% trifluoroacetic acid, a linear gradient of 50% to 100% acetonitrile over 20 minutes, at a flow rate of 3.0 mL/min and a column temperature of 45° C.

Figure 7A:
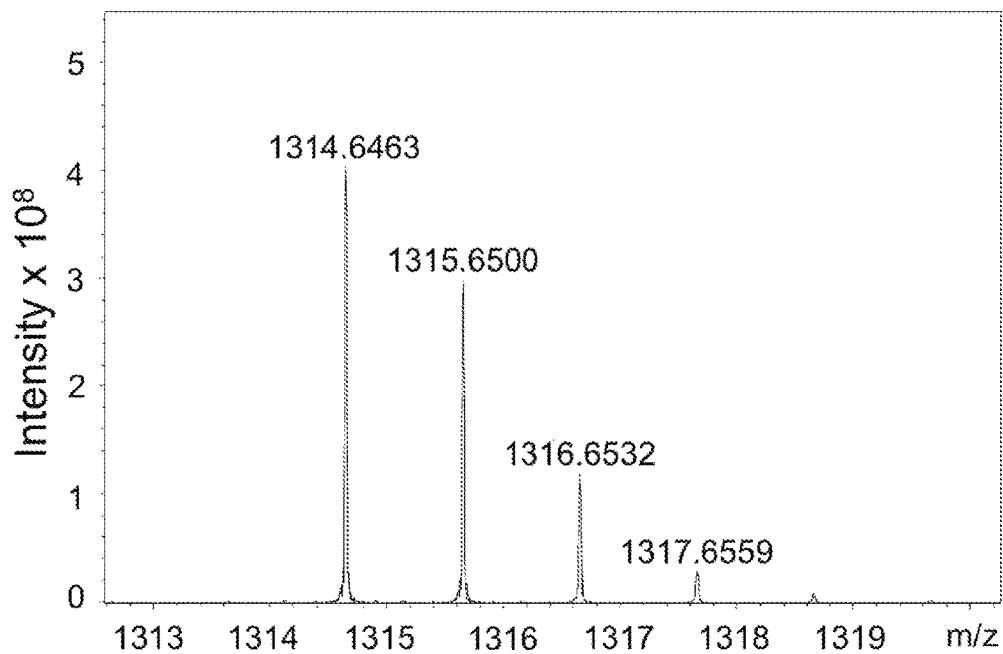
FIG. 7A and FIG. 7B respectively show the MALDI-TOF analysis of the azido-PEG3-S—S-conjugated sirolimus-Gly and sirolimus-diGly, according to one working example of the present disclosure.

FIG. 7A shows the mass spectrometric analysis of the thus-synthesized azido-PEG$_3$-S—S-conjugated sirolimus-Gly, as illustrated below. MS (ESI) calculated for $C_{64}H_{101}N_5O_{18}S_2$ 1292.64; found 1314.6463, corresponding to [M+Na]$^+$. The three isotopic peaks were also visible in the MS spectrum at 1315.65, 1316.6532, and 1317.6559, corresponding to [M+Na+1]$^+$, [M+Na+2]$^+$, and [M+Na+3]$^+$.

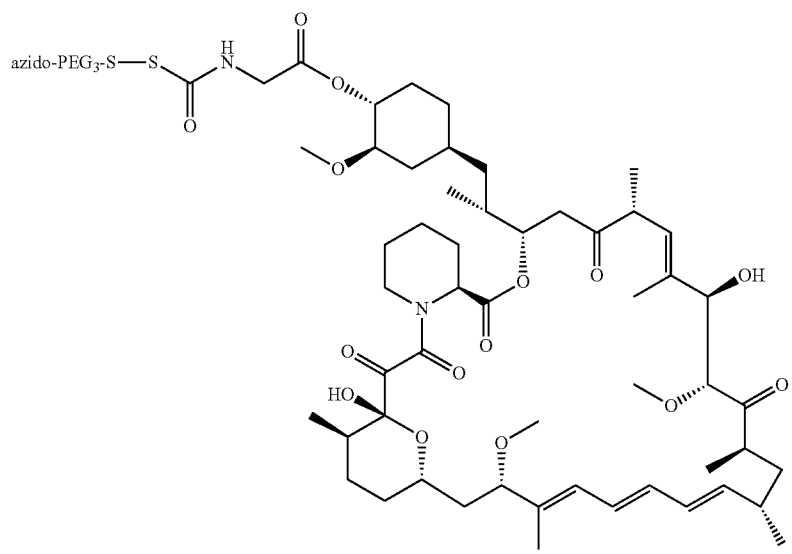

Similarly, sirolimus-diGly was dissolved in 100% DMSO at a final concentration of 50 mM, and NHS—S—S-PEG$_3$-azido linker was dissolved in 100% DMSO at a final concentration of 250 mM. 46.68 µl of the NHS—S—S-PEG$_3$-azido linker solution was then added to 116.7 µl of the dissolved sirolimus-diGly solution at a final concentration of 5 mM (2-fold molar excess over 2.5 mM sirolimus-diGly solution). Then, 233.4 µl of a buffer solution containing 100 mM sodium phosphate buffer at pH 7.5 and 1,937.22 µl of 100% DMSO were added to the reaction mixture to reach a total volume of 2,334 µl. The reaction mixture was incubated for 3 hours at room temperature, and then the solvent was evaporated under vacuum. The product was purified using reverse phase HPLC following the protocol described above.

Figure 7B:
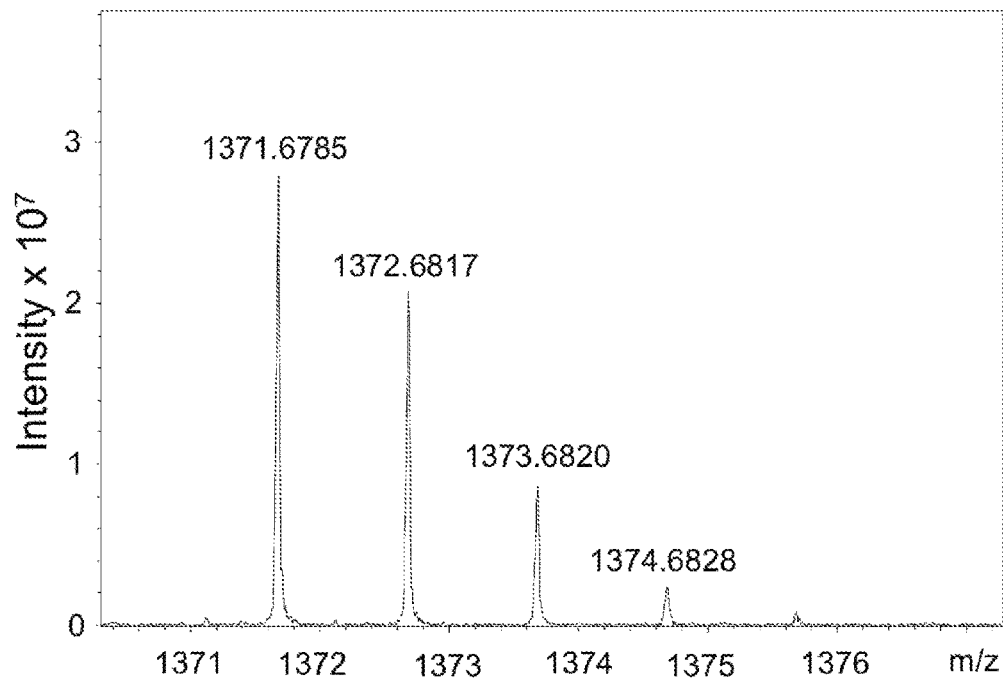

FIG. 7B shows the mass spectrometric analysis of the thus-synthesized azido-PEG$_3$-S—S-conjugated sirolimus-diGly, as illustrated below. MS (ESI) calculated for $C_{66}H_{104}N_5O_{19}S_2$ 1349.69; found 1371.6785, corresponding to [M+Na]$^+$. The three isotopic peaks were also visible in the MS spectrum at 1372.6817, 1373.682, and 1374.6828, corresponding to [M+Na+1]$^+$, [M+Na+2]$^+$, and [M+Na+3]$^+$.

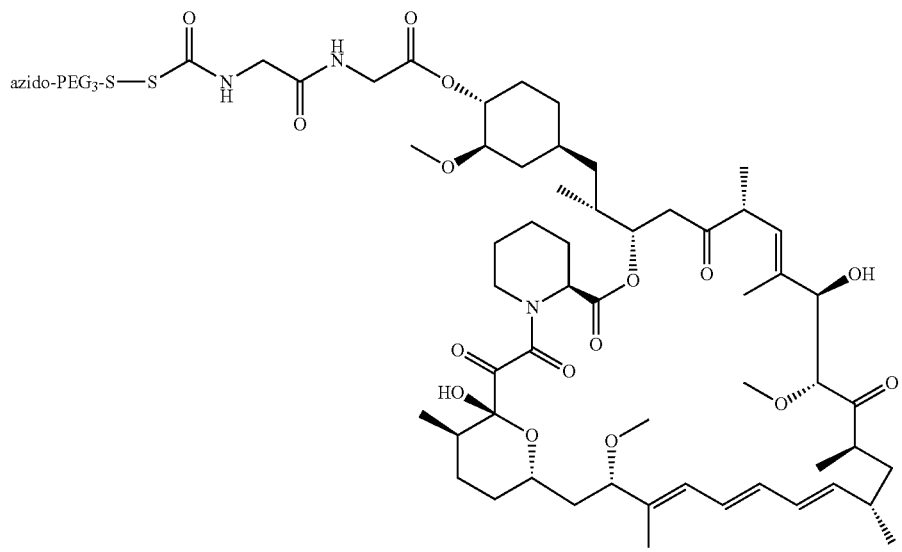

Example 5: Conjugation of Fingolimod and Fingolimod Phosphate Molecule with NHS-PEG$_5$-NHS Cross-Linker Fingolimod was purchased from Biotang Inc. (Lexington, USA) and fingolimod phosphate from KM3 Scientific Corporation (New Taipei City, Taiwan). The $NH_2$ group of fingolimod molecule was reacted with a homo-bifunctional crosslinker, NHS-PEG$_5$-NHS as shown in scheme 7.

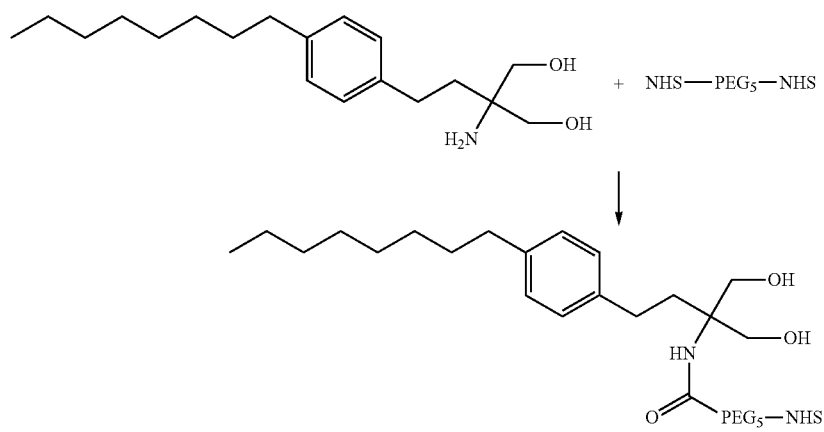

Briefly, fingolimod was dissolved in 100% DMSO at a final concentration of 10 mM, while NHS-PEG$_5$-NHS, a homo-bifunctional crosslinker, was dissolved in 100% DMSO at a final concentration of 250 mM. To activate the $NH_2$ group of fingolimod, 6% (v/v) of basic sodium phosphate buffer (pH12.7) was added to the fingolimod solution and then incubated for 10 minutes. NHS-PEG$_5$-NHS crosslinker was added to the dissolved fingolimod solution at a final concentration of 30 mM (3-fold molar excess over 10 mM fingolimod solution). The reaction mixture was incubated for 3 hours at room temperature.

Fingolimod phosphate was dissolved in 100% DMSO at a final concentration of 5 mM, and NHS-PEG$_5$-NHS crosslinker was dissolved in 100% DMSO at a final concentration of 250 mM. NHS-PEG$_5$-NHS crosslinker was added to the dissolved fingolimod phosphate solution at a final concentration of 15 mM (3-fold molar excess over 5 mM fingolimod phosphate solution). The reaction mixture was incubated for 3 hours at room temperature, then added 18% (v/v) acid sodium phosphate buffer (decreasing pH value of the buffer solution) to quench the reaction. The solvent was evaporated under vacuum.

The NHS-PEG$_5$-conjugated fingolimod and NHS-PEG$_5$-conjugated fingolimod phosphate were respectively dissolved in 30% acetonitrile, then purified by reverse phase HPLC on a Supelco C18 column (250 mm×4.6 mm; 5 μm), using a mobile phase of acetonitrile and 0.1% trifluoroacetic acid, a linear gradient of 30% to 100% acetonitrile over 30 minutes, at a flow rate of 1.0 mL/min and a column temperature of 25° C.

Figure 8:
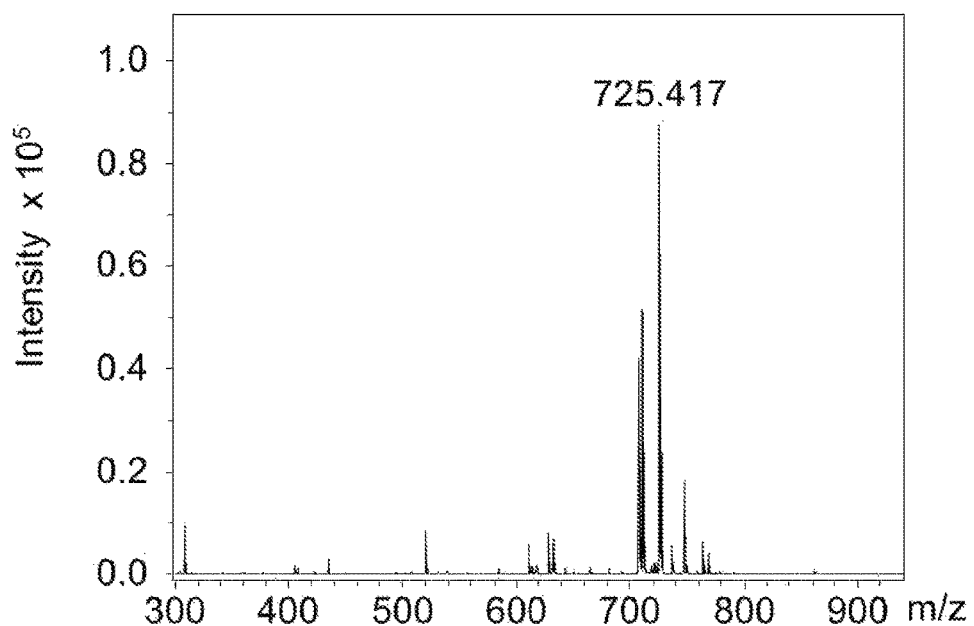
FIG. 8 shows the MALDI-TOF analysis of the NHS-PEG5-conjugated fingolimod.

FIG. 8 shows that the thus-synthesized NHS-PEG$_5$-conjugated fingolimod, as illustrated above in scheme 7, had a molecular weight of 725.41 Daltons.

The present NHS-PEG$_5$-conjugated fingolimod phosphate, as illustrated below, had a molecular weight of 803.3 Daltons.

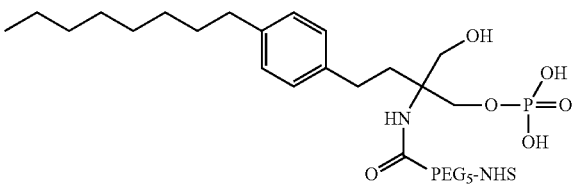

Example 6: Conjugation of Fingolimod Molecule with NHS—S—S-PEG$_3$-Azido Linking Arm The NH$_2$ group of fingolimod molecule was reacted with a hetero-bifunctional cleavable linker, NHS—S—S—PEG$_3$-azido (Conju-probe Inc.), at a 1:3 molar ratio. The product, azido-PEG$_3$-S—S-fingolimod was purified by HPLC to remove the excess, unreacted fingolimod molecules. The procedures for conjugation and purification were similar to those described in the preceding example.

Figure 9:
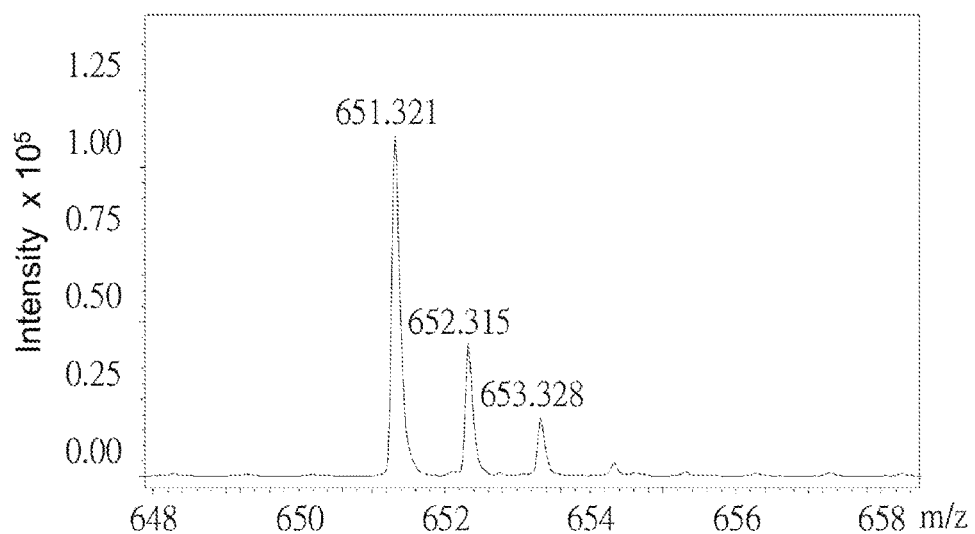
FIG. 9 shows the mass spectrometric analysis of the azido-PEG3-S—S-conjugated fingolimod according to one working example of the present disclosure.

FIG. 9 shows the mass spectrometric analysis of the thus-synthesized azido-PEG$_3$-S—S-conjugated fingolimod, as illustrated below. MS (ESI) calculated for $C_{30}H_{53}N_4O_6S_2$ 629.9007; found 651.321, corresponding to [M+Na]$^+$. The three isotopic peaks were also visible in the MS spectrum at 652.315 and 653.328, corresponding to [M+Na+1]$^+$ and [M+Na+2]$^+$.

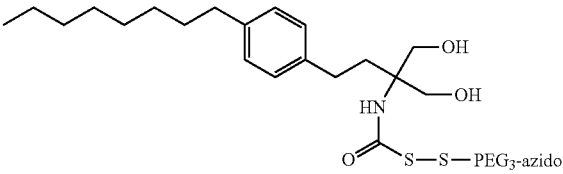

Example 7: Conjugation of Azido-PEG$_3$-S—S-Conjugated Sirolimus-Gly Molecule with DBCO-PEG$_4$-NHS Crosslinker Azido-PEG$_3$-S—S-conjugated sirolimus-Gly molecule was dissolved in 100% DMSO at a final concentration of 10 mM, and DBCO-PEG$_4$-NHS crosslinker was dissolved in 100% DMSO at a final concentration of 250 mM. 4 μl of the DBCO-PEG$_4$-NHS crosslinker solution was added to 50 μl of the azido-PEG$_3$-S—S-conjugated sirolimus-Gly solution at a final concentration of 4 mM, so that the final molar ratio of DBCO-PEG$_4$-NHS to azido-PEG$_3$-S—S-conjugated sirolimus-Gly is 2:1. The reaction mixture was incubated for 3 hours at room temperature for the SPAAC reaction.

Figure 10A:
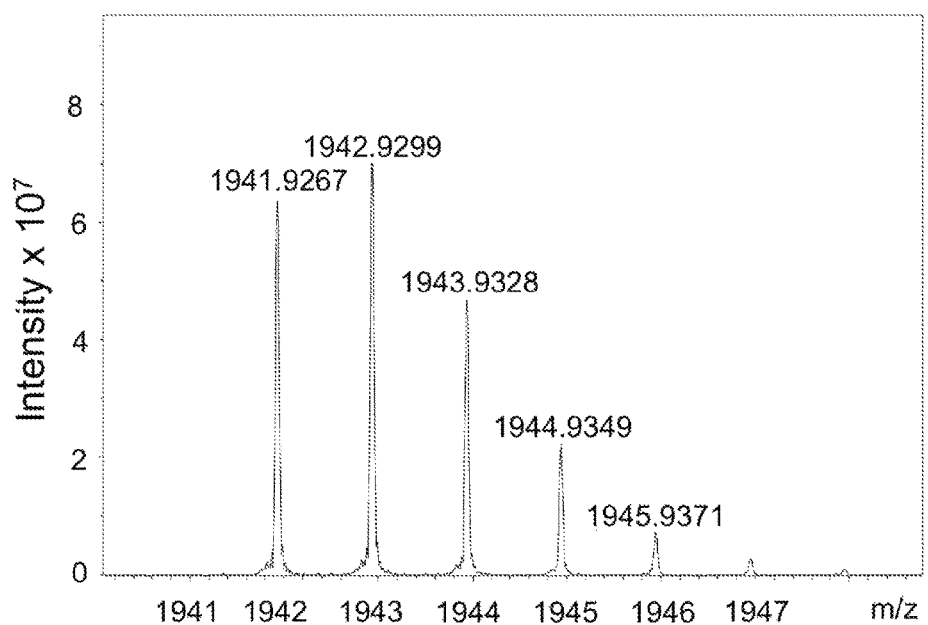
FIG. 10A and FIG. 10B respectively show the mass spectrometric analysis of the NHS-PEG4-PEG3-S—S-conjugated sirolimus-Gly and sirolimus-diGly, according to one working example of the present disclosure.

FIG. 10A shows the mass spectrometric analysis of the thus-synthesized NHS-PEG$_4$-PEG$_3$-S—S-conjugated sirolimus-Gly, as illustrated below (the diamond symbol represents a condensation product of SPAAC). MS (ESI) calculated for $C_{98}H_{140}N_8O_{28}S_2$ 1942.33; found 1941.9267, corresponding to [M+H]$^+$. The four isotopic peaks were also visible in the MS spectrum at 1942.9299, 1943.9328, 1944.9349 and 1945.9371, corresponding to [M+H+1]$^+$, [M+H+2]$^+$, [M+H+3]$^+$, and [M+H+4]$^+$.

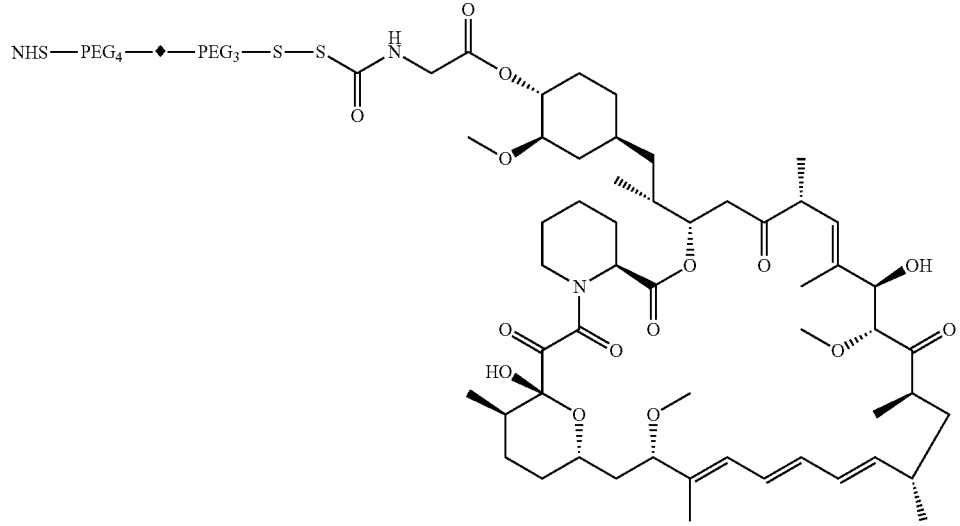

Figure 10B:
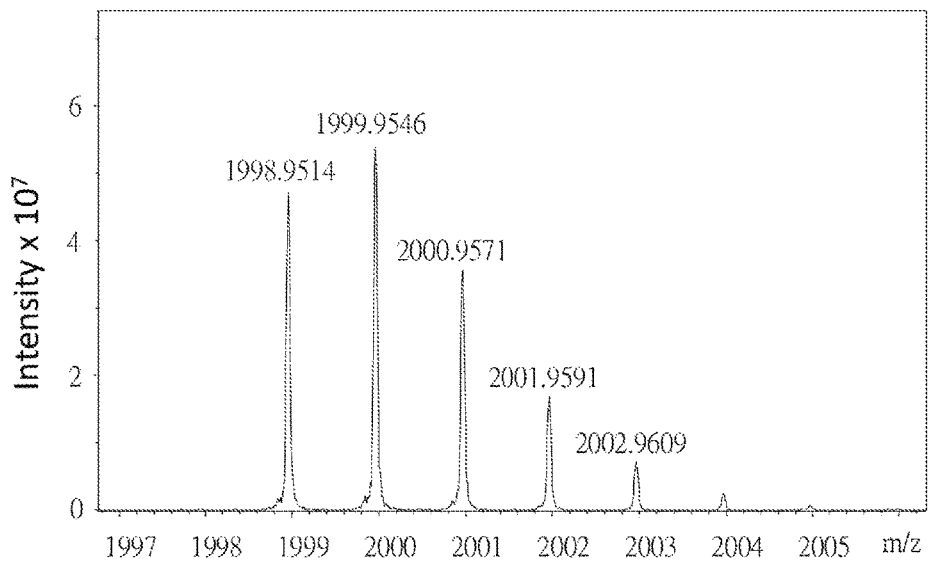

FIG. 10B shows the mass spectrometric analysis of the thus-synthesized NHS-PEG$_4$-PEG$_3$-S—S-conjugated sirolimus-diGly, as illustrated below (the diamond symbol represents a condensation product of SPAAC). MS (ESI) calculated for $C_{100}H_{143}N_9O_{29}S_2$ 1999.38; found 1998.9514, corresponding to [M+H]$^+$. The four isotopic peaks were also visible in the MS spectrum at 1999.9546, 2000.9571, 2001.9591 and 2002.9609, corresponding to [M+H+1]$^+$, [M+H+2]$^+$, [M+H+3]$^+$, and [M+H+4]$^+$.

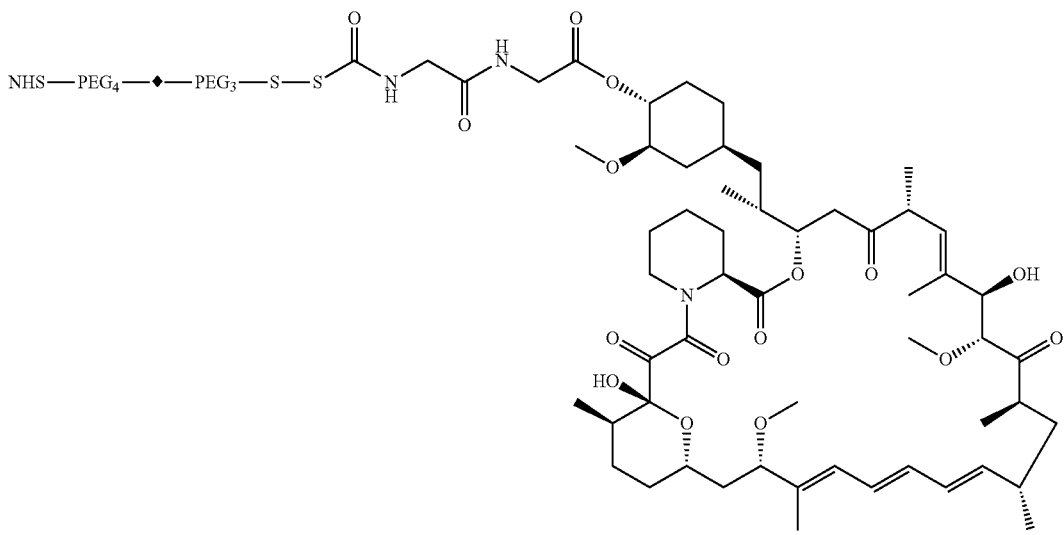

Example 8: Conjugation of Azido-PEG₃-S—S-Conjugated Fingolimod Molecule with NHS-PEG₄-DBCO Crosslinker Azido-PEG$_3$-S—S-conjugated fingolimod molecule was dissolved in 100% DMSO at a final concentration of 10 mM, and NHS-PEG$_4$-DBCO crosslinker was dissolved in 100% DMSO at a final concentration of 250 mM. 5 µl of the NHS-PEG$_4$-DBCO crosslinker solution was added to 400 µl of the azido-PEG$_3$-S—S-conjugated fingolimod solution to a final molar ratio of 1/3.2 (NHS-PEG$_4$-DBCO: azido-PEG$_3$-S—S-conjugated fingolimod) in 100 mM sodium phosphate buffer at pH 7.5 (final concentration: 10 mM). The reaction mixture was incubated for 3 hours at room temperature for SPAAC reaction.

Figure 11:
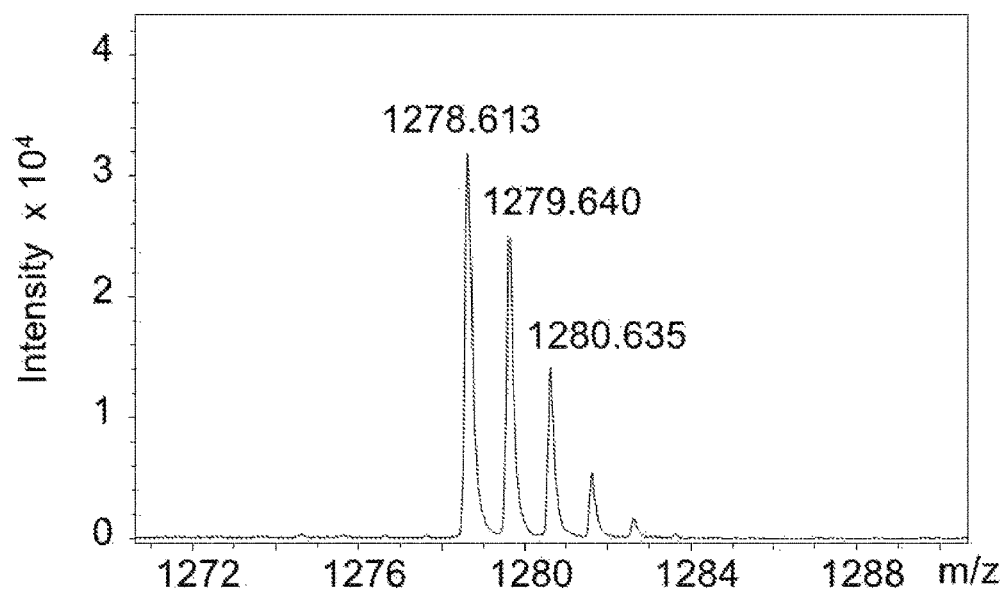
FIG. 11 shows the mass spectrometric analysis of the NHS-PEG4-PEG3-S—S-conjugated fingolimod, according to one working example of the present disclosure.

FIG. 11 shows mass spectrometric analysis of the thus-synthesized NHS-PEG$_4$-PEG$_3$-S—S-conjugated fingolimod, as illustrated below (the diamond symbol represents a condensation product of SPAAC). MS (ESI) calculated for $C_{64}H_{92}N_7O_{16}S_2$ 1278.5938; found 1278.613, corresponding to [M+H]⁺. The two isotopic peaks were also visible in the MS spectrum at 1279.640 and 1280.635, corresponding to [M+H+1]⁺ and [M+H+2]⁺.

Example 9: Conjugation of NHS-PEG₄-PEG₃-S—S-Conjugated Sirolimus-Gly to TCO-Peptide 2

TCO-peptide 2 was dissolved in 100 mM sodium phosphate buffer at pH 7.5 to a final concentration of 20 mM, and NHS-PEG$_4$-PEG$_3$-S—S-conjugated sirolimus-Gly was dissolved in 100% DMSO to a final concentration of 10 mM. 1.5 µl of TCO-peptide 2 and 60 µl of NHS-PEG$_4$-PEG$_3$-S—S-conjugated sirolimus-Gly were mixed at a molar ratio of 1:20 (TCO-peptide 2: NHS-PEG$_4$-PEG$_3$-S—S-conjugated sirolimus-Gly). Then, 3.5 µl of a buffer solution containing 100 mM sodium phosphate buffer at pH 10 and 35 µl of 100% DMSO were added to the reaction mixture to reach a total volume of 100 µl, and the reaction mixture was incubated for 3 hours at room temperature.

Figure 12A:
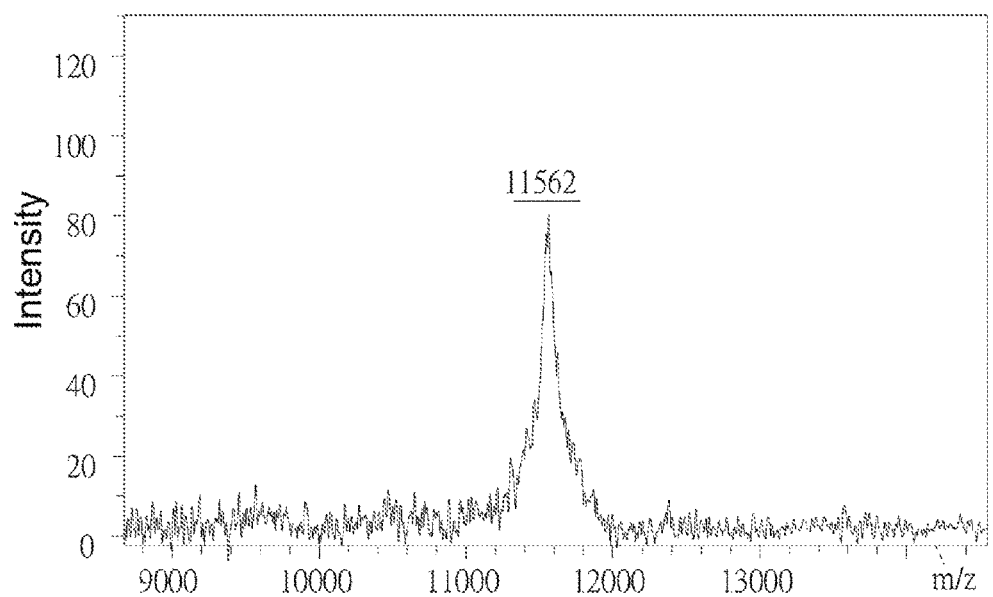
FIGS. 12A to 12D respectively show the MALDI-TOF analysis of a drug bundle composing of a linker unit with a free TCO functional group and a set of five sirolimus-Gly, five fingolimod, ten fingolimod and five fingolimod phosphate molecules, according to one working example of the present disclosure.

FIG. 12A shows that the thus-synthesized drug bundle, as illustrated below, had a molecular weight of 11,562 Daltons; it was composed of a linker unit with one free TCO functional group and a set of five sirolimus-Gly molecules.

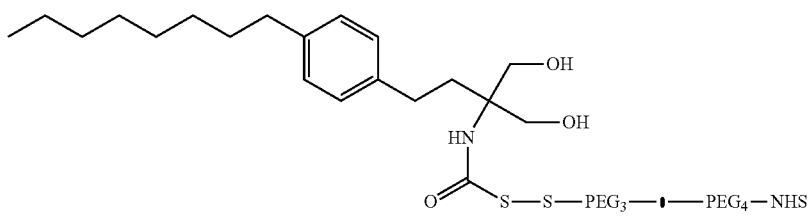

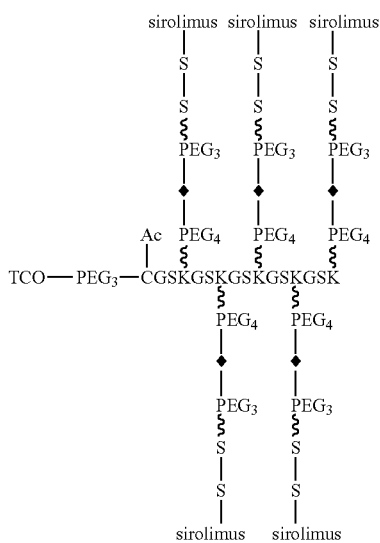

Example 10: Conjugation of NHS-PEG₅-Conjugated Fingolimod Molecules to TCO-Peptide 2 and 3

TCO-peptide 2 was dissolved in 100 mM sodium phosphate buffer at pH 7.5 to a concentration of 20 mM, and NHS-PEG$_5$-conjugated fingolimod was dissolved in 100% DMSO to a concentration of 50 mM. TCO-peptide 2 and NHS-PEG$_5$-conjugated fingolimod were mixed at a molar ratio of 1/42 and incubated for 3 hours at room temperature. Additional TCO-peptide 2 was subsequently added to the reaction solution to a final molar ratio of 1/13.5 (TCO-peptide 2: NHS PEG$_5$-conjugated fingolimod). The mixture was further incubated for 3 hours at room temperature.

Figure 12B:
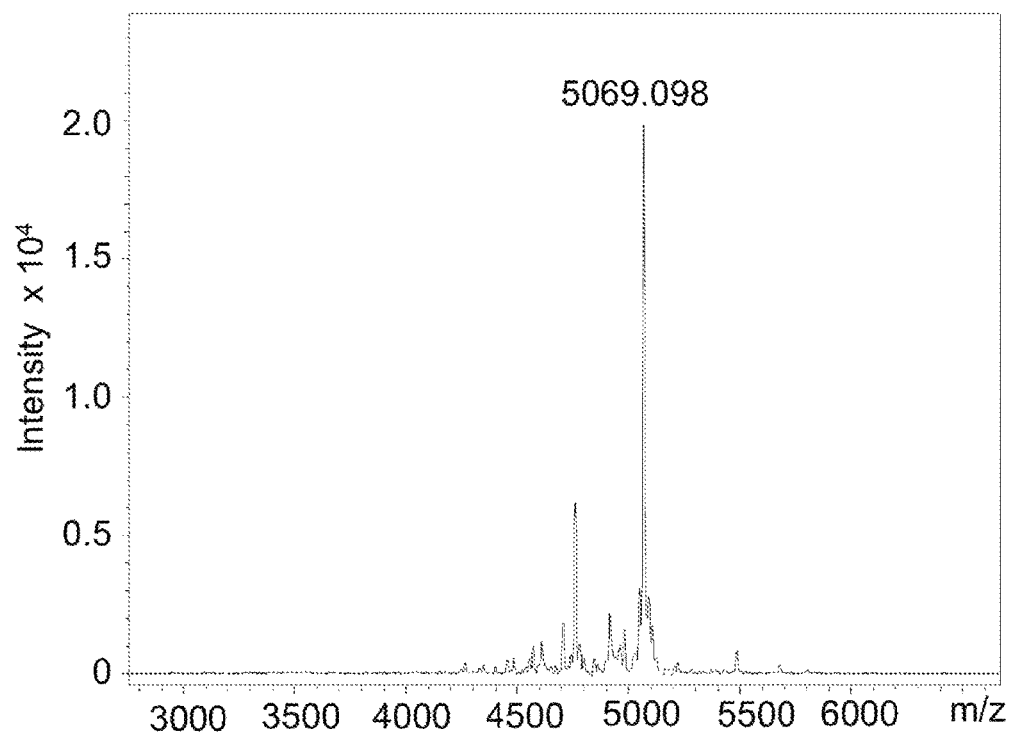

FIG. 12B shows that the drug bundle of TCO-peptide 2 with fingolimod had a molecular weight of 5,069 Daltons. The thus-synthesized drug bundle, as illustrated below, was composed of a linker unit with one free TCO functional group and a set of five fingolimod molecules.

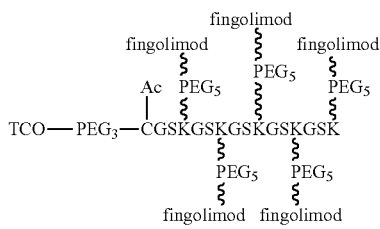

TCO-peptide 3 was dissolved in 100 mM sodium phosphate buffer at pH 7.5 to a concentration of 10 mM, and NHS-PEG$_5$-conjugated fingolimod was dissolved in 100% DMSO to a concentration of 50 mM. TCO-peptide 3 and PEG$_5$-NHS-conjugated fingolimod were mixed at a molar ratio of 1/42 at room temperature overnight.

Figure 12C:
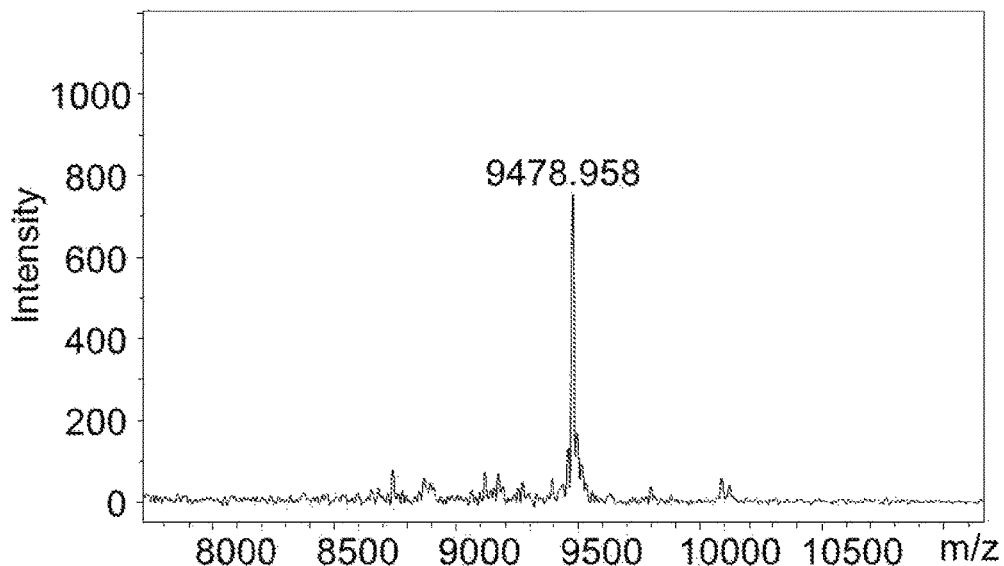

FIG. 12C shows that the drug bundle of TCO-peptide 3 with fingolimod had a molecular weight of 9,478.958 Daltons, indicating that 10 fingolimod molecules were conjugated to the TCO-peptide 3 linker unit. The present drug bundle, as illustrated below, was composed of a linker unit with one free TCO functional group and a set of ten fingolimod molecules.

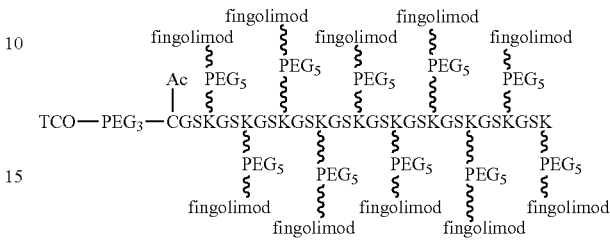

Example 11: Conjugation of NHS-PEG₅-Conjugated Fingolimod Phosphate Molecules to TCO-Peptide 2

TCO-peptide 2 and NHS-PEG$_5$-conjugated fingolimod phosphate were mixed at a molar ratio of 1/42 in 100 mM sodium phosphate buffer at pH 7.5 at room temperature for 3 hours.

Figure 12D:
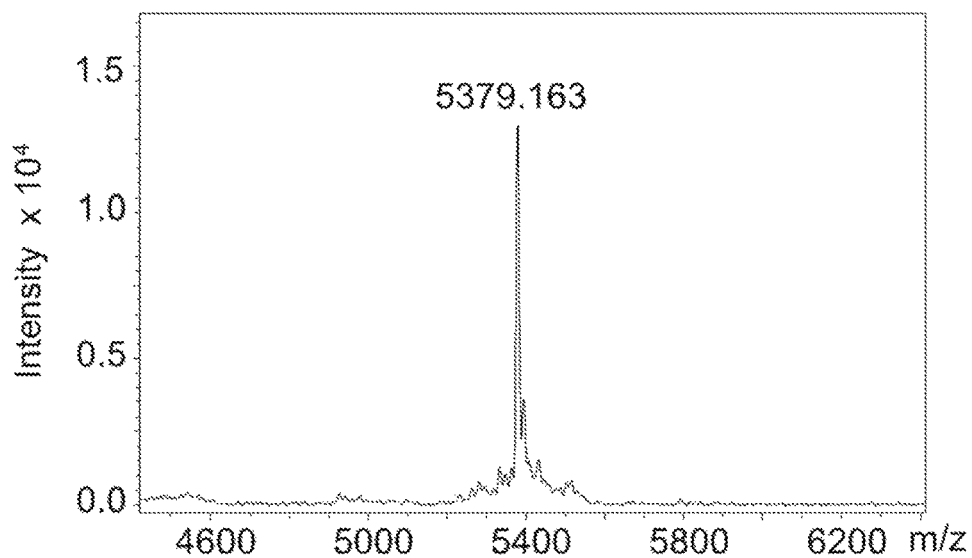

Mass spectrometric analysis shows that the drug bundle of TCO-peptide 2 with fingolimod phosphate had a molecular weight of 5,379.16 Daltons (FIG. 12D). The thus-synthesized drug bundle, as illustrated below, was composed of a linker unit with one free TCO functional group and a set of five fingolimod phosphate molecules as effector elements.

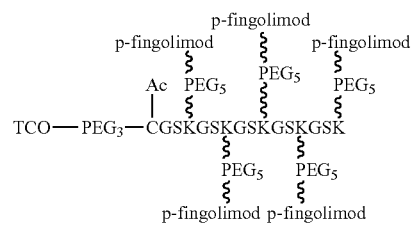

Example 12: Conjugation of NHS-PEG₄-PEG₃-S—S-Conjugated Fingolimod Molecules to TCO-Peptide2

In this example, five NHS-PEG$_4$-PEG$_3$-S—S-conjugated fingolimod molecules were attached to TCO-peptide 2. The conjugation of NHS-PEG$_4$-PEG$_3$-S—S-conjugated fingolimod molecules to the NH$_2$ groups of lysine residues of the TCO-peptide 2 was performed following the protocol set forth in the preceding example. The identification was carried out by mass spectrometry MALDI-TOF.

The thus-synthesized drug bundle, as illustrated below, had a molecular weight of 7,815 Daltons; it was composed of a linker unit with one free TCO functional group and a set of five fingolimod molecules.

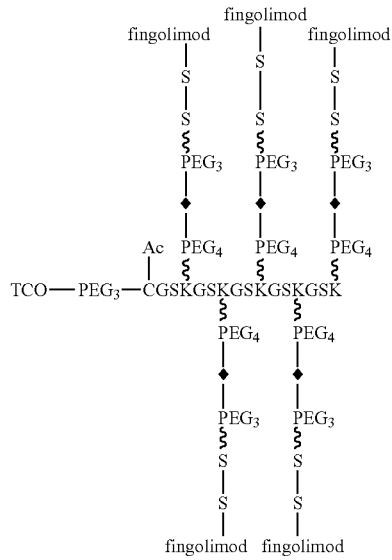

Example 13: Production of Recombinant Human HLA-Al-IgG1.Fc, HLA-A2-IgG1.Fc and PD-1-IgG1.Fc by Expi293F Overexpression System The gene-encoding sequence was placed in pG1K expression cassette. The amino acid sequence of human HLA-A1-IgG1.Fc, HLA-A2-IgG1.Fc and PD-1-IgG1.Fc are set forth in SEQ ID NOs: 27 to 29, respectively.

To prepare recombinant proteins using a mammalian expression system, the overexpression system based on Expi293F™ cell line was used for experimentation. The system employed ExpiFectamine™ 293 transfection kit (Life Technologies, Carlsbad, USA) consisting of the Expi293F™ cell line, the cationic lipid-based Expi-Fectamine™ 293 Reagent and ExpiFectamine™ 293 transfection Enhancers 1 and 2, and the medium, which was part of the expression system (Gibco, New York, USA).

Figure 13A:
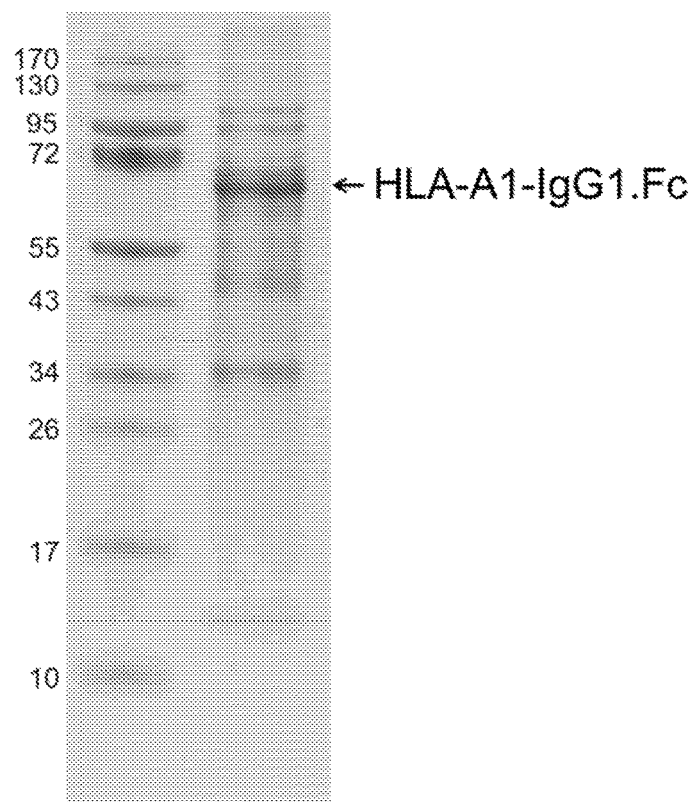
FIGS. 13A to 13C respectively show the SDS-PAGE analysis of purified human HLA-A1-IgG1.Fc, HLA-A2-IgG1.Fc and PD-1-IgG1.Fc fusion protein, according to one working example of the present disclosure.
Figure 13B:
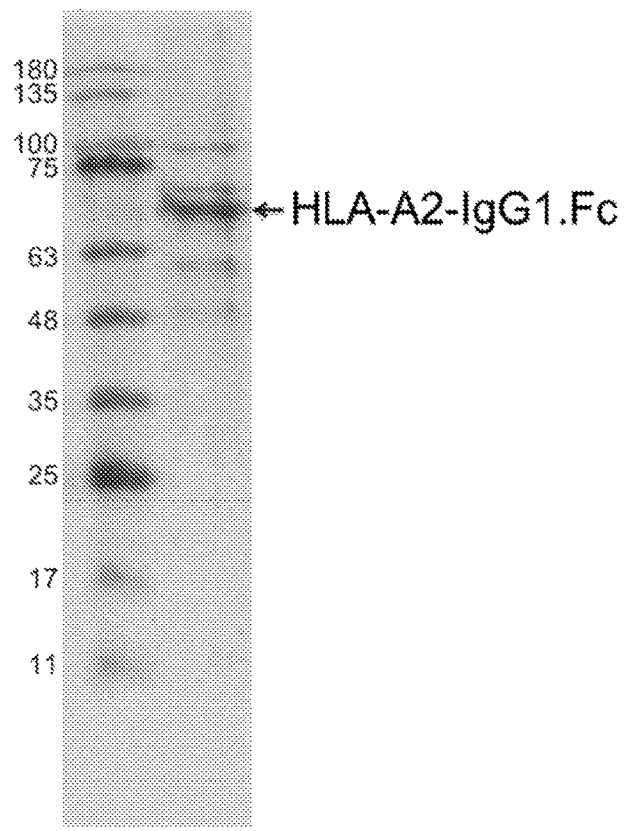
Figure 13C:
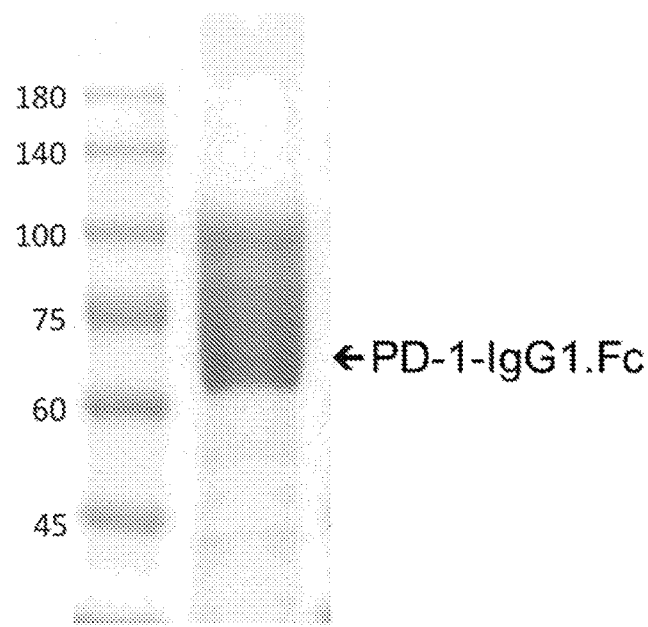

Expi293F cells were seeded at a density of $2.0 \times 10^6$ viable cells/ml in Expi293F expression medium and maintained for 18 to 24 hours prior to transfection to ensure that the cells were actively dividing at the time of transfection. At the time of transfection, $7.5 \times 10^8$ cells in 255-ml medium in a 2-liter Erlenmeyer shaker flask were transfected by Expi-Fectamine™ 293 transfection reagent. The transfected cells were incubated at 37° C. for 16 to 18 hours post-transfection in an orbital shaker (125 rpm) and ExpiFectamine™ 293 transfection enhancer 1 and enhancer 2 were added to the shaker flask, and incubated for 5 to 6 days. Culture supernatants were harvested and scFv proteins in the media were purified using Protein A affinity chromatography. FIGS. 13A, 13B and 13C show SDS-PAGE analysis results of purified human HLA-A1-IgG1.Fc, HLA-A2-IgG1.Fc and PD-1-IgG1.Fc fusion protein (indicated by arrow), respectively.

Example 14: Production of Recombinant Human CTLA-4 and PD-L1 by Expi293F Overexpression System The sequences of the recombinant human CTLA-4 and PD-L1 are provided in SEQ ID NOs: 30 and 31. The two proteins were designed to contain a flexible linker of GGGGSGGGGS and a terminal cysteine residue at the C-terminus.

The expression of the constructed gene in Expi293F cells was performed as in preceding Examples. The expressed CTLA-4 protein in the media was purified using affinity chromatography with immobilized antibody specific for CTLA-4. The expressed PD-L1 protein in the media was purified using affinity chromatography with immobilized PD-1.

Figure 14A:
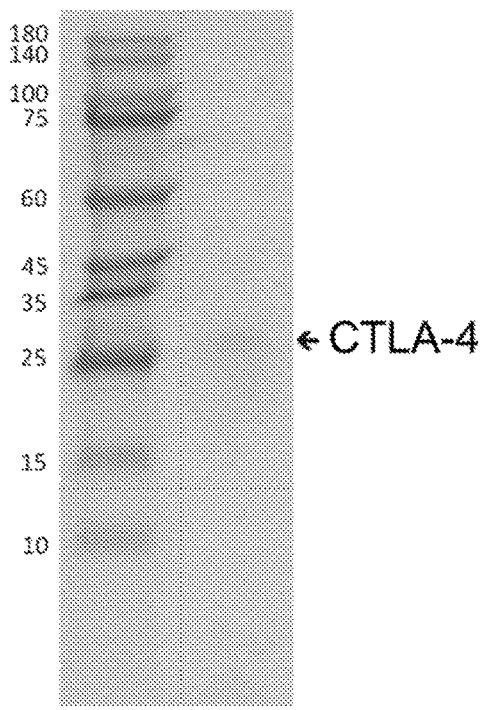
FIGS. 14A and 14B respectively show the SDS-PAGE of purified human CTLA-4 and PD-L1 proteins.
Figure 14B:
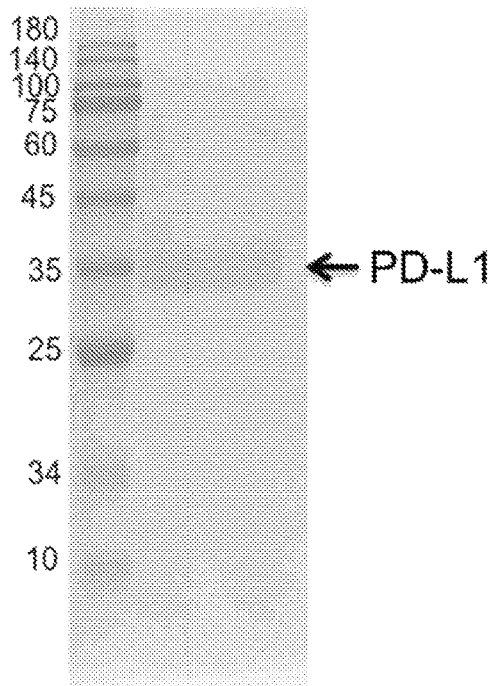

Characterization of the molecular construct was performed with 12% SDS-PAGE. The SDA-PAGE results in FIGS. 14A and 14B show that the purified CTLA-4 and PD-L1 proteins have a size of about 26 and 32 kDa (indicated by arrow), respectively, consistent with the their expected sizes.

Recombinant CTLA-4 protein was analyzed and detected using western blotting. Briefly, 50 μl of the purified CTLA-4 protein was electrophoresed on the 12% SDS-PAGE gel (lane 2) and electroblotted over to a PDVF membrane. The protein (CTLA-4)-IgG1Fc-(scFv α HLA-A1) was used as a positive control (lane 1). After blocking with 5% BSA in TBST at room temperature for 1 hour, the diluted scFv specific for CTLA-4 (1 μg/ml) was added and incubated with the membrane overnight at 4° C. with gentle shaking. The membrane was rinsed and washed 3 times with TBST. The diluted HRP-conjugated protein L (1:5000) was added and incubated with the membrane at room temperature for 1 hour, and the rinse and wash cycle was repeated with TBST for 3 times. The membrane was then incubated with HRP substrate solution for 20 minutes before being exposed to the photographic film.

Figure 14C:
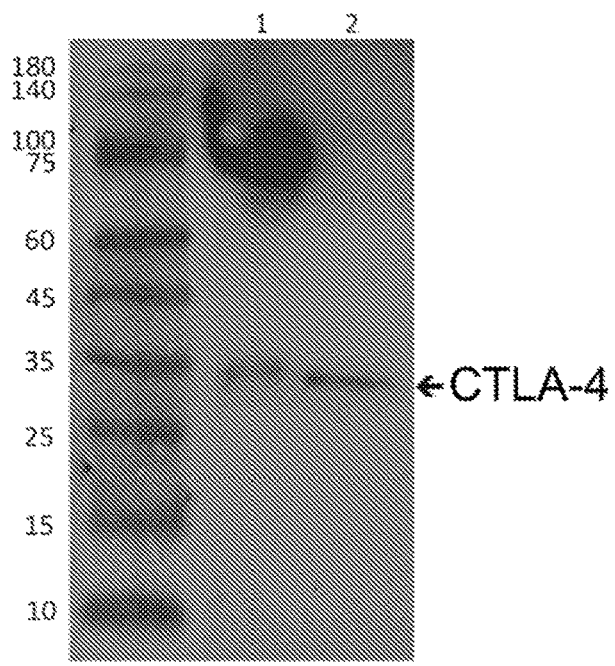
FIG. 14C shows the western blot analysis of purified human CTLA-4.

FIG. 14C shows the western blot results indicating that the recombinant human CTLA-4 can be specifically bound by the scFv specific for CTLA-4 (indicated by arrow of lane 2). The scFv specific for CTLA-4 was prepared in our laboratory described in PCT patent application publication No. WO/2016112870.

Binding activity of recombinant PD-L1 protein was assayed with ELISA using a 96-well plate coated with recombinant PD-L1 protein in 50 μg/ml concentration, 100 μl per well. After the excess PD-L1 was washed off and the solid phase blocked, 100 μl per well of PD1-IgG1.Fc at 50 μg/ml was added. The bound PD1-IgG1.Fc was determined by HRP-conjugated goat anti-human IgG.Fc. 50 μl of TMB substrate was added for color development. The reaction was stopped by 50 μl of 1M HCl. Absorbance at 450 nm was measured with a plate reader. Each bar represents the mean OD450 value of duplicate samples.

Figure 14D:
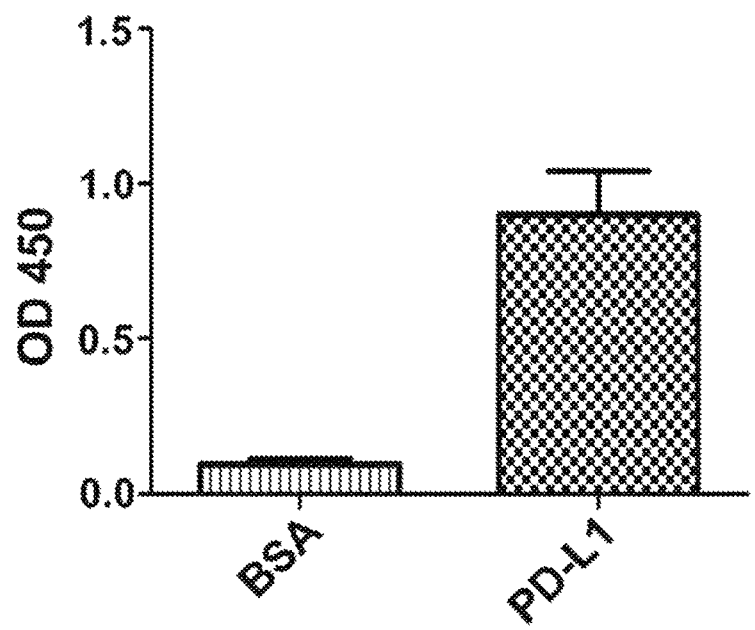
FIG. 14D shows the ELISA analysis of purified human PD-L1 proteins, according to one working example of the present disclosure.

FIG. 14D shows the ELISA results indicating that the recombinant human PD-L1 specifically bound to recombinant PD1-IgG1.Fc.

Example 15: Production of scFv of mAb Specific for HLA-A1 and mAb Specific for CD25 by Expi293F Overexpression System The $V_L$ and $V_H$ of the scFv specific for human HLA-A1 were from monoclonal antibody 4-35-7; the $V_L$ and $V_H$ of the scFv specific for human CD25 were from monoclonal antibody dacilizumab. The scFv derived from those antibodies were designed to contain a flexible linker of GGGGSGGGGS and a terminal cysteine residue at the C-terminus. The cysteine residue provides a sulfhydryl group for conjugation with maleimide group present at the free ends of linking arms in various linker units. To produce the scFv of mAb specific for human HLA-A1 and mAb specific for human CD25, we used the $V_L$ and $V_H$ DNA sequences of the two antibodies with further codon optimization. DNA sequences encoding $V_L$-(GGGGS)$_3$—$V_H$-(GGGGS)$_2$—C were synthesized. The amino acid sequences of the scFv of mAb specific for human HLA-A1, and mAb specific for human CD25 prepared for the experiments of the invention are set forth in SEQ ID NOs: 32 and 33, respectively.

Figure 15A:
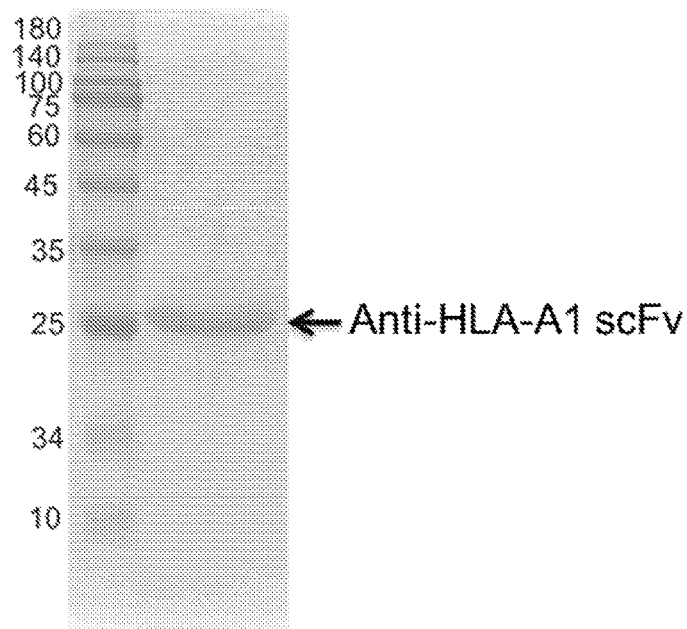
FIGS. 15A to 15C respectively show the SDS-PAGE, mass spectrometric and ELISA analyses of purified scFv of mAb specific for human HLA-A1, according to one working example of the present disclosure.
Figure 15B:
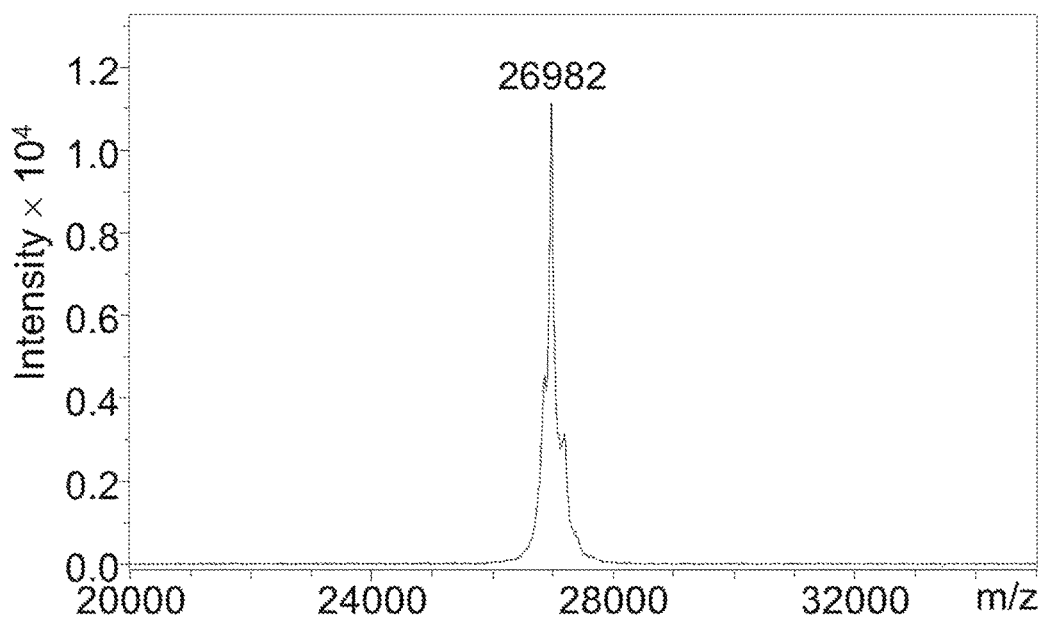
Figure 15C:
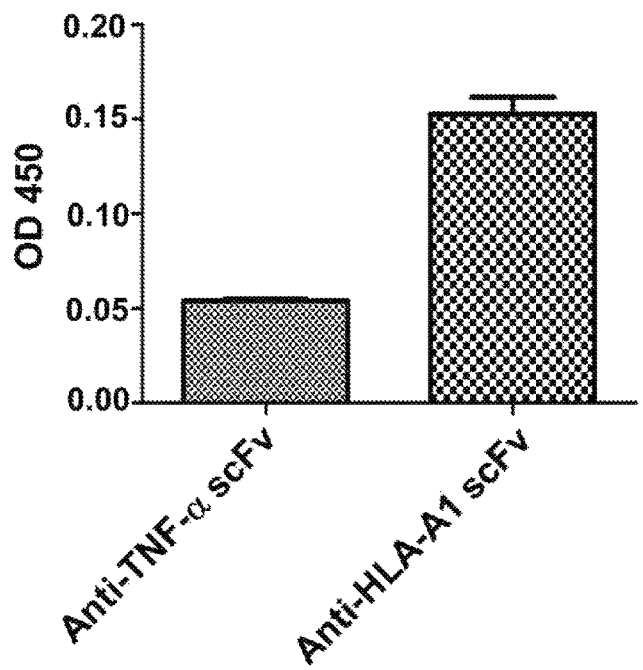

The expression of the constructed gene in Expi293F cells was performed as in preceding Examples. Culture supernatants were harvested and scFv proteins in the media were purified using Protein L affinity chromatography. FIGS. 15A, 15B and 15C show 12% SDS-PAGE, mass spectrometric and ELISA analyses of purified scFv of mAb specific for human HLA-A1. The SDA-PAGE results in FIG. 15A shows that the purified scFv of mAb specific for human HLA-A1 has a size of about 25 kDa (indicated by arrow), consistent with the their expected sizes. The ELISA result in FIG. 15C indicates that the purified scFv of mAb specific for human HLA-A1 bound specifically to human HLA-A1. The scFv specific for TNF-α was used as a negative control, which was prepared as described in PCT patent application publication No. WO/2016112870.

Example 16: Construction and Selection of Phage-Displayed scFvs Specific for Human HLA-A2

The phage clones carrying human scFv specific for human HLA-A2 were obtained through a contractual arrangement with Dr. An-Suei Yang's laboratory at the Genomics Research Center, Academia Sinica, Taipei, Taiwan. The framework sequence of the GH2 scFv library was derived from a human IgG antibody fragment, G6 anti-VEGF Fab (Protein Bank Code 2FJG), and cloned into restriction sites SfiI and NotI of phagemid vector pCANTAB5E (GE Healthcare), carrying an ampicillin resistance, a lacZ promotor, a pelB leader sequence for secretion of scFv fragments into culture supernatants, and an E-tag applicable for detection. The $V_H$ and $V_L$ domains of the scFv template were diversified separately based on the oligonucleotide-directed mutagenesis procedure; the three CDRs in each of the variable domains were diversified simultaneously. The scFv library of over $10^9$ clones was used for selections on human HLA-A2-IgG.Fc fusion protein prepared in the preceding Example.

Maxisorp 96-well plates (Nunc) coated with recombinant human HLA-A2-IgG1.Fc fusion proteins (1 μg/100 μl PBS per well) were used for panning anti-HLA-A2 antibodies. Briefly, the wells were treated with blocking buffer (5% skim milk in PBST (phosphate buffered saline with 0.1% tween-20)) for 1 hour at room temperature. Recombinant phages in the blocking buffer diluted to $6\times10^{11}$ CFU/ml was added to the antigen-coated wells for 1 hour with gentle shaking; CFU stands for colony-forming unit. The wells were then washed vigorously 10 times with PBST, followed by 6 times with PBS to remove nonspecific binding phages. The bound phages were eluted using 0.1 M HCl/glycine buffer at pH 2.2, and the eluted fraction was neutralized immediately by 2 M Tris-base buffer at pH 9.0. *E. coli* strain ER2738 (OD600=~0.6) was used for phage infection at 37° C. for 30 minutes; non-infected *E. coli* was eliminated by treating with ampicillin for 30 minutes. After ampicillin treatment, helper phage M13KO7 carrying kanamycin resistance was added for another one-hour incubation. The selected phages rescued by helper phage in the *E. coli* culture were amplified under vigorously shaking overnight at 37° C. in the presence of kanamycin. The amplified phages were precipitated in PEG/NaCl, and then resuspended in PBS for the next selection-amplification cycle. A total of three consecutive panning rounds were performed on human HLA-A2 by repeating this selection-amplification procedure.

Figure 16A:
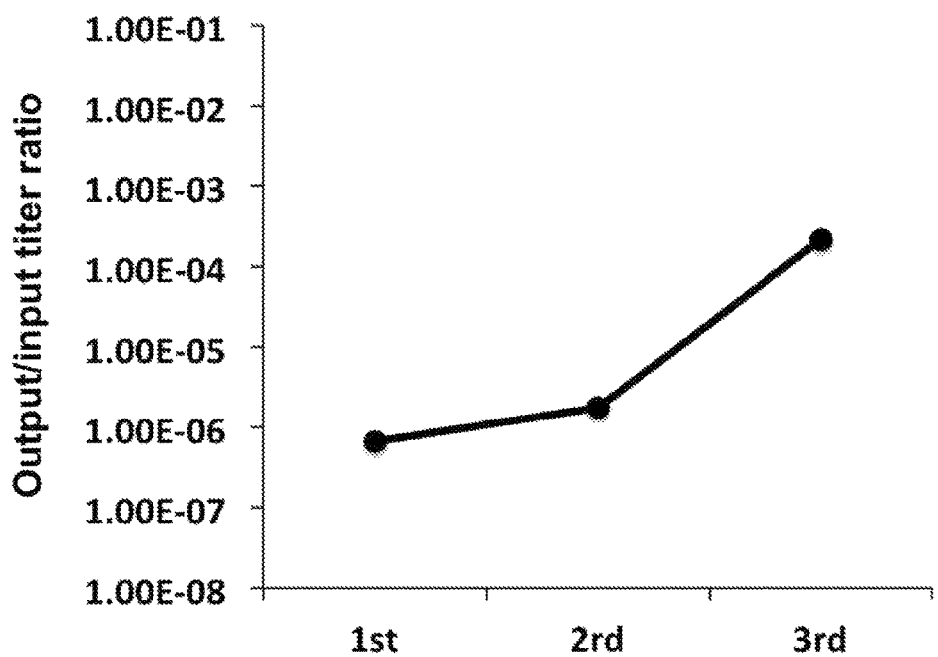
FIGS. 16A and 16B respectively show the titers of the phages bearing scFvs specific for human HLA-A2 and the single colony ELISA analysis of phage-displayed scFvs specific for human HLA-A2, according to one working example of the present disclosure.

Phage-infected ER2738 colonies were enumerated by serial dilution and phage titers were calculated, yielding the output titer/ml (CFU/ml) per panning round. A 2500-fold increase in phage output titer from 4.0E+05 CFU/well to 1.0E+09 CFU/well was obtained after three rounds of panning. The phage output/input titer ratios from each round are shown in FIG. 16A. For each panning round, the phage output/input titer ratios are given on the y-axis. There was clear enrichment of the positive clones over the three rounds of panning. The third panning round resulted in a 300-fold increase in the ratios of phage output/input titer over the first round, as the binding clones became the dominant population in the library.

Example 17: Single Colony ELISA Analysis of Phage-Displayed scFvs Specific for Human HLA-A2

*E. coli* strain ER2738 infected with single-clonal phages each harboring a selected scFv gene in its phagemid was grown in the mid-log phase in 2YT broth (16 g/l tryptone, 10 g/l yeast extract, 5 g/l NaCl, pH 7.0) with 100 μg/ml ampicillin in deep well at 37° C. with shaking. After the broth reached an OD600 of 1.0, IPTG was added to a final concentration of 1 μg/ml. The plates were incubated at 37° C. overnight under rigorously shaking. Thereafter, the plates were centrifuged at 4,000 g for 15 minutes at 4° C.

For soluble scFv binding test, ELISA was carried out. Briefly, 96-well Maxisorp 96-well plate (Nunc) was coated with human HLA-A2 (0.5 μg/100 μl PBS per well) or two negative control antigens, human heat shock protein 70 (Hsp 70) and RSV-IgG1.Fc fusion protein (prepared by our laboratory), for 18 hours with shaking at 4° C. After being treated with 300 μl of blocking buffer for 1 hour, 100 μl of secreted scFv in the supernatant was mixed with 100 μl of blocking buffer and then added to the coated plate for another 1 hour. Goat anti-E-tag antibody (conjugated with HRP, 1:4000, Cat. No. AB19400, Abcam) was added to the plate for 1 hour. TMB substrate (50 μl per well) was added to the wells and the absorbance at 450 nm was measured after reactions were stopped by adding 1N HCl (50 μl per well).

Figure 16B:
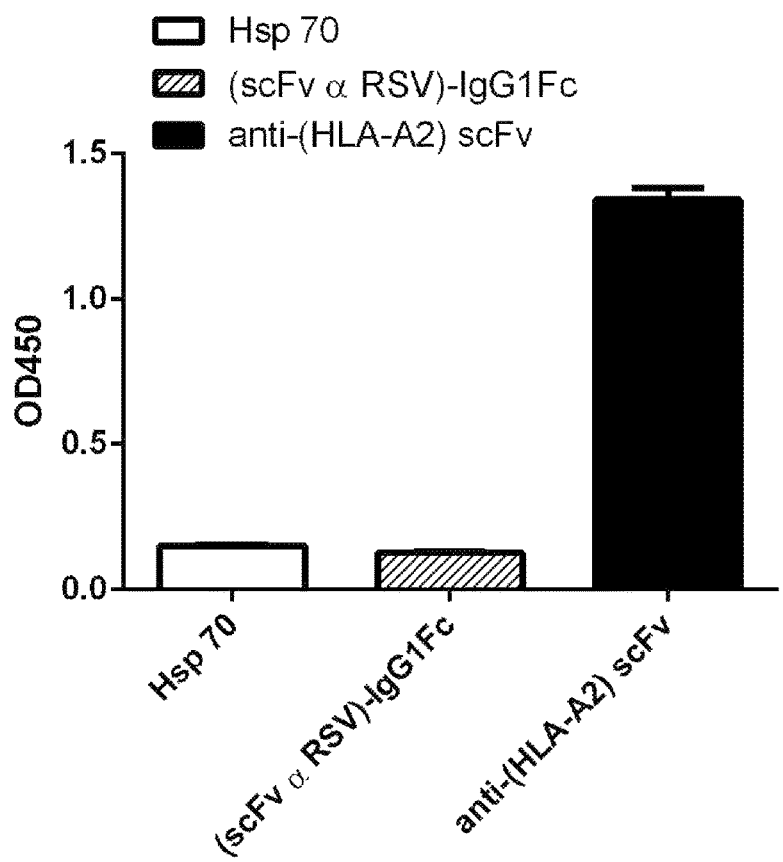

A total of 192 phage clones after the $3^{rd}$ round of panning were subjected to the present analysis. Among them, 12 scFv clones that bound to HLA-A2 with a differential of OD450 greater than 10 were further characterized by DNA sequencing of their encoding scFv genes. Eight different DNA sequences were identified. FIG. 16B shows the ELISA result of one scFv clone, 3E10. The amino acid sequence of the scFV clone 3E10, which binds to human HLA-A2 with an OD450 of 1.3, is provided in SEQ ID NO: 34.

Example 18: Preparation of Tetrazine-scFv Specific for Human HLA-A1

The DNA sequence encoding the scFv specific for human HLA-A1 (SEQ ID NO: 32) was synthesized and expressed as in the above Examples. For the conjugation with Mal-PEG$_4$-tetrazine (Conju-probe, Inc.), the cysteine residue at the C-terminal end of the purified scFv of mAb specific for human HLA-A1 was reduced by incubating with 10 μM TCEP at room temperature for 4 hours with gentle shaking.

The buffer of reduced scFv proteins were exchanged to sodium phosphate buffer (100 mM sodium phosphate, pH 7.0, and 50 mM NaCl) using NAP-10 Sephadex G-25 column. After the reduction reaction and buffer exchange, conjugation was conducted overnight at 4° C. in a reaction molar ratio of 10:1 ([Mal-PEG$_4$-tetrazine:[scFv]]. The excess crosslinker was removed by a desalting column and the tetrazine-conjugated scFv products were analyzed.

Figure 17A:
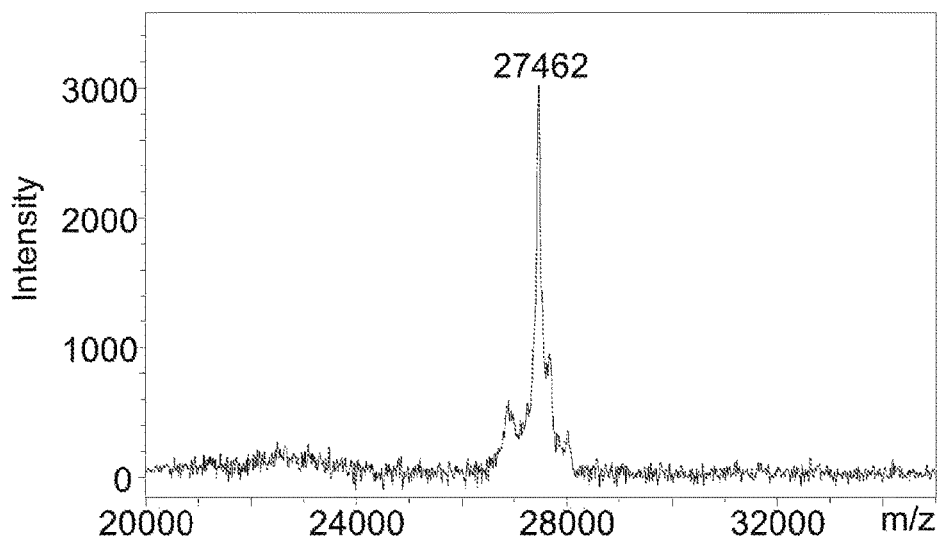
FIG. 17A and FIG. 17B respectively show the mass spectrometric and ELISA analysis of tetrazine-conjugated scFv specific for human HLA-A1, according to one working example of the present disclosure.
Figure 17B:
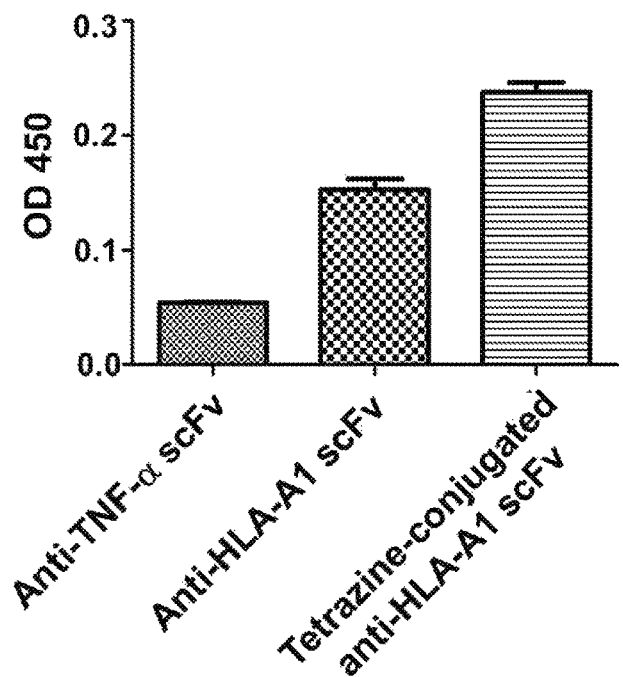

The results of mass spectroscopy MALDI-TOF analysis indicated that the sample of tetrazine-conjugated scFv specific for human HLA-A1 had a molecular weight of 27,462 Daltons. The purity of tetrazine-conjugated scFv specific for human HLA-A1 was identified through Coomassie blue staining of 12% SDS-PAGE. FIGS. 17A and 17B show, respectively, the mass spectrometric and ELISA analysis of tetrazine-conjugated scFv specific for human HLA-A1, in which unmodified scFv specific for human HLA-A1 was used as a positive control. The ELISA results establish that the tetrazine-conjugated scFv specific for human HLA-A1 bound to recombinant HLA-A1.

Example 19: Conjugation of Three CTLA-4 Molecules to Three Maleimide-PEG$_{12}$ Linking Arms Based on TCO-Peptide 1

Prior to being conjugated with the TCO-peptide 1 that had three maleimide-PEG$_{12}$ linking arms, CTLA-4 was incubated with TCEP at a molar ratio of 2:1 ([TCEP]:[protein]) at room temperature for 4 hours under gentle shaking to keep its C-terminal cysteine in the reduced form. Subsequently, the buffer of the reduced CTLA-4 protein was exchanged to maleimide-SH coupling reaction buffer (100 mM sodium phosphate, pH 7.0, and 50 mM NaCl) using an NAP-10 Sephadex G-25 column (GE Healthcare). After the reduction and buffer exchange, the conjugation to the TCO-peptide 1 having three maleimide-PEG$_{12}$ linking arms was conducted overnight at room temperature at a molar ratio of 1:4 ([linker]:[Protein]).

The reaction mixture was applied to a size exclusion chromatography column S75. The PEG$_{12}$-maleimide-conjugated TCO-peptide 1 conjugated with three CTLA-4 molecules was separated from the free CTLA-4, free PEG$_{12}$-maleimide-conjugated TCO-peptide 1 and the PEG$_{12}$-maleimide-conjugated TCO-peptide 1 conjugated with one and two CTLA-4 molecules by size exclusion chromatography column S75. The purified product, maleimide-PEG$_{12}$-conjugated TCO-peptide 1 conjugated with three CTLA-4 molecules, was concentrated and buffer-exchange into click reaction buffer, 100 mM potassium phosphate at pH 7.0.

Illustrated below is the thus-synthesized effector linker unit that was composed of a linker unit with one free TCO functional group and a set of three CTLA-4 molecules as effector elements.

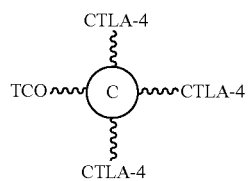

Example 20: SDS-PAGE Analysis of Effector Linker Unit Containing Three CTLA-4 Molecules Linked to Three Maleimide-PEG$_{12}$ Linking Arms Based on TCO-Peptide 1

The sample of the effector linker unit having three CTLA-4 molecules linked to the three maleimide-PEG$_{12}$ linking arms based on TCO-peptide 1 was analyzed by 8% SDS-PAGE. The size of the experimental molecular weight was consistent with the size of theoretical molecular weight of three CTLA-4 molecules conjugated to TCO-peptide 1 with three maleimide-PEG$_{12}$ linking arms. The SDS-PAGE analysis of the reaction mixtures of TCO-peptide 1 with three maleimide-PEG$_{12}$ linking arms after the conjugation with CTLA-4 molecules. The product was subjected to 10% SDS-PAGE analysis, and the result indicated a weak band corresponding to TCO-peptide 1 conjugated with three CTLA-4 molecules.

Example 21: Preparation of Effector Linker Unit Based on TCO-Peptide 1 with Three PD-L1 Molecules or Three scFvs Specific for Human CD25 Molecule The conjugation of human PD-L1 to the linker unit and the purification and analysis of the product were performed per the protocols set forth in the preceding Examples.

Figure 18:
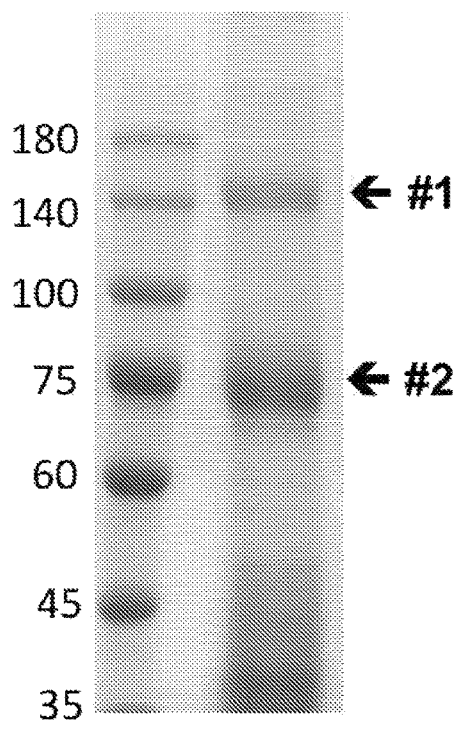
FIG. 18 show the 10% SDS-PAGE analysis of an effector linker-unit, composed of a linker-unit with a free TCO functional group and a set of three three PDL-1 molecules as effector elements, according to one working example of the present disclosure.

FIG. 18 shows the 10% SDS-PAGE analysis of the reaction mixtures of TCO-peptide 1 with three maleimide-PEG$_{12}$ linking arms after the conjugation with PD-L1 molecules (lane 1). Arrow #1 and #2 were TCO-peptide 1 conjugated with three and two PD-L1 molecules, respectively.

The sample of the effector linker unit of three PD-L1 linked to the three maleimide-PEG$_{12}$ linking arms based on TCO-peptide 1 was analyzed by MALDI-TOF. The median of the experimental molecular weight was consistent with the median of theoretical molecular weight of three PD-L1 conjugated to TCO-peptide 1 with three maleimide-PEG$_{12}$ linking arms. Illustrated below is the thus-synthesized effector linker unit that was composed of a linker unit with one free TCO functional group and a set of three PD-L1 molecules as effector elements.

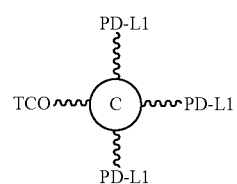

The conjugation of scFv specific for human CD25 to the linker unit and the purification and analysis of the product were performed per the protocols set forth in the preceding Examples.

Illustrated below is the thus-synthesized effector linker unit that was composed of a linker unit with one free TCO functional group and a set of three scFvs specific for the extracellular domain of human CD25 as effector elements.

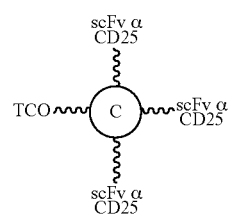

Example 22: Preparation of Molecular Construct with One scFv Specific for HLA-A1 as Targeting Elements and Three CTLA-4 Molecules as Effector Element In this example, the effector linker unit of the preceding examples and a tetrazine-conjugated scFv specific for human HLA-A1 was coupled via a tetrazine-TCO iEDDA reaction. Specifically, the effector linker unit had three CTLA-4 molecules and one free TCO group.

The procedure for tetrazine-TCO ligation was performed per the manufacturer's instructions (Jena Bioscience GmbH, Jena, Germany). Briefly, 100 µl of the targeting linker unit (0.3 mg/ml) was added to the solution containing the effector element at a molar ratio of 1.2:1 ([tetrazine]:[TCO]). The reaction mixture was incubated for 3 hour at room temperature.

In the mass spectrometric analysis, the median of the experimental molecular weight was consistent with the median of theoretical molecular weight of the resultant joint-linker molecular construct. Illustrated below is the resultant single-linker molecular construct with one scFv specific for human HLA-A1 as targeting element and with three CTLA-4 molecules as effector elements.

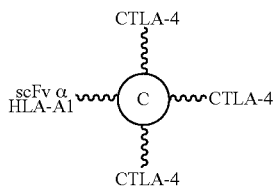

Example 23: Preparation of Molecular Construct with One scFv Specific for HLA-A1 as Targeting Elements and Three PD-L1 Molecules as Effector Element In this example, the effector linker unit of the preceding examples and a tetrazine-conjugated scFv specific for human HLA-A1 was coupled via a tetrazine-TCO iEDDA reaction. Specifically, the effector linker unit had three PD-L1 molecules and one free TCO group. The procedure for tetrazine-TCO ligation was the same as in the preceding Examples.

Illustrated below is the resultant single-linker molecular construct with one scFv specific for human HLA-A1 as targeting element and with three PD-L1 molecules as effector elements.

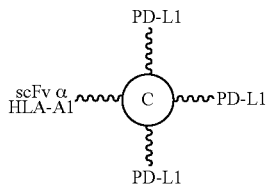

Figure 19:
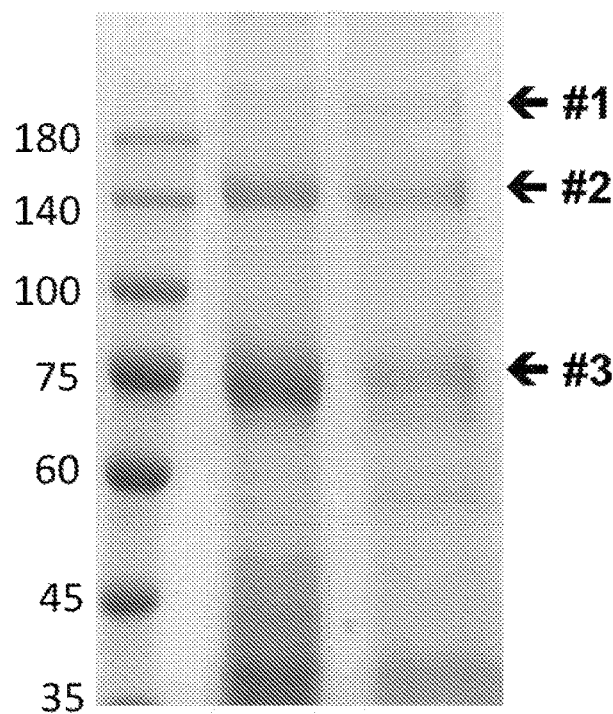
FIG. 19 shows the 10% SDS-PAGE analysis of a single linker unit molecular construct with one scFv specific for HLA-A1 as targeting element and three PD-L1 molecules as an effector element, according to one working example of the present disclosure.

FIG. 19 shows 10% SDS-PAGE analysis of the reaction mixtures of resultant single-linker molecular construct with one scFv specific for human HLA-A1 as targeting element and with three PD-L1 molecules as effector elements (lane 2). The lane 1 showed that the reaction mixtures of TCO-peptide 1 with three maleimide-PEG$_{12}$ linking arms after the conjugation with PD-L1 molecules. Arrow #1 (lane 2) was the single-linker molecular construct with one scFv specific for human HLA-A1 as targeting element and with three PD-L1 molecules as effector elements. Arrow #2 and #3 were respectively TCO-peptide 1 conjugated with three and two PD-L1 molecules.

Example 24: Preparation of Molecular Construct with One scFv Specific for HLA-A1 as Targeting Elements and Three scFvs Specific for Human CD25 as Effector Element In this example, the effector linker unit of the preceding examples and a tetrazine-conjugated scFv specific for human HLA-A1 was coupled via a tetrazine-TCO iEDDA reaction. Specifically, the effector linker unit had three scFvs specific for the extracellular domain of human CD25 and one free TCO group. The procedure for tetrazine-TCO ligation was the same as in the preceding Examples.

Illustrated below is the resultant joint-linker molecular construct with one scFv specific for human HLA-A1 as targeting element and with three scFvs specific for the extracellular domain of human CD25 as effector elements.

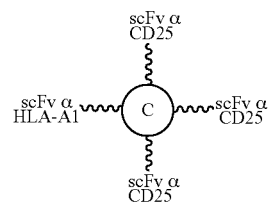

Example 25: Preparation of Molecular Construct with One scFv Specific for HLA-A1 as Targeting Element and Five Sirolimus-Gly Molecules as Effector Elements In this example, the molecular construct with one scFv specific for human HLA-A1 and a drug bundle of five sirolimus-Gly molecules was constructed. The molecular construct was made by a TCO-tetrazine iEDDA reaction. The procedure for tetrazine-TCO ligation was the same as in the preceding Examples.

The MALDI-TOF mass spectrometric analysis showed that the median of the experimental molecular weight was consistent with the median of theoretical molecular weight of the resultant joint-linker molecular construct. The product, as illustrated below, was the molecular construct with one scFv specific for human HLA-A1 and one drug bundle bearing five sirolimus-Gly molecules.

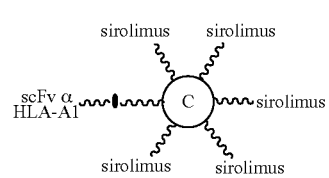

Example 26: Preparation of Molecular Construct with One scFv Specific for HLA-A1 as a Targeting Element and Five Fingolimod Molecules as Effector Elements In this example, the molecular construct with one scFv specific for human HLA-A1 and a drug bundle of five fingolimod molecules was constructed. The molecular construct was made by a TCO-tetrazine iEDDA reaction. The procedure for tetrazine-TCO ligation was the same as in the preceding Examples.

The median of the experimental molecular weight was consistent with the median of theoretical molecular weight of the resultant joint-linker molecular construct. The product, as illustrated below, was the molecular construct with one scFv specific for human HLA-A1 and one drug bundle bearing five fingolimod molecules.

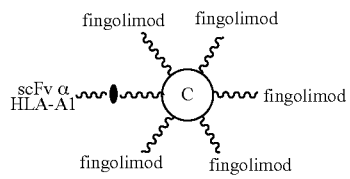

Example 27: Assay of Biological Activity of Sirolimus Upon Conjugation with NHS—S—S-PEG$_3$-Azido Linking Arm Mammalian target of rapamycin (mTOR) is a protein kinase that controls T cell activation and proliferation. Sirolimus, also known as rapamycin, inhibits mTOR indirectly by binding to immunophilin, FK binding protein (FKBP12). The complex of rapamycin and FKBP12 then interacts with mTOR and inhibits the function to phosphorylate its downstream target, p70 S6 Kinase (p70S6K), leading to inhibition of cell activation and proliferation.

The syntheses of these modified sirolimus molecules (sirolimus-Gly, sirolimus-diGly and azido-PEG$_3$-S—S-conjugated sirolimus-Gly) have been shown in the preceding examples. To examine the biological activities of these compounds, western blot analysis of mTOR/p70S6K signaling pathway and T-cell proliferation assay were performed with human Jurkat T cells. T-cell viability and proliferation were assessed using alamarBlue® cell viability reagent (Invitrogen).

For the western blot analysis of mTOR/p70S6K signaling pathway, briefly, Jurkat T cell were seeded into 6-cm cell culture dish in RPM11640 medium containing 10% fetal bovine serum. After 1 hour, cells were co-treated with 10 ng/ml of IL2 and 100 nM of sirolimus, sirolimus-Gly, azido-PEG$_3$-S—S-conjugated sirolimus-Gly, and sirolimus-diGly for 24 hours.

The cells were then lysed in gold lysis buffer, containing 30 mM Tris-HCl, (pH 7.9), 5 mM EGTA, 137 mM NaCl, 15% glycerol, 1% Triton X-100, and 1×protease inhibitor cocktail. Insoluble material was collected by centrifugation at 14,000×g for 20 minutes at 4° C. The cell lysate samples were separated on 10% SDS-PAGE gels and transferred to a PVDF membrane (Millipore). The membrane blots were blocked in PBS containing 5% BSA for 1 hour at room temperature, and incubated with primary antibodies, anti-phospho-p70S6K antibody (Cell Signaling Technology, Danvers, USA) and anti-p70S6K antibody (Cell Signaling Technology), overnight at 4° C. After washing three times with TBST containing 20 mM Tris-HCl (pH 7.6), 0.8% (w/v) NaCl and 0.25% Tween-20, the blots were incubated with goat anti-mouse IgG.Fc antibody conjugated with horseradish peroxidase (Millipore). Then the membranes were washed three times with TBST, and immunoreacted bands were detected with ECL™ western blotting detection reagents (Millipore) and exposed on Fujifilm (Tokyo, Japan). Relative quantification of ECL signals on X-ray films were analyzed by using Image J (NIH, Bethesda, Md., USA).

Figure 20A:
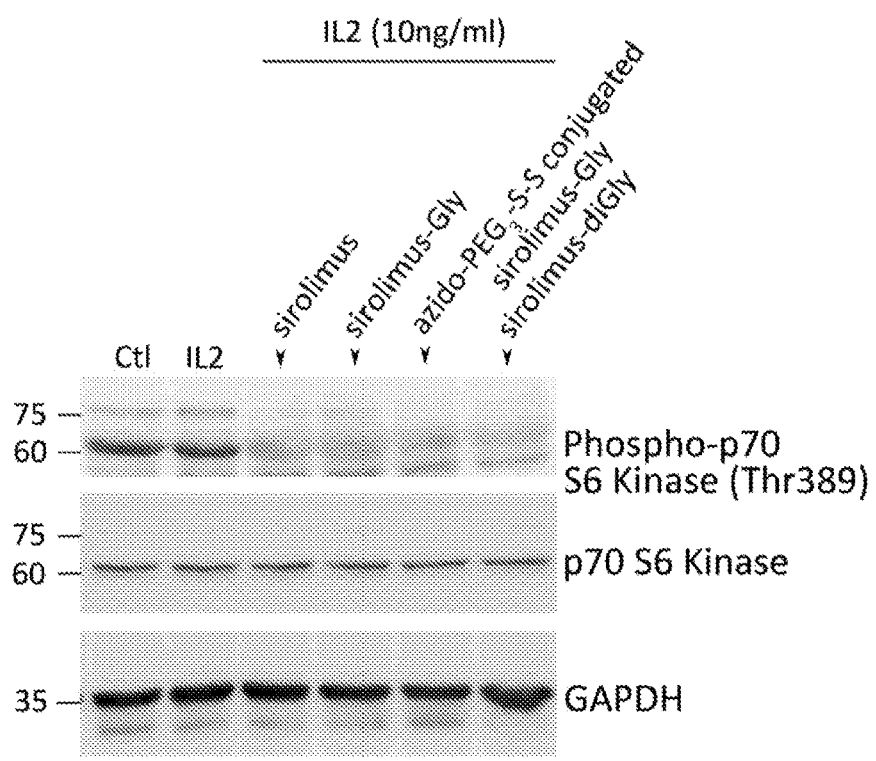
FIG. 20A and FIG. 20B respectively show the mTOR inhibition and T-cell proliferation assay of sirolimus and sirolimus derivative compounds, according to one working example of the present disclosure.

FIG. 20A shows the effect of sirolimus, sirolimus-Gly, sirolimus-diGly and azido-PEG$_3$-S—S-conjugated sirolimus-Gly on mTOR protein in Jurkat T cells by western blot analysis. As showed in FIG. 20A, the phosphorylated level of p70S6K was decreased in the cells treated with sirolimus and sirolimus derivative compounds, without changes in the total p70S6K protein level. The result indicates that the mTOR/p70S6K signally pathway in the treated T cells was blocked by sirolimus derivative compounds, having a similar effect as the unmodified sirolimus.

For T-cell proliferation assay, Jurkat T cells ($2*10^4$/well) were seeded into 96-well plates in RPMI1640 medium containing 10% fetal bovine serum. After 1 hour, cells were treated with or without 10 ng/ml of IL2. After incubating for 24 hours, cells were then treated with different concentrations (2 folds dilution from 200 nM) of sirolimus, sirolimus-Gly, azido-PEG$_3$-S—S-conjugated sirolimus-Gly, and sirolimus-diGly for 24 hours, 48 hours, and 72 hours. Cells viability was determined by alamarBlue cell viability reagent kit (Invitrogen), in accordance with the manufacturer's instruction.

Figure 20B:
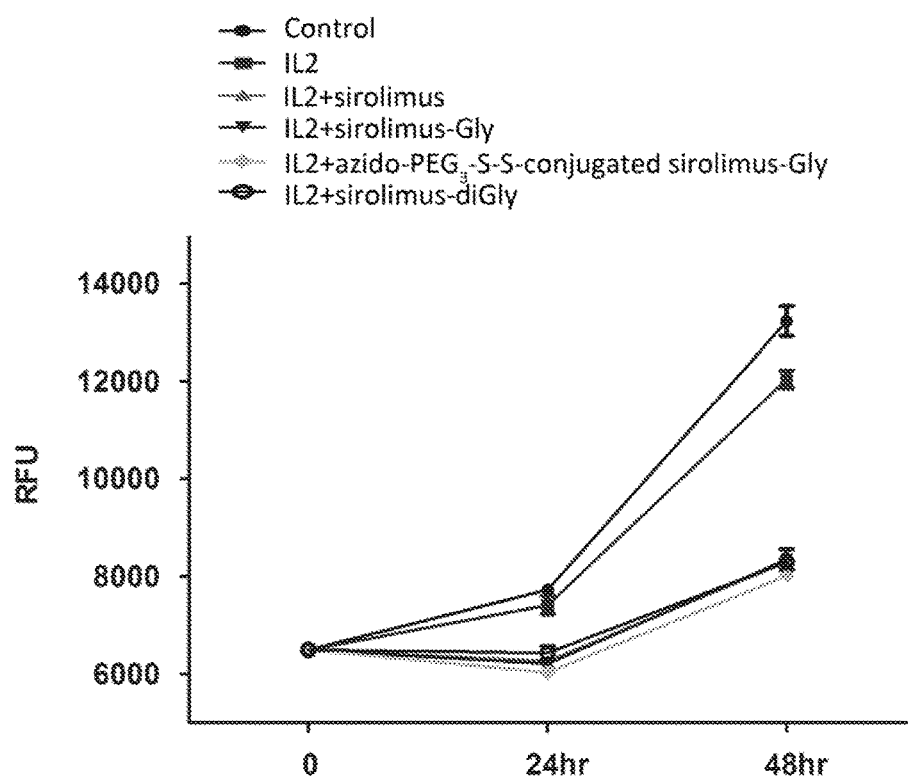

FIG. 20B shows the assay results of the biological activity of sirolimus, sirolimus-Gly, sirolimus-diGly and azido-PEG$_3$-S—S-conjugated sirolimus-Gly. The result indicates that the sirolimus derivative compounds had similar biological activity to inhibit mTOR activity as the unmodified sirolimus.

Example 28: Assay of Biological Activity of Fingolimod Upon Conjugation to Peptide Core Through Linking Arms Fingolimod has been used as a functional antagonist of shingosine-1 phosphate (S1P) receptor-1 (S1P$_1$) function, thereby cells expressing S1P$_1$ receptors that are pretreated with fingolimod are rendered unresponsive to subsequent S1P stimulation (Pedro J. et al., 2012). Fingolimod's capacity to modulate S1P$_1$ function rely on its ability to rapidly internalize S1P1 from a membrane to a cytoplasmic compartment, thus rendering cells unable to respond to external S1P signals. Recent data has been shown that the phosphorylated form of fingolimod binds to S1P receptors and blocks T and B lymphocyte egress and circulation.

The syntheses of these modified fingolimod molecules (NHS-PEG$_5$-conjugated fingolimod and the drug bundle with one free TCO functional group and with five fingolimod molecules) have been shown in the preceding examples. To examine the biological activities of the three compounds, S1P-driven Transwell migration assay was performed with human primary B cells isolated from human PBMC (peripheral blood mononuclear cells).

In the preparation of human primary B cells, human B cells were isolated from human PBMC (peripheral blood mononuclear cells) by B cell isolation kit (Myltenyi Biotech). The isolated B cells were seeded and maintained in a 15-cm dish in IMDM medium supplemented with 10% fetal bovine serum (Gibco) and 20 ng/ml IL2 (Peprotech Inc.).

Figure 21A:
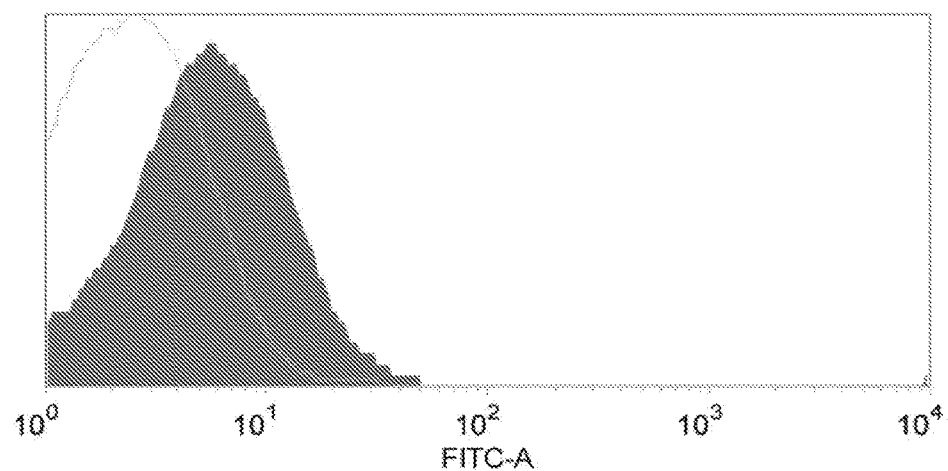
FIG. 21A shows the staining analysis of the S1P1 receptor-expressing human B cells.

FIG. 21A shows that staining analysis of the isolated S1P$_1$ receptor-expressing human B cells, 2×10$^5$ B cells were incubated with 10 µg/ml of anti-S1P$_1$ receptor antibody (AbD Serotec) in PBS containing 1% BSA on ice for 30 minutes. Cells were washed and incubated with FITC-conjugated goat anti-mouse IgG, diluted 1:200 in PBS/BSA, on ice for 30 minutes in the dark. The cells were then analyzed by FACS (FACSCanto II, BD Biosciences).

For chemotaxis assays, 100 µl of the maintained human B cells (4×10$^5$ cells) were transferred into 1.5-ml Eppendorf tube and added fingolimod, fingolimod phosphate, NHS-PEG$_5$-conjugated fingolimod, and the drug bundle with one free TCO functional group and with five fingolimod molecules, respectively, at a final concentration of 1 and 10 µM at 37° C. for 4 hours. Subsequently, the treated B cells of 100 µl were added to the upper chamber of a 6.5 mm Trans-well with 5 µm pore polyester membrane insert (Corning), and the lower chamber of the Trans-well had contained 500 µl of IMDM medium with S1P at a final concentration of 10 nM. After 3 hours, the migrated cells in the lower chambers were collected and further stained with trypan blue and counted by hemocytometer. For each measurement, the specific migration was calculated as follows: [(Number of cells in lower chamber)/(Number of cells in lower+upper chamber)×100]−(cell migration percentage at 0 nM attractant)]. The result of the percentage of specific migrated cells is shown in FIG. 21B.

Figure 21B:
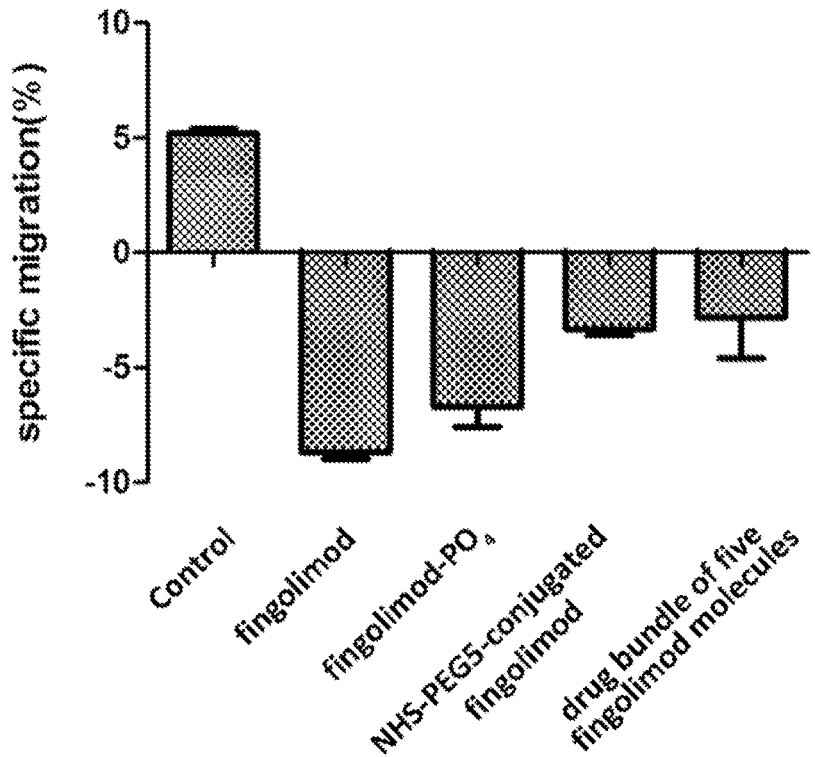
FIG. 21B shows transwell migration assay of fingolimod upon the conjugation to peptide core through linking arms, according to one working example of the present disclosure.

FIG. 21B shows the assay results of the biological activity of NHS-PEG$_5$-conjugated fingolimod and the drug bundle with one free TCO functional group and with five fingolimod molecules. The result indicates that the fingolimod molecule conjugated with a linking arm had similar biological activity to block B-cell migration as the unmodified fingolimod.

Example 29: Construction of a Gene Segment Encoding 2-Chain IgG1.Fc Fusion Protein Containing CTLA-4 and scFv Specific for HLA-A1

Abatacept is a fusion protein composed of the Fc region of the human IgG1 fused to the extracellular domain of CTLA-4. The 2-chain IgG.Fc fusion protein was prepared by configuring abatacept-(scFv α HLA-A1) in a recombinant chain. The C-terminal of the abatacept was fused to the N-terminal of the scFv 4-35-7 specific for human HLA-A1 via a flexible linker, (GGGGS)$_2$.

The scFv (specific for human HLA-A1) had an orientation of V$_L$-linker-V$_H$. The V$_L$ and V$_H$ in the scFv were connected by a hydrophilic linker, (GGGGS)$_3$. The sequence of the recombinant chain in the IgG1.Fc fusion protein molecular construct is shown as SEQ ID NO: 35.

Illustrated below is the configuration of the prepared 2-chain CTLA-4-hIgG1.Fc-(scFv α HLA-A1) molecular construct

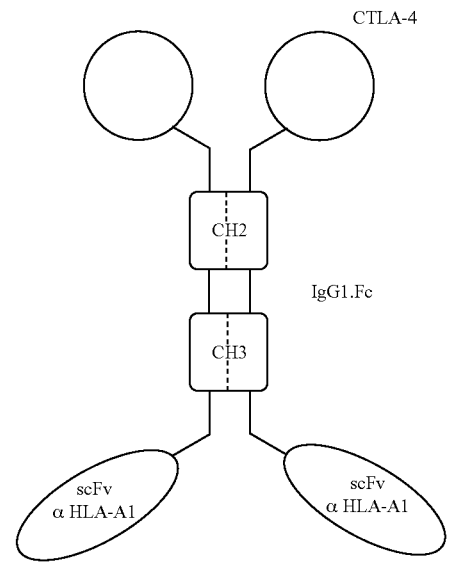

Figure 22A:
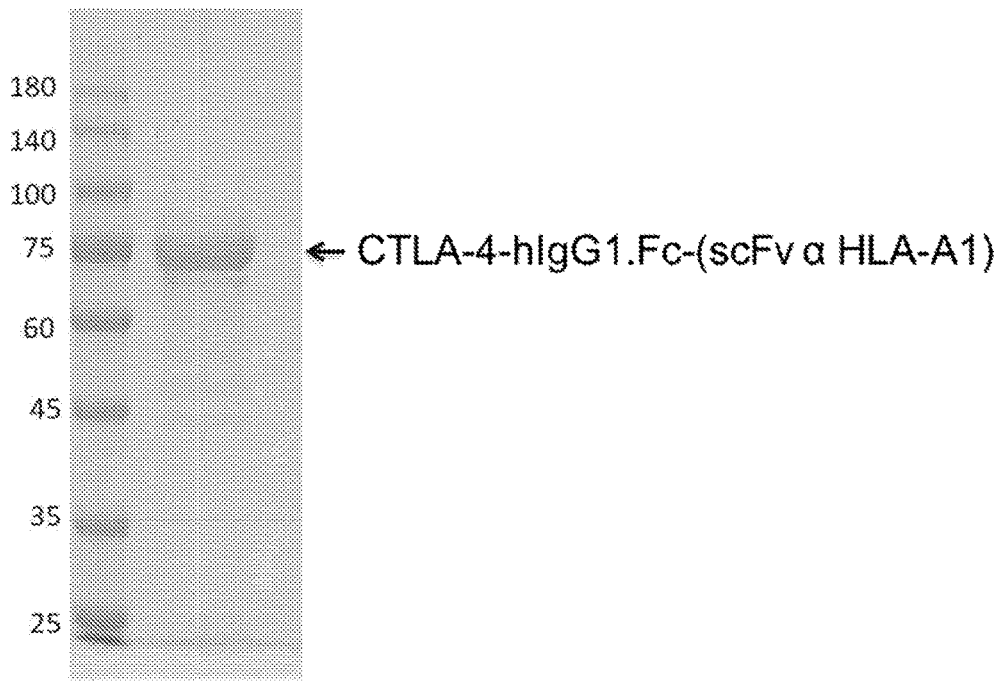
FIG. 22A shows the SDS-PAGE analysis of purified recombinant 2-chain (CTLA-4)-IgG1.Fc-(scFv α HLA-A1) fusion protein.

Example 30: Expression and Purification of Recombinant 2-Chain CTLA-4-hIgG1.Fc-(scFv α HLA-A1) Fusion Protein In this Example, the gene-encoding sequence was placed in pcDNA3 expression cassette. Expi293F cells were seeded at a density of 2.0×10$^6$ viable cells/ml in Expi293F expression medium and maintained for 18 to 24 hours prior to transfection to ensure that the cells were actively dividing at the time of transfection. At the time of transfection, 7.5×10$^8$ cells in 255-ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for 7 days. Culture supernatants were harvested and recombinant 2-chain CTLA-4-hIgG1.Fc-(scFv α HLA-A1) fusion protein in the media was purified using Protein A chromatography. Following buffer exchange to PBS, the concentration of CTLA-4-hIgG1.Fc-(scFv α HLA-A1) protein was determined and analyzed by 8% SDS-PAGE shown in FIG. 22A. The Fc-fusion molecular construct was revealed as the major band indicated by arrow at about 72 kDa (indicated by arrow), consistent with the expected size.

Example 31: ELISA Analysis of the Binding of Recombinant 2-Chain CTLA-4-hIgG1.Fc-(scFv α HLA-A1) Fusion Protein Binding activity of recombinant CTLA-4-hIgG1.Fc-(scFv α HLA-A1) to was assayed by ELISA using a 96-well plate coated with recombinant CTLA-4-hIgG1.Fc-(scFv α HLA-A1) protein in 5 µg/ml concentration, 100 µl per well. The (scFv α endotoxin)-hIgG1.Fc-(scFv α CD32a) prepared by our laboratory is used as a negative control.

After treated with 200 µl of blocking buffer for 1 hour, 100 µl of anti-CTLA-4 scFv was added to the coated plate for another 1 hour. Then, HRP-conjugated Protein L (1:5000) was added to the coated plate for 1 hour. Next, 50 µl of TMB substrate was added for color development. The reaction was stopped by 50 µl of 1M HCl. Absorbance at 450 nm was measured with a plate reader. Each bar represents the mean OD450 value of duplicate samples.

Figure 22B:
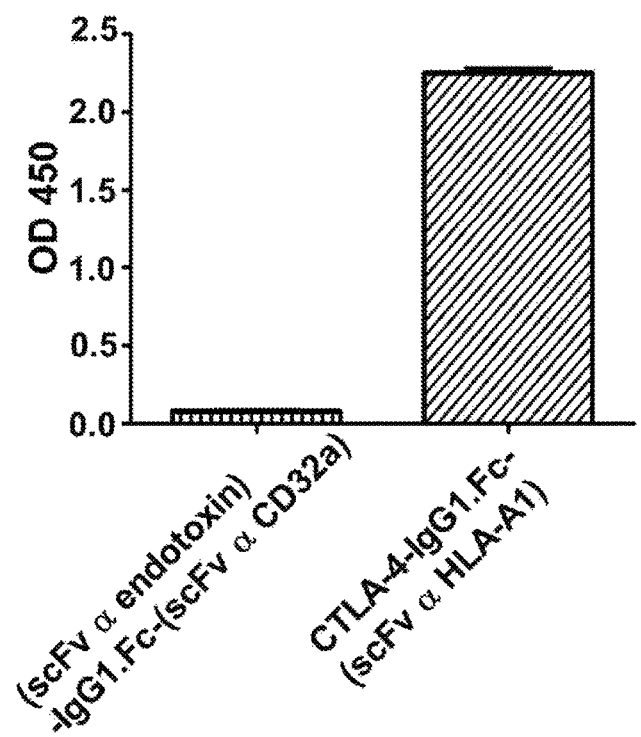
FIG. 22B and FIG. 22C respectively show the ELISA analysis of of purified recombinant 2-chain (CTLA-4)-IgG1.Fc-(scFv α HLA-A1) fusion protein with the scFv specific for CTLA-4 and with human HLA-A1, according to one working example of the present disclosure.

FIG. 22B shows ELISA analysis of the present the molecular construct. The ELISA results show that CTLA-4-hIgG1.Fc-(scFv α HLA-A1) fusion protein was bound specifically by scFv specific for CTLA-4. The scFv specific for CTLA-4 was prepared in our laboratory described in PCT patent application publication No. WO/2016112870.

Binding activity of recombinant CTLA-4-hIgG1.Fc-(scFv α HLA-A1) to was assayed by ELISA using a 96-well plate coated with recombinant HLA-A1 protein in 5 µg/ml concentration, 100 µl per well. The GST protein (a sample from Dr. Kuo I Lin, Genomics Research Center, Academia Sinica, Taipei, Taiwan) was used as a negative control.

After treated with 200 µl of blocking buffer for 1 hour, 100 µl of recombinant CTLA-4-hIgG1.Fc-(scFv α HLA-A1) in 5 µg/ml concentration was added to the coated plate for another 1 hour. Then, HRP-conjugated goat anti-human IgG.Fc (1:2000) was added to the coated plate for 1 hour. Next, 50 µl of TMB substrate was added for color development. The reaction was stopped by 50 µl of 1M HCl. Absorbance at 450 nm was measured with a plate reader. Each bar represents the mean OD450 value of duplicate samples.

Figure 22C:
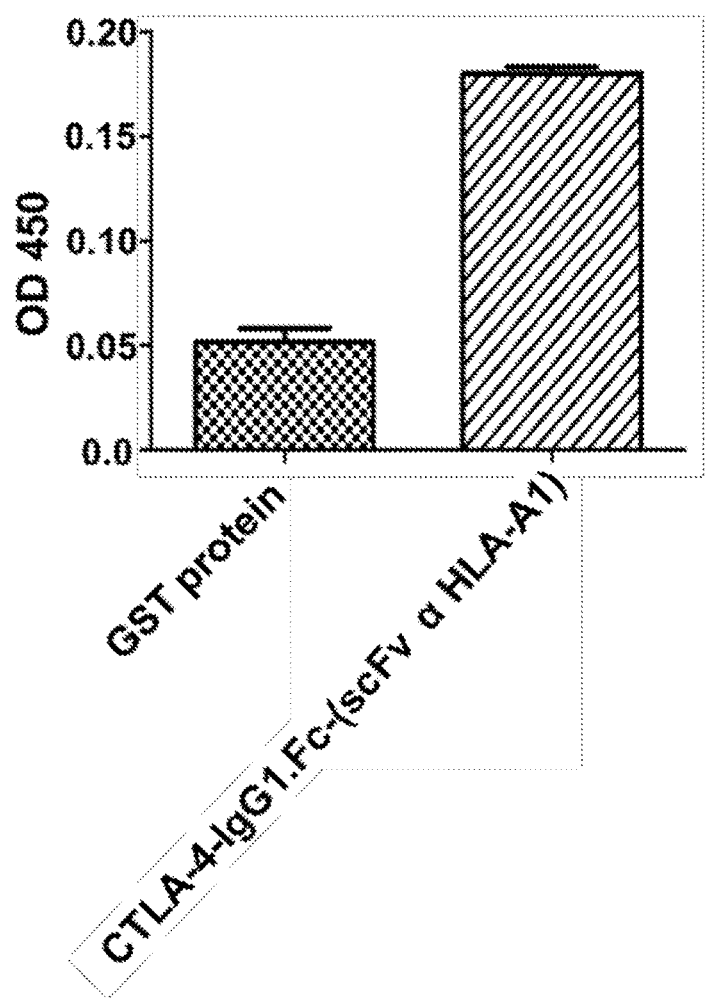

FIG. 22C shows ELISA analysis of the present the molecular construct. The ELISA results show that CTLA-4-hIgG1.Fc-(scFv α HLA-A1) fusion protein was bound specifically to human HLA-A1.

Example 32: Preparation of Recombinant 2-Chain (PD-L1)-hIgG4.Fc-(scFv α HLA-A1) Fusion Protein The PD-L1-CH2-CH3-scFv (human γ4) recombinant chain was configured by fusing human PD-L1 to the N-terminal of CH2 domain of IgG4.Fc through a flexible hinge region, and the scFv 4-35-7 specific for human HLA-A1 was fused to the C-terminal of CH3 domain through a flexible linker, (GGGGS)$_3$.

The scFvs had an orientation of V$_L$-linker-V$_H$. The V$_L$ and V$_H$ in the scFv was connected by a hydrophilic linker, (GGGGS)$_3$. The sequence of the recombinant chain in the IgG4.Fc fusion protein molecular construct is shown as SEQ ID NO: 36.

Figure 23A:
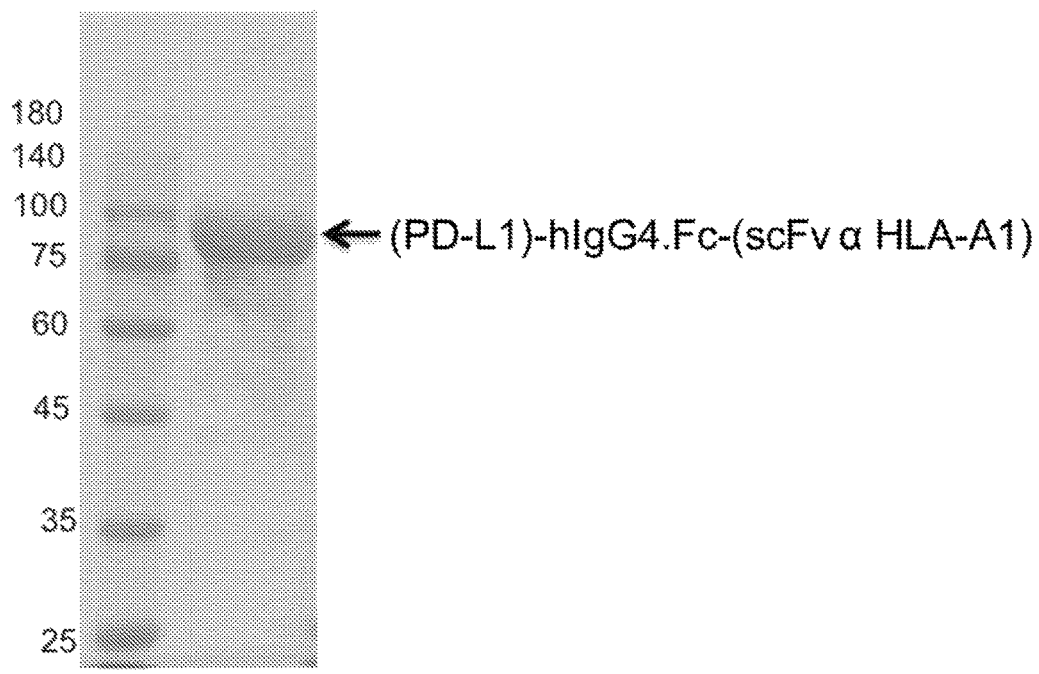
FIG. 23A shows the SDS-PAGE analysis of purified recombinant 2-chain (PD-L1)-IgG4.Fc-(scFv α HLA-A1) fusion protein.

Characterization of the new construct was performed with SDS-PAGE and ELISA. The SDA-PAGE results in FIG. 23A shows that the recombinant chain of the new construct has a size of about 80 kDa (indicated by arrow), consistent with the expected size.

Figure 23B:
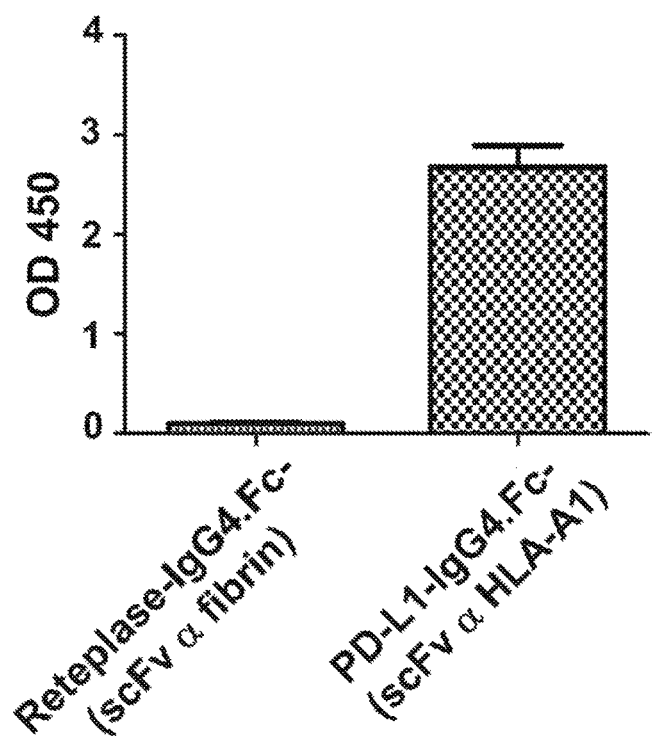
FIGS. 23B to 23D respectively show the ELISA analysis of purified recombinant 2-chain (PD-L1)-IgG4.Fc-(scFv α HLA-A1) fusion protein with the mAb specific for PD-L1, human PD-1, and human HLA-A1, according to one working example of the present disclosure.

Binding activity of recombinant (PD-L1)-hIgG4.Fc-(scFv α HLA-A1) was assayed by ELISA using a 96-well plate coated with recombinant (PD-L1)-hIgG4.Fc-(scFv α HLA-A1) protein in 5 µg/ml concentration, 100 µl per well. After the excess (PD-L1)-hIgG4.Fc-(scFv α HLA-A1) was washed off and the solid phase blocked, 100 µl per well of anti-PD-L1 antibody at 5 µg/ml was added. The bound anti-PD-L1 antibody was determined by HRP-conjugated goat anti-human IgG.Fc. 50 µl of TMB substrate was added for color development. The reaction was stopped by 50 µl of 1M HCl. Absorbance at 450 nm was measured with a plate reader. Each bar represents the mean OD450 value of duplicate samples. FIG. 23B shows the ELISA result indicates that the mAb specific for human PD-L1 (MPDL3280A, a sample from Dr. An Suei Yang, Genomics Research Center, Academia Sinica, Taipei, Taiwan) specifically bound to (PD-L1)-hIgG4.Fc-(scFv α HLA-A1).

Figure 23C:
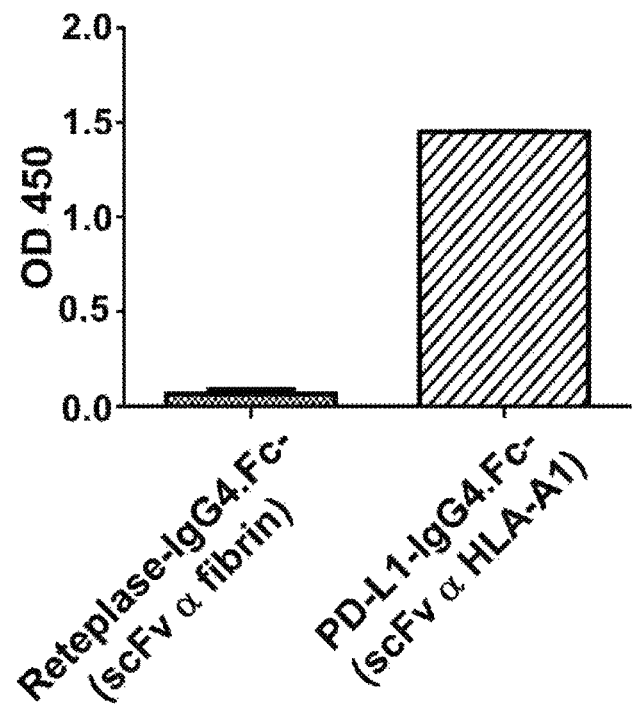
Figure 23D:
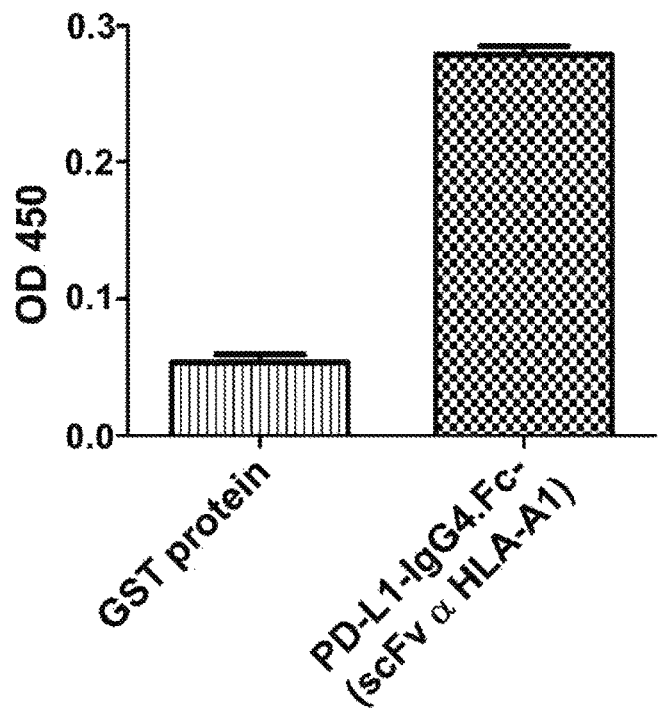

Binding activity of recombinant (PD-L1)-hIgG4.Fc-(scFv α HLA-A1) was assayed by ELISA using a 96-well plate coated with recombinant (PD-L1)-hIgG4.Fc-(scFv α HLA-A1) protein in 10 µg/ml concentration, 100 µl per well. After the excess (PD-L1)-hIgG4.Fc-(scFv α HLA-A1) was washed off and the solid phase blocked, 100 µl per well of PD1-IgG1.Fc at 10 µg/ml was added. The bound PD1-IgG1.Fc was determined by HRP-conjugated goat anti-human IgG.Fc (1:2000). 50 µl of TMB substrate was added for color development. The reaction was stopped by 50 µl of 1M HCl. Absorbance at 450 nm was measured with a plate reader. Each bar represents the mean OD450 value of duplicate samples. FIG. 23C shows that the recombinant human (PD-L1)-hIgG4.Fc-(scFv α HLA-A1) specifically bound to recombinant (PD1)-hIgG1.Fc. The (reteplase)-hIgG4.Fc-(scFv α fibrin) fusion protein (prepared by our laboratory) was as a negative control.

Binding activity of recombinant (PD-L1)-hIgG4.Fc-(scFv α HLA-A1) to human HLA-A1 was assayed by ELISA using a 96-well plate coated with recombinant human HLA-A1 protein in 10 µg/ml concentration, 100 µl per well. After the excess HLA-A1 protein was washed off and the solid phase blocked, 100 µl per well of (PD-L1)-hIgG4.Fc-(scFv α HLA-A1) at 10 µg/ml was added. The bound (PD-L1)-hIgG4.Fc-(scFv α HLA-A1) was determined by HRP-conjugated goat anti-human IgG.Fc. 50 µl of TMB substrate was added for color development. The reaction was stopped by 50 µl of 1M HCl. Absorbance at 450 nm was measured with a plate reader. Each bar represents the mean OD450 value of duplicate samples. FIG. 18D shows that the recombinant human (PD-L1)-hIgG4.Fc-(scFv α HLA-A1) specifically bound to recombinant HLA-A1. The GST protein was used as a negative control.

Illustrated below is the configuration of the prepared 2-chain (PD-L1)-hIgG4.Fc-(scFv α HLA-A1) molecular construct

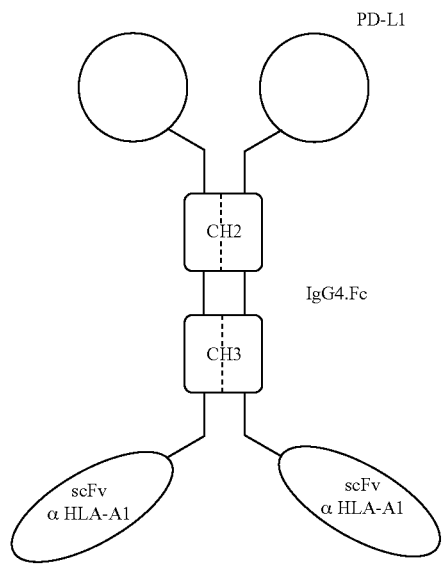

Example 33: Construction of a Gene Segment Encoding 2-Chain (scFv α CD25)-hIgG4.Fc-(scFv α HLA-A1) Fusion Protein The $V_L$ and $V_H$ of the scFv specific for human CD25 were from monoclonal antibody dacilizumab. The 2-chain IgG.Fc fusion protein was prepared by configuring (scFv α CD25)-CH2-CH3-(scFv α HLA-A1) (human γ4) in a recombinant chain. The C-terminal of the scFv specific for human CD25 was fused to the N-terminal of CH2 via a short linker, ASGGS. The scFv specific for HLA-A1 was fused to the C-terminal of CH3 domain through a flexible linker, (GGGGS)$_3$.

The two scFv had the orientation of $V_L$-linker-$V_H$. The $V_L$ and $V_H$ in each of the two scFv were connected by a hydrophilic linker, (GGGGS)$_3$. The sequence of the recombinant chain in the IgG4.Fc fusion protein molecular construct is shown as SEQ ID NO: 37. The preparation of the Fc. Fusion protein was the same as described in the preceding Example.

Illustrated below is the configuration of the prepared 2-chain (scFv α CD25)-IgG4.Fc-(scFv α HLA-A1) molecular construct.

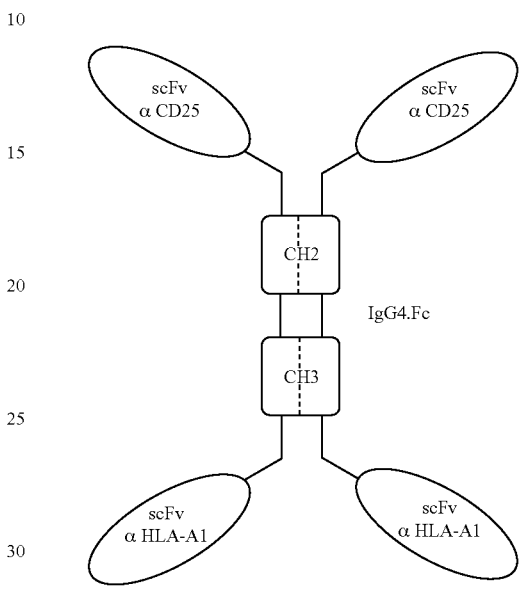

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A linker unit comprising, a center core, a plurality of linking arms, a plurality of first elements, optionally, a coupling arm, and, optionally, a second element, wherein,
the center core is (1) a first polypeptide comprising 2 to 15 K resides and one or more filler sequences separating each K residue and its next K residue, wherein the filler sequence comprises glycine (G) and serine (S) residues; or (2) a second polypeptide comprising the sequence of $(X_{aa}\text{-}K)_{2\text{-}15}$, where $X_{aa}$ is a PEGylated amino acid having 2 to 12 repeats of ethylene glycol (EG) unit;
the plurality of linking arms are respectively linked to the K residues of the center core;
the amino acid residue at the N- or C-terminus of the center core has an azide or alkyne group; or the amino acid residue at the N- or C-terminus of the center core is a cysteine residue, and the thiol group of the cysteine residue is linked with the coupling arm; and
the coupling arm has an azide, alkyne, tetrazine, cyclooctene, or cyclooctyne group at the free terminus thereof,
the plurality of first elements are respectively linked to the plurality of linking arms via forming an amide bound therebetween, or via thiol-maleimide reaction, copper catalyzed azide-alkyne cycloaddition (CuAAC) reaction, strained-promoted azide-alkyne click chemistry (SPAAC) reaction, or inverse electron demand Diels-Alder (iEDDA) reaction;

the second element, if present, is linked to the center core or the coupling arm via CuAAC reaction, SPAAC reaction, or iEDDA reaction;

each of the first elements is a targeting element and the second elements is an effector element, or vice versa, wherein the targeting element is a single-chain variable fragment (scFv) that is specific for a human leukocyte antigen (HLA) allotype present only on cells of a donor transplant, and comprises the amino acid sequence of SEQ ID NO: 32 or 34; and the effector element is sirolimus, everolimus, tacrolimus, fingolimod, fingolimod phosphate, an ectodomain or extracellular domain of cytotoxic T lymphocyte associated protein 4 (CTLA-4), an ectodomain or extracellular domain of programmed death-ligand 1 (PD-L1), or an scFv that is specific for CD25, and comprises the amino acid sequence of SEQ ID NO: 33; wherein, when the plurality of first elements are respectively linked to the plurality of linking arms via CuAAC or SPAAC reaction, then the amino acid residue at the N- or C-terminus of the center core is a cysteine residue, and the free terminus of the coupling arm is the tetrazine or the cyclooctene group; or when the plurality of first elements are respectively linked to the plurality of linking arms via iEDDA reaction, then the amino acid residue at the N- or C-terminus of the center core has the azide or the alkyne group, or the amino acid residue at the N- or C-terminus of the center core is a cysteine residue, and the free terminus of the coupling arm is the azide, the alkyne, or the cyclooctyne group.

2. The linker unit of claim 1, wherein the filler sequence has the sequence of GS, GGS, GSG, or SEQ ID NOs: 1-16.

3. The linker unit of claim 1, wherein the first polypeptide comprises 2-15 units of the sequence of $G_{1-5}SK$.

4. The linker unit of claim 3, wherein the first polypeptide comprises the sequence of $(GSK)_{2-15}$.

5. The linker unit of claim 1, wherein each of the linking arms is a PEG chain having 2-20 repeats of EG units.

6. The linker unit of claim 1, wherein the coupling arm is a PEG chain having 2-12 repeats of EG units.

7. The linker unit of claim 1, wherein the amino acid residue having the azide group is L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine.

8. The linker unit of claim 1, wherein the amino acid residue having the alkyne group is L-homopropargylglycine (L-HPG), D-homopropargylglycine (D-HPG), or beta-homopropargylglycine (β-HPG).

9. The linker unit of claim 1, wherein the cyclooctene group is trans-cyclooctene (TCO); and the cyclooctyne group is dibenzocyclooctyne (DBCO), difluorinated cyclooctyne(DIFO), bicyclononyne (BCN), or dibenzocyclooctyne (DICO).

10. The linker unit of claim 1, wherein the tetrazine group is 1,2,3,4-tetrazine, 1,2,3,5-tetrazine, 1,2,4,5-tetrazine, or 6-methyl tetrazine.

11. The linker unit of claim 1, wherein the second element is linked to the azide or alkyne group of the N- or C-terminal amino acid residues of the center core via CuAAC reaction or SPAAC reaction.

12. The linker unit of claim 11, further comprising a third element that is linked to the coupling arm via iEDDA reaction.

13. The linker unit of claim 12, wherein the third element is a long PEG chain having a molecular weight of about 20,000 to 50,000 Daltons.

* * * * *